US008829277B2

(12) United States Patent
Spangenberg et al.

(10) Patent No.: US 8,829,277 B2
(45) Date of Patent: Sep. 9, 2014

(54) MANIPULATION OF PLANT SENESCENCE USING MODIFIED PROMOTERS

(71) Applicant: Agriculture Victoria Services Pty Ltd., Attwood (AU)

(72) Inventors: German Spangenberg, Bundoora (AU); Carl McDonald Ramage, Bundoora (AU); Melissa Ann Palviainen, Eden Park (AU); Roger W. Parish, Warrandyte (AU); Joshua Heazlewood, Kensington, CA (US)

(73) Assignees: Agriculture Victoria Services Pty Ltd., Attwood (AU); La Trobe University, Bundoora (AU)

( * ) Notice: Subject to any disclaimer, the term of this patent is extended or adjusted under 35 U.S.C. 154(b) by 0 days.

(21) Appl. No.: 13/790,324

(22) Filed: Mar. 8, 2013

(65) Prior Publication Data
US 2013/0254942 A1 Sep. 26, 2013

Related U.S. Application Data

(63) Continuation of application No. 12/605,214, filed on Oct. 23, 2009, now Pat. No. 8,399,739, which is a continuation-in-part of application No. 11/789,526, filed on Apr. 24, 2007, now abandoned, and a continuation-in-part of application No. PCT/AU2008/000566, filed on Apr. 21, 2008.

(51) Int. Cl.
*A01H 5/00* (2006.01)
*A01H 1/00* (2006.01)
*C12N 15/09* (2006.01)
*C12N 15/82* (2006.01)

(52) U.S. Cl.
USPC ........ 800/290; 800/278; 800/298; 435/320.1; 435/419; 435/468

(58) Field of Classification Search
USPC ........ 800/290, 278, 298; 435/320.1, 468, 419
See application file for complete search history.

(56) References Cited

U.S. PATENT DOCUMENTS 8,399,739 B2 * 3/2013 Spangenberg et al. ....... 800/290
2004/0025205 A1 2/2004 Spangenberg

FOREIGN PATENT DOCUMENTS

WO 96/29858 A1 10/1996
WO 00/70061 A2 11/2000
WO 02/20772 A1 3/2002

OTHER PUBLICATIONS

Search Report issued in corresponding Taiwan Application No. 97114829, filed Apr. 23, 2008, 1 page.
Siefritz, F., "Expression and Function of the *Nicotiana tabacum* Aquaporin NtAQP1," doctoral dissertation, Bayerischen Julius-Maximilians-Universität, Würzburg, Germany, 2002, 146 pages.
Extended European Search Report mailed Jun. 1, 2010, issued in corresponding European Patent Application No. 08 73 3383.7, filed Apr. 21, 2008, 8 pages.
Extended European Search Report mailed Mar. 29, 2012, issued in corresponding European Patent Application No. 12 15 3159.4, filed Apr. 21, 2008, 7 pages.
Gan, S., and R.M. Amasino, "Developmental Targeting of Gene Expression by the Use of a Senescence-Specific Promoter," in P.H.S. Reynolds (ed.), "Inducible Gene Expression in Plants," CAB International, Wallingford, U.K., 1999, pp. 169-186.
Gan, S., and R.M. Amasino, "Inhibition of Leaf Senescence by Autoregulated Production of Cytokinin," Science 270(5244):1986-1988, Dec. 1995.
International Search Report and Written Opinion mailed Jun. 27, 2008, issued in corresponding International Application No. PCT/AU2008/00056, filed Apr. 21, 2008, 8 pages.
Kranz, H.D., et al., "Towards Functional Characterisation of the Members of the R2R3-MYB Gene Family From *Arabidopsis thaliana*," Plant Journal 16(2):263-276, Oct. 1998.
Li, S.F., et al., "A Novel myb-Related Gene From *Arabidopsis thaliana*," FEBS Letters 379(2):117-121, Jan. 1996.
Lin, Y.-H., et al., "Organ-Specific, Developmentally-Regulated and Abiotic Stress-Induced Activities of Four *Arabidopsis thaliana* Promoters in Transgenic White Clover (*Trifolium repens* L. )," Plant Science 165(6):1437-1444, Dec. 2003.
Sidorenko, L.V., et al., "Complex Structure of a Maize Myb Gene Promoter: Functional Analysis in Transgenic Plants," Plant Journal 22(6):471-482, Jun. 2000.
Smart, C.M., et al., "Delayed Leaf Senescence in Tobacco Plants Transformed With tmr, a Gene for Cytokinin Production in *Agrobacterium*," Plant Cell 3(7):647-656, Jul. 1991.
Zhang, J., et al., "Development of Flooding-Tolerant *Arabidopsis thaliana* by Autoregulated Cytokinin Production," Molecular Breeding 6(2):135-144, Apr. 2000.

* cited by examiner

*Primary Examiner* — Medina A Ibrahim
(74) *Attorney, Agent, or Firm* — Christensen O'Connor Johnson Kindness PLLC

(57) ABSTRACT

The present invention relates to methods of manipulating senescence in plants. The invention also relates to vectors useful in such methods, transformed plants with modified senescence characteristics and plant cells, seeds and other parts of such plants.

17 Claims, 65 Drawing Sheets

```
  1 gtttgtgtcg tctagattaa tctccaaac tttgattaa ccaaaaaat tatcaaata
 61 acatgtttctc ctttctctt tagaattct aacgattta tcttatact gattgaata
                                              <<<  XcmI  >>>
121 tacttaattt ggtcattgt atgccttta cacctcctt acaaactca ctatgcaaa
181 tatatactat tctccattgc aacataaatg tcatcaatt gaattaatt cgtgcagta
241 cgaaaccatc cactttgtc caaaacaaa atccttataa ctattactt taagtaaat
301 atatcctcta cttttgttt tacaagccta gtcaaacaa attcattatt tgcgataaaa
361 aatcatatcg aacaaactcg atgattttt tttcttacg tcattaatga aactaaaata
421 tagaaaaaaa caagatgacc caaatttcca cctatctaac tacttaaata taatatgatt
                                                      <  SapI >
481 aaattggtta aagtttgaaa agttctttta gaaatgtgaa atattgatca cagttctat
541 tgctaaaatc accaacaaa cgcatgtcgc cattcataat tatggttca cacctacaac
601 taggctaata agtaaataag tagacaacta gactcaggtt tgaaaaacc ataaaagcca
661 tatagcgttt tctcattgaa actgcgaaca cgatcgtgtg aatgttgcag tttctagttt
721 tgatacaaac aaacaaaaac acaatttaat cttagattaa aagaaaaaa gagaacggag
781 ctcactagcc actccttcaa actgtgtcta ccactctct tctagaaaca aattaggctt
841 cacctttcctc ttccaagcto tctctctctc tctctcttt tttctcaaag catctctca
901 taaagcccta attcttcat cacaagaatc agaagaagaa a
```

Figure 1.

```
  1 gtttgtgtct tctagattaa tcctccaaac tttgattaa cgaaaaaat tatcaacta
 61 acatgttctc ctttttctt tagaattct aacgaattta tctttaact gattgaata
121 tacttaattt ggtcatttgg atgtcttta caccctctt ancaactca ttgatcacag
181 ttgtattgc taaatcacc aacaaacgc atgtcgcat tratcattat ggtttcacac
241 ctacaactag gctaatasgt aaataagtag acaactagac tcaggtttga aagaaccata
301 aaagccatat agcgtttct cattgaact gcgaacanga tcgtgtgaat gttgcagttg
361 ctagtttga tacaaacaaa caaaacaca attaatctt agattaaaag gagaaaagag
421 aacggagccc actagccact ccttcaaacg tgtcttacca actctcttct agaaacaaat
481 taggttcac cttcctct gaacttctc ctctctctct ctctcttt gtgaaccat
541 ctctccatac agccctaatt tcttcctcac aagaatcaga agaagaa
```

Figure 2.

```
  1 tacttaattt ggtcatttgg atgcctttta caacutcctt atcaactca ttgatcacag
 61 ttctgattgc taaatcacc aacaaaacgc atgtcgccat tcataatcat ggttcacac
121 ctacaactag gctaataagt aaataagtag acaactagac tcaggtttga aaaaacata
181 aaagccatat agcgtcttct cattgaaact gcgaacacga tcgtgtgaat gttgcagttt
241 ctagtttga tacaaacaaa caaaaacaca attcactctt agattaaaag gaaaaagag
301 aacggagcc actagccact cctcaaacg tgtcttacca actctctcct agaaacaaat
361 taggcttcac ctccctctt caacc tctct ctcctctct ctctcttttt ctcaaaccat
421 ctctccataa agcctaatt tcttcatcac aagaatcaga agaagaaa
```

Figure 3.

```
  1 atgatcaca gttcgactg ctaaaatcac cacaaaacg catgtcgtca ttcttaacta
 61 tggtttcaca cctacaacta ggctaatasg tasataagta gacactaga ctcaggtttg
121 aaaaaaccat aaaagccata cagtgttctc tcattgaaat tgcgaacacg atcgtgtgaa
181 tgttgcagtt tctagttttg atacaaacaa acaaaaacac aattaatct cagattaaaa
241 agaaaaaaga gaacggagct ctctagccac tcctccaaa gtgtcttacc aactctcttc
301 cagaaacaaa ttaggcttca ccttcctctt cagaacctc tctctctcta tctctcttt
361 ctcgaaaca tcttcata aagcctaat ttcttcatca ccagatcag aagaagaa
```

Figure 4.

```
  1 atggacctgc atctaatttt cggtccaact tgtacaggaa agacgacgac cgcgatagct
 61 cttgcccagc agacaggct tccagtcctt tcgcttgatc gggtccaatg ctgtcctcaa
121 ctatccaccg gaagcggacg acaacagtg gaagaactga aaggaacgac gcgtctctac
181 cttgatgatc ggctctggt ggagggtatc atcgcagcca agcaagctca tcataggctg
241 atcgaggagg tgtataatca tcaggtccac ggcgggctta ttcttgaggg aggatccacc
301 tcgttgctca actgcatggc gcgaaacagc tatggagtg cagatttcg ttggcatatt
361 attcgccaca agttaccga tcaagagcc ttcatgaaag cggtcaaggc cagagttaag
421 cagatgttgc acccgctgc aggccattct attattcaag agttggttta tcttggaat
481 gaacctggc tgaggccrat tctgaaagag atcgatggat atcgatatgc catgttgttt
541 gctagccaga accagatcac ggcagatatg ctattgcagc ctgaccgcaaa tatggaaggt
601 aagttgatta atgggatcgc tcaggagtat ttcatccatg cgcgccaaca ggaacagaaa
661 ttccccaag ttaccgcagc cgctttcgac ggattcgaag gtcatccgtt cggaatgtat
721 tag
```

Figure 6.

```
  1 MDLHLIFGPT CTGKTTTAIA LAQQYGLPVL SLDRVQCCPQ LSTGSGRPTV EELKGTTRLY
 61 LDDRPLVEGI IAAKQAHHRL IEEVYNHEAN GGLILEGGST SLLNCMARNS YWSADFRWHI
121 IRHKLPDQET FMKAAKARVK QMLHPAAGHS IIQELVYLWN EPRLRPILKE IDGYRYAMLF
181 ASQNQITADM LLQLDANMEG KLINGIAQEY FIHARQQEQK FPQVNAAAFD GFEGHPFGMY
241 *
```

Figure 7

```
  1 atgtccatct caatgctaat gtgcagacta agacaaccct taataaacgt ttcctgcagt
 61 ggcaaaaaac tgagcatgag gcagattcaa aaggagaagg tagtgttggt gatggagct
121 acaaggacag gaaagtcaaa gctctccatt gactctgcca cctgttccc ctcagaaatc
181 atcaactccg acaagattca aatctacgac ggcctcgaca tcgtcaccaa caaaatctcc
241 aaggaagaac aacgtggaat ccccaccac ctcctcggaa ctcaaaacct taacacagac
301 ttcacccgcg gcgattcag tgactgttcc accgccgcca ttgacgcaat cacaagccgc
361 gaccaccttc cgatcatcgc cggaggttcg aactcctacc tggaggcgtt aatcgacgac
421 gacgactaca aattccgatc gaggtacgac ttctgctgcc tctggtcga cgtgcaatg
481 ccggtgctgg actcatacgt ggcggcgcgt gtggatcaga tgctccggag cggaatggtg
541 gaggagctga gaccgttttt caacgcgaac ggcgactact cgagaggaat cagaagagcg
601 attgggtc ctgaattcga cgagtatttc cggcggaag ggttcgccga tgaggaacg
661 aggaaattgt tactggagcg agcggtgagg gagatgaagg tgaacacgtg caagctgcg
721 aggaggcaat tgggaagat tcagaggctg aggaatgtga agaggtggga gatccacgt
781 gctgatgcga cgccggtgtt ttggaagcgt gggaggagg ctgatgaggc gtgcggaag
841 gtggtggcag agcctagtgc tatgatcgta gcgcagtttc tgtataggc aaagagtgat
901 gtgaatgttg tttctggcg tttcagagtg ccggcgggt caaggagag tgttatggcg
961 ggggagacgt gttag
```

Figure 8.

```
  1 MSISMLMCRL RQPLINVPCS GKKLSMRQIQ KEKVVLVMGA TGTGKSKLSI DLATCFPSEI
 61 INSDKIQIYD GLDIVTNKIS KEEQRGIPHH LLGTQNPNTD FTAGDFSDCS TAAIDAITSR
121 DHLPIIAGGS NSYLEALIDD DDYKFRSRYD FCCLWVDVAM PVLDSYVAAR VDQMLRSGMV
181 EELRPFFNAN GDYSRGIRRA IGVPEFDEYF RREGFADEET RKLLLERAVR EMKVNTCKLA
241 RRQLGKIQRL RNVKRWEIHR VDATPVFWKR GEEADEAWRK VVAEPSAMIV AQFLYKAKSD
301 VNVVSGGFRV PAGSTESVMA AATC*
```

Figure 9.

```
   1 atgttaattg tagtacatat tattagcatc acacgcatca tattcatcac cttaacccat
  61 aatcatctcc atttccttat gttagatca ttatcataca atcacaagca cctcaaattc
 121 cttacaaacc cgaccacacg ggtactccga agaaacatgt cgtcatcac tgtagtaaca
 181 ataccggcc ccacacaaaa aaacaaaaac aaaatcatag taataatggg tgcaacaggt
 241 tcaggaaaat caaaactctc aatagaccta gtcacacgtc actatccttt ttccgaaatc
 301 attaactccg acaaaatcca aattaccaaa ggtttaaaca taaccacaaa caaaatcact
 361 gtaaccgacc gacgtgggagt agtcatcat ttactcggcg agattgaccc cgactttaac
 421 tttctcctt ctcatttccg gtcaattgct ggtcaacgca ttaactccat tattaatcgc
 481 cataaactcc cattcctcgt tggtggtcc aactcatata tctacgcttt attaacaaac
 541 cggttcgacc cggatttaa ccctgattca aaccggttc attttatatc caacgagtta
 601 cgctacaact gttgttttat ttgggtcgat gtattaaacc cggtttgaa tgagtatttg
 661 gataaacggg tcgatgagat gatgaactcg ggtatgtatg aagaactgga acagttttt
 721 aaagaaaaca ggttttcgga tccgggtttg gaacgggtc gggcaacgg gttgaggaaa
 781 gcgatagggg tacggaaat ggagaggtat ttaagaaga gctgtacgta tgaggaagca
 841 gtgagggaaa taaagaaaa cacgtggcgg ttagcgaaga agcagatgtg gaagatccaa
 901 cggttgagag aagcagggtg ggacctacaa agagtagatg caccggaggc atttgtggag
 961 gcgatgagta ataagaagga aaagggaatt atttgggaaa aacaagtagt ggaaccaagt
1021 gtcaagattg tgaaccgttt ttgttggac tga
```

Figure 10

```
  1 MLIVVHIISI TRIIFITLTH NHLHFLMFRS LSYNHKHLKF LTNPTTRVLR RNMSSSTVVT
 61 IPGPTQKNKN KIIVIMGATG SGKSKLSIDL VTRHYPFSEI INSDKIQITK GLNITTNKIT
121 VPDRRGVVHH LLGEIDPDFN FSPSHFRSIA GQRINSIINR HKLPFLVGGS NSYIYALLTN
181 RFDPDFNPDS NPVHFISNEL RYNCCFIWVD VLNPVLNEYL DKRVDEMMNS GMYEELEQFF
241 KENRFSDPGL EPGRATGLRK AIGVPEMERY FKKSCTYEEA VREIKENTWR LAKKQMWKIQ
301 RLREAGWDLQ RVDATEAFVE AMSNKKEKGI IWEKQVVEPS VKIVNRFLLD *
```

```
6181 ggtgtggagg aacgctatca ggacatagcg ttggctaccc gtgatattgc tgaagagctt
6241 ggcggcgaat gggctgaccg cttcctgtg ctttacggta tcgctgctcc cgattcgcag
6301 cgcatcgcct tctatcgcct tcttgacgag tcttctgaa cccagcttc ttgtacaaag
6361 tggagtccgc aaaatcacc agtctctctc tacaaatcta tctctctcta tttttctcca
6421 gaataatgtg tgagtagttc ccagataagg gaattagggt tcttataggg tttcgctcat
6481 gtgttgagca tataagaaac cctagtatg tatttgtatt tgtaaastac ttctatcaat
6541 aaaatttcta attcctaaaa ccaaatcca gtgacctcaa cttattata catgttgat
6601 aattcactgg ccgtgcttat tccatggctg caggtcgacg aattcaccgg ttagggataa
6661 caggggtaatc gctaccttag gaccgttata gttacggcca gtgccattac cctgttatcc
6721 ctaaccggtg acaacttgt atagaaaagt tggttgtgt cttctagatt aatcctccaa
6781 acttttgatt aaccaaaaaa attatcaaat taacatgttc tccttttttc tttagaaatt
6841 ctaacgaatt tatctttata ctgatttgaa tatacttaat ttggtcattt ggatgccctt
6901 tacaacctcc ttaccaaact cactatggca aatatatact attttccatt gtaacataaa
6961 tgtccataat ttgaattaaa ttcgttgcag tacgaaaacta tccaactttg tccaaaaaca
7021 aaatccttat aactatttac tttaatgtaa atatatcctc tactttgtt tttacaaccc
7081 tagctcaaac aaattattca ttgcgataa aaaatcatat cgaacaaact cgatgatttt
7141 tttttcctta cgttattaat gaaactaaaa tatagaaaaa aacaagatga accaaatttt
7201 cacctatcta actacttaaa tataatatga ttaaatttgg taaagtttga aaagtttctt
7261 tagaaatgtg aaatattgat cacagtttct attgctaaaa tcaccaacaa aacgcatgtc
7321 gccattcata attatggttt cacagctaca actaggctaa taagtaaata agtagacaac
7381 tagactcagg tttgaaaaa ccataaaagc catatagcgt ctctcattg aaactgcgaa
7441 cacgatcgtg tgaatgttgc agtttctagt ttgatacaa acaaacaaaa acacaattta
7501 atcttagatt aaaagaaaa aagagaacgg agcccactag ccactcctcc aaacgtgtct
7561 taccaactct cttctagaaa caaattaggc ttcaacttcc tcttcaaacc tctctctctc
7621 tctctctctc ttttttctcaa accatctctc cataaagccc taattttctc atcacaagaa
7681 tcagaagagag aaacaagttt gtacaaaaaa gcaggcttac tgcaaaaac ttatggaact
7741 gcatctaatt ttcggtccaa cttgcacagg aagacgacg accgcgatag ctcttgcccca
7801 gcagacaggg cttccagtcc tttcgttga tcgggtccaa tgctgtcctc aactatcaac
7861 cggaagcgga cgaccaacag tggaagaact gaaaggaacg acgcgtctct acttgatga
7921 tggctctg gtggaggta tcatcgcagc caagcaagct catcataggc tgatcgagga
7981 gtgtataat catgaggcca acggcgggct tattcttgag ggaggatcca cctcgttgct
8041 caactgcatg gcgcgaaaca gctattggag tgcagatttt cgttggcata ttattcgcca
8101 caagttaccc gaccaagaga ccttcatgaa agcggccaag gccagagtta agcagatgtt
8161 gcacccccgct gcaggccatt ctattattca agagtcggtt tatcttttgga atgaacctcg
8221 gctgaggccc attctgaaag agatcgatgg atatcgatat gcatgttgt ttgctagcca
8281 gaacagatc acggcagata tgctattgca gcttgacgca aatatggaag gtaagttgat
8341 taatgggatc gctcaggagt atttcatcca tgcgcgcaa caggaacaga aattcccccta
8401 agttaacgca gccgctttcg acggattcga aggtcatcg ttcggaagtgt attaggtacc
8461 cagcttctt gtacaaagtg ggatcgttca aacattggc aataaagttt cttaagattg
8521 aatcctgttg ccggtcttgc gatgattatc atataaattc tgttgaatta cgttaagcat
8581 gtaataactta acatgtaatg catgacgtta tttatgagat gggtttttat gattagagtc
8641 gcgcaattat acattaacta cgcgatagaa aacaaaatat agcgcgcaaa ctaggataaa
8701 ttatcgcgcg cggtgtcatc tatgttacta gatccaactt tattatacat agtgattcg
8761 tcgacatgca gtcgctacct taggaccgtt atagttatgg caaacagcta ttatgggtat
```

Figure 17.
(Cont.)

```
8821 tatgggtggt tctttatgcg gacactgacg gctttatgcc tgcaggtcgc gagcgatcgc
8881 ggtaccgccc gggcgtcgac aggcctaagc ttagcttgag cttggatcag attgtcgttt
8941 cccgccttca gtttaaacta tcagtgtttg acaggatata tggcgggta aactaagag
9001 aaagagcgt ttattagaat aacggatatt taaagggcg tgaaaggtt tatccgttcg
9061 tccatttgta tgtgcatgcc aaccacaggg ttccctcgg gatcaaagta ctttgatcca
9121 accctcgc tgctatagtg cagtcggctt ctgacgttca gtgcagccgt cttctgaaaa
9181 cgacatgtcg cacaagtcct aagttacgcg acaggctgcc gcactgcct tttcctggcg
9241 ttttcttgtc gcgtgtttta gtcgcataaa gtagaatact tgcgactaga accggagaca
9301 ttacgccatg aacaagagcg ccgccgctgg cctgctgggc tatgcccgcg tcagcacga
9361 cgaccaggac ttgaccaacc aacgggccga actgcacgcg gcggctgca ccaagctgtt
9421 ttccgagaag atcaccggca ccaggcgga ccgccggag ctggacagga tgcttgacca
9481 cctacgcct ggcgacgttg tgacagtgac caggctagac cgcctggcc gcagcaccg
9541 cgacctactg gacattgccg agcgcatcca ggaggcggc gcggcctgc gtagcctgga
9601 agagccgtgg gccgacacca ccacgccggc cggccgcatg gtgttgaccg tgttcgccgg
9661 cattgccgag ttcgagcgtt ccctaatcat cgaccgcacc cggagcggc gcgaggccgc
9721 caaggccaga ggcgtgaagt ttggcaaccg ccctacccta accaggcgac agatcgcgca
9781 cgccgcgag ctgatcgacc aggaaggccg caccgtgaaa gagcgggtg cactgcttgg
9841 cgtgcatcgc tgaccctgt accgagcact tgagcgcaga gaggaagtga cgccaccga
9901 ggccaggcgg cgcggtgcct taccgtgagga cgcattgacc gaggccgacg cctggcggc
9961 cgccgagaat gaacgccaag aggaacaagc atgaaaccgc accaggacgg ccaggacgaa
10021 ccgttttca ttaccgaaga gatcgaggcg gagatgatcg cggccgggta cgtgttcgag
10081 ccgccgcgc agtctcaac cgtgcggctg catgaaatcc tggccggttt gctgatgcc
10141 aagctggcgg cctggcggc cagcttggcc gctgaagaaa ccgagcgccg ccgtctaaaa
10201 agtgatgtg tatttgagta aaacagcttg cgtcatgcgg tgctgcgta tatgatgcga
10261 tgagtaaata aacaaatacg caagggaac gcatgaaggt tatcgctgta cttaaccaga
10321 aaggcgggtc aggcaagacg accatcgcaa cccatctagc ccgcgccctg caactcgccg
10381 gggcgatgt tctgttagtc gattccgatc ccagggcag tgcccgcgat tgggcggcg
10441 tgcgggaaga tcaaccgcta accgttgtcg gcatcgaccg cccgacgatt gaccgcgacg
10501 tgaaggccat cggcggcgc gacttcgtag tgatcgacgg agcgccccag gcggggact
10561 tggctgtgtc cgcgatcaag gcagccgact tcgtgctgat tcggtgcag ccaagccatt
10621 acgacatatg ggccaccgcc gacctggtgg agctgttaa gcagcgcatt gagctcacgg
10681 atggaaggct acaagcggcc tttgtcgtgt cgcgggcgat caaaggcacg cgcatcggcg
10741 gtgaggttgc cgaggcgctg gctgggtacg agctgcccat tcttga
```

```
2881 ccaacccggt aagacacgac ttatcgccac tggcagcagc cactggtaac aggattagca
2941 gagcgaggta tgtaggcggt gctacagagt tcttgaagtg gtggcctaac taoggctaca
3001 ctagaaggac agtatttggt atctgcgctc tgctgaagcc agttaccttc ggaaaaagag
3061 ttggtagctc ttgatccggc aaacaaacca cgctggtag cggtggtttt ttgtttgca
3121 agcagcagat tacgcgcaga aaaaaggat ctcaagaaga tcctttgatc ttttctacgg
3181 ggtctgacgc tcagtggaac gaaaactcac gttaagggat tttggtcatg catgatatat
3241 ctcccaattt gtgtaggct tattatgcac gcttaaaaat aataaagca gacttgacct
3301 gatagtttgg ctgtgagcaa ttatgtgctt agtgcatcta atcgcttgag ttaacgccgg
3361 cgaagcggcg tcggcttgaa cgaattctcta gctagacatt atttgccgac taccttggtg
3421 atctcgcctt tcacgtagtg gacaaattct tccaactgat ctgcgcgcga gtccaagcga
3481 tcttcttctt gtccaagata agcctgtcta gcttcaagta tgacgggctg atactgggcc
3541 ggcaggcgct ccattgccca gtcggcagcg acatccttcg gcgcgatttt gccggttact
3601 gcgctgtacc aaatgcggga caacgtaagc actacatttc gctcatcgcc agcccagtcg
3661 ggcggagagt tccatagcgt taaggttca tttagcgctt caaatagatc ctgttcagga
3721 accggatcaa agagttcctc cgccgctgga ctaccaagg caacgctatg ttctcttgct
3781 tttgtcagca agtagccag atcaatgtcg atgtggctg gctcgaagat aactgcaaga
3841 atgtcattgc gctgccatc tccaatgc agttcgcgct tagctggata acgccacgga
3901 atgatgtgt cgtgcaccaa aatggtgact tctacagcgc ggagaatctc gctctatcca
3961 ggggaagccg aagttctcaa aagtcgttg atcaaagctc gcdgcgttgt ttcatcaagc
4021 cttacggtca acgtaaccag caaatcaata tcactgtgtg gcttcaggcc gccatccact
4081 ggggagccgt acaaatgtac ggccagcaac gtcggttcga gatggcgctc gatgacgcca
4141 actacctctg atagttgagt cgatacttcg gcgatcacg cttcccccat gatgtttaac
4201 tttgtttag gacgactgcc ctgctgcgta acatcgttgc tgctccataa catcaaacat
4261 cgacccacgg cgtaacgcgc ttgctgcttg gatgcccgag gcatagactg taccccaaaa
4321 aaacatgtca tacacaagag ccatgaaaac cgccactgcg ccgttaccac cgctgcgttc
4381 ggtcaaggtt ctgaccagt tgcgtgacgg cagttacgct actgcatta cagttacga
4441 accgaacgag gcttatgtcc actgggttcg tgccggaatt gatcacaggc agcaacgctc
4501 tgtcatcgtt acaatcaaca tgctacccc cgcgagatca tccgtgttta aaacccggca
4561 gcttagttgc cgttcttccg aatagcatcg gtaacatgag caaagtctgc cgccttacaa
4621 cggctctccc gctgacgccg tcccggactg atgggctgcc tgtatcgagt ggtgattttg
4681 tgccgagctg ccggtcgggg agctgttggc tgctggtgg caggatatat tgtggtgtaa
4741 acaattgacc gcttagacaa cttaataaca cattgcggac gtttttaatg tactgaatta
4801 acgcggaatt gaattcctcg agtacgtagg atccatttaa attctagagg cgcgcgata
4861 tctctctta aggtagcgag ctcttaatta ataggatcaa caggtaatg cggccgcaag
4921 ctaaaacgac ggccagtgaa ttatcaactt tgtatagaaa agttgctctg ccgacagtgg
4981 tccaaagat ggaccccac ccacgaggag catcgtggaa aagaagacg ttccaaccac
5041 gtcttcaaag caagtggatt gatgtgataa catggtggag cacgacactc tcgtctacta
5101 caagaatatc aagatacag tctcagaaga ccaaagggct attgagactt ttcaacaaag
5161 ggtaatatcg ggaaacctcc tcggattcca ttgcccagct atctgtcact tcatcaaaag
5221 gacagtagaa aaggaaggtg gcacctacaa atgccatcat tgcgataaag gaaaggctat
5281 cgttcaagat gcctctgccg acagtggtcc caaagatgga cccccaccca cgaggagcat
5341 cgtggaaaaa gaagacgttc caaccacgtc ttcaaagcaa gtggattgat gtgatatctc
5401 cactgacgta agggatgacg cacaatccca ctatccttcg caagaccttc ctctatata
5461 aggaagttca tttcatttgg agaggacacg ctgcaagtct gtacaaaaaa gcaggctaga
5521 acggggggca atgagatatg aaaaagcctg aactcaccgc gacgtctgtc gagaagtttc
5581 tgatcgaaaa gttcgacagc gtctccgacc tgatgcagct ctcggagggc gaagaatctc
5641 gtgctttcag cttcgatgta ggagggcgtg gatatgtcct gcggtaaat agctgcgccg
5701 atggtttcta caaagatcgt tatgtttatc ggcacttgc atcggccgcg ctcccgattc
5761 cggaagtgct tgacattggg gaattcagcg agagcctgac ctattgcatc tcccgccgtg
```

Figure 21.
(Cont.)

```
5821 cacagggtgt cacgttgcaa gacctgcctg aaaccgaact gccgctgtt ctgcagcggg
5881 tcgcggaggc catggatgcg atcgctgcgg ccgatcttag ccagacgagc gggttcggcc
5941 cattcggacc gcaaggaatc ggtcaataca ctactgcg tgattcata tcgcgatty
6001 ctgatcccca tgtgtatcac tggcaaactg tgatggacga cacgtcagt gcgtccgtcg
6061 cgcaggatct cgatgagctg atgctttggg ccgaggactg ccccgaagtc cggcacctcg
6121 tgcacgcgga ttcggctcc aacaatgtcc tgacggacaa tggccgcata acagcggtca
6181 ttgactggag cgagcgcatc ttcgggatt cccaatacga ggtcgccaaa atcttcttct
6241 ggaggccgtg gttggcttgt atggagcagc agacgcgcta cttcgagcgg aggcatccgg
6301 agcttgcagg atcgcgcgg ctccgggcgt atatgctccg cattggtctt gaccaactct
6361 atcagagctt ggtgacggc aatttcgatg atgcagctty ggcgcaggt cgatgcgacg
6421 caatcgtccg atccggagcc gggactgtcg ggcgtacaca aatcgccgc agaagcgcgg
6481 ccggccgtct ggaccgatgg ctgtgtagaa gtactcgccg atagtgaaa ccgacgcccc
6541 agcactcgtc cggaccagc ttccttgtac aaagtggagt ccgcaaaaat caccagtctc
6601 tctctacaaa tctatctctc tctattttc tccagaatac tgtgtgagta gttcccagat
6661 aagggaatca ggttcttat aggqttcqc tcatqtqttq aqcatataaq aaaccctaq
6721 tatgtattg tatttgtaaa atacttctat caataaaatc tctaattcct aaaaccaaac
6781 tccaqtqacc tcaactttat tatacataqt tqataattca ctqqccqtqc ttattccatq
6841 gctgcaggtc gacgaattca ccggttaggg ataacagggt aatcgctacc ctaggacgt
6901 tatagttacg gccagtgcca ttaccctgtt atccctaacc ggtgacaact tgtatagaa
6961 aagttggttt gtgtcttcta gattaatcct tcaaactttt gattaaccaa aaaattata
7021 aaactaacat gttctccttt ttcttaga aattctaacg aattatctt tatactgatt
7081 tgaatatact taattggtc attggatgc cttacaac ctccttacca aactcactat
7141 ggcaaatata tactattttc cattgtacca taaatgtcca taattgaat taaattgtt
7201 gcagtacgaa accatccaac ttgtccaaa aacaaaatcc ttataacat ttactttaat
7261 gtaaatatat cctctactc tgttttaca accctagctc aaacaaattc attattgcg
7321 ataaaaatc atatcgaaca aactcgatga ttttcttttt cttacgttat taatgaaact
7381 aaaatataga aaaaaacaag atgaaccaaa ttttcaccta tctaactact taaatataat
7441 atgactaaat ttggtaaagt ttgaaaagtt tctttagaaa tgtgaaatat tgatcacgt
7501 ttctattgct aaaatcacca acaaacgca tgtcgccatt cataattatg gttcacacc
7561 tacaactagg ctaataagta aataagtaga caactagact caggtttgaa aaaaccataa
7621 aagccatata gcgttctc attgaactg cgaacacgat cgtgtgaatg ttgcagttc
7681 tagtttgat acaaacaaac aaaaacacaa tttaatctta gattaaaaag aaaaagaga
7741 acggagccca ctagccactc cttcaaacgt gtcttaacaa ctctcttcta gaaacaaatt
7801 aggcttcacc ttcatcttca aacctctctc tctctctatc tctcttttc tcaaaccatc
7861 tctctcataaa gccctaattt cttcatcaca agaatcagaa gaaygaacaa gtttgtacaa
7921 aaagcaggc ttactgcaaa aaacttatgg acctgcatct aatttttggt ccaacttgca
7981 caggaaagac gacgacgcg atagctcttg ccagcagac aggggcttca gtccttcgc
8041 ttgatcggt ccaatgctgt cctcaactat caaccggag cggacgacca acagtggaag
8101 aactgaaagg aacgacgcgt ctctccattg atgatcggcc tctggtggag ggtatcatcg
8161 cagccaagca agctcatcat aggctgatcg aggaggtgta taatcatgag gccaacggcg
8221 ggcttattct tgagggagga tccaactcgt tgctcaactg catgcgcga aacagctatt
8281 ggagtgcaga ttttcgttgg catattattc gccacaagtt accgaccaa gagaccttca
8341 tgaaagcggc caaggccaga gttaagcaga tgttgcaccc cgctgcagga cattctatta
8401 ttcaagagtt ggttatctt tggaatgaac atcggctgag gccaattctg aaagagatcg
8461 atggataccg atatgccatg ttgtttgcta gccagaacca gatcacggca gatatgctat
8521 tgcagcttga cgcaaatatg gaaggcaagt tgattaatgg gatcgctcag gagtatttca
8581 tccatgcgcg ccaacaggaa cagaaattcc ccaagttaa cgcagcgct tcgacggat
8641 tcgaaggtca tcgttcgga atgtattagg taccagctt tcttgtacaa agtggatcg
8701 ttcaaacatt tggcaataaa gtttcttaag attgaatcct gttgccggtc ttgcgatgat
```

Figure 21.
(Cont.)

```
8761 tatcatataa tttctgttga attacgttaa gcatgtaata attaacatgt aatgcatgac
8821 gttatttatg agatgggttt ttatgattag agtcccgcaa ttatacattt aatacgcgat
8881 agaaaacaaa atatagcgcg caaactagga taaattatcg cgcgcggtgt catctatgtt
8941 actagatcta actttattat acatagttga ttcgtcgacc tgcagtcgct acttaggac
9001 cgttatagtt atggcaaaca gctattatgg gtattatggg tggttcttta tgcggacatt
9061 gacggcttta tgcctgcagg tgcgagcga tgcggtacc gccgggcgt cgacaggcct
9121 aagcttagct tgagcttgga tcagattgtc gtttcccgcc ttcagtttaa actatcagtg
9181 tttgacaggga tatattggcg ggtaaaccta agagaaaaga gcgtttatta gaataacgga
9241 tatttaaaag ggcgtgaaaa ggtttatccg ttcgtccatt tgtatgtgca tgcaaccac
9301 agggttcccc tcgggatcaa agtactttga tccaaccgct ccgctgctat agtgcagtcg
9361 gcttctgacg ttcagtgcag ccgtcttctg aaaacgacat gtcgcacaag tcctaagtta
9421 cgcgacagga tgccgcctg ccttttcct ggcgttttct tgtcgcgtgt tttagtcgca
9481 taaagtagaa tacttgcgac tagaaccgga gacattacgc catgaacaag agcgacgcg
9541 ctggcctgct gggctatgcc cgcgtcagca ccgacgacca ggacttgacc aaccaacggg
9601 ccgaactgca cgcggccggc tgcaccaagc tgttttccga gaagatcacc ggcaccaggc
9661 gcgaccgccc ggagctggcc aggatgcttg accacctacg ccctggcgac gttgtgacag
9721 tgaccaggct agaccgcctg gcccgcagca cccgcgacct actggacatt gccgagcgca
9781 tccaggagge cggcgcggc ctgcgtagcc tggcagagcc gtgggccgac accaccacgc
9841 cggccggccg catggtgttg accgtgttcg ccggcattgc cgagttcgag cgttccctaa
9901 tcatcgaccg cacccggagc gggcgcgagg cgccaaggc ccgaggcgtg aagtttggcc
9961 ccgccctac cctcaccccg gcacagatcg cgcacgccg cgagtgatc gacaggaag
10021 gcgcacacgt gaaagaggcg gctgcactgg ttggcgtgca tgctcgacc ctgtaccgcg
10081 cacttgagcg cagcgaggaa gtgacgccca ccgaggccag gcggcgcggt gccttccgtg
10141 aggacgcatt gaccgaggcc gacgccctgg cggccgcga gaatgaacgc caagaggaa
10201 aagcatgaaa ccgcaccagg acggccagga cgaaccgttt tcattaccg aagagatcga
10261 ggcggagatg atcgcggccg ggtacgtgtt cgagccgcc gcgcacgtct caacgtgcg
10321 gctgcatgaa atcctggccg gtttgtctga tgccaagctg gcggcctgga cggccagct
10381 gcccgctgaa gaaacgagc gccgccgtct aaaaggtga tgtgtatttg agtaaaacag
10441 cttgcgtcat gcggtcgctg cgtatatgat gcgatgagta aataaacaaa tacgcaaggg
10501 gaacgcatga aggttatcgc tgtacttaac cagaaaggcg ggtcaggcaa gacgaccatc
10561 gcaaccatc tagcccgcgc cctgcaactc gccggggcg atgttctgtt agtcgattcc
10621 gatccccagg gcagtgcccg cgattgggcg gccgtgcggg aagatcaacc gctaaccgtt
10681 gtcggcatcg accgcccgac gattgaccgc gacgtgaagg ccatcggccg gcgcgacttc
10741 gtagtgatcg acggagcgcc ccaggcggcg gacttggctg tgtccgcgat caaggcagcc
10801 gacttcgtgc tgattccggt gcagccaagc ccttacgaca tatgggccac cgccgacctg
10861 gtggagctgg ttaagcagcg cattgaggtc acggatggaa ggctacaaga ggcttttgtc
10921 gtgtcgcggg cgatcaaagg cacgcgcatc ggcggtgagg ttgccgaggc gctggcccgg
10981 tacgagctgc ccattcttga
```

```
2701 caatgccgct tsccggatac ctgtccgcct ttctccttc gggaagcgtg gcgctttctc
2761 atagctcacg ctgtaggtat ctcagttcgg tgtaggtcgt tcgctccaag ctgggctgtg
2821 tgcacgaacc cccgttcag ccgaccgct gccttatc cgtaactat cgtcttgagt
2881 ccaacccggt aagacacgac ttatcgccac tggcagcagc cactggtaac aggattagca
2941 gagcgaggta tgtaggcggt gctacagagt tcttgaagtg gtggcctaac tacggctaca
3001 ctagaaggac agtatttggt atctgcgctc tgctgaagcc agttacctt ggaaaagag
3061 tggtagctc ttgatccggc aaacaaacca ccgctggtag cggtggtttt tttgttgca
3121 agcagcagat tacgcgcaga aaaaaggat ctcaagaaga tcctttgatc ttttctacgg
3181 ggtctgacgc tcagtggaac gaaaactcac gttaagggat tttggtcatg catgatatat
3241 ctcccaattt gtgtagggct tattatgcac gcttaaaaat aataaagca gactgacct
3301 gatagtttgg ctgtgagcaa ttatgtgctt agtgcatcta tcgcttgag ttaacgcgg
3361 cgaagcggcg tcggcttgaa cgaatttcta gctgacatt attgcgac tcacttggtg
3421 atctcgctt tcacgtagtg gacaaattct tccaactgat ctgcgcgcga ggccaagcga
3481 tcttctcctt gtccaagata gcctgtcta gttcaagta tgacgggctg atactgggcc
3541 ggcaggcgct ccattgccca gtcggcagcg acatcctcg gcgcgatttt gccggttact
3601 gcgctgtacc aaatgcggga cacgtaaga actacattc gctcatcgcc agcccagtcg
3661 ggcggcgagt tccatagcgt taaggtttca tttagcgcct caaatagatc ctgttcagga
3721 accggatcaa agagttcctc cgccgctgga cctaccaagg caacgctatg ttctattgct
3781 tttgtcagca agatagccag atcaatgtcg atcgtggctg gctcgaagat acctgcaaga
3841 atgtcattgc gctgccattc tccaaattgc agttcgcgct tagctggata acgccacgga
3901 atgatgtcgt cgtgcacaac aatggtgact tctacagcgc ggagaatctc gctctctcca
3961 ggggaagccg aagtttccaa aaggtcgttg atcaaagctc gccgcgttgt ttcatcaagc
4021 cttacggtca ccgtaaccag caaatcaata tcactgtgtg gcttcaggcc gccatccact
4081 gcggagccgt acaaatgtac ggccagcaac gtcggttcga tggcgctc gatgacgcca
4141 actacctctg atagttgagt cgatacttcg gcgatcaccg cttccccat gatgtttaac
4201 tttgttttag ggcgactgcc ctgctgcgta acatcgttgc tgctccataa catcaaacat
4261 cgacccacgg cgtaacgcgc ttgctgcttg gatgcccgag gcatagactg taccccaaaa
4321 aaacatgtca tcaacgaag ccatgaaaac cgccactgcg ccgttaccac cgctgcgttc
4381 ggtcaaggtt ctggaccagt tgcgtgacgg cagttacgct acttgcatta cagcttacga
4441 accgaacgag gcttatgtcc actgggttcg tgccgaatt gatcacaggc agcaacgctc
4501 tgtcatcgtt acaatcaaca tgctacccta cgagagatca tccgtgttca aaccggcgca
4561 gttagttgc cgttcttccg aatagcatcg gtaacatgag caaagtcgc cgcttacaa
4621 cggctctccc gctgacgccg tcccggactg atgggctgcc tgtatcgagt ggtgattttg
4681 tgccgagctg ccgtccggag agctgttggc tggctggtgg caggatatat tgtggtgtaa
4741 acaaattgac gcttagacaa ttaataaca cactgggga ttttttaatg tactgaatta
4801 acgcgaatt gaattcctcg agtacgtagg atccatttaa attctagagg cgcgcgata
4861 tcctctctta aggtagcgag ctcttaatta ataggataa cagggtaatg cggccgcaag
4921 ctaaaacgac ggccagtgaa ttatcaactt gtatagaaa agttgctctg ccgacagtgg
4981 tcccaagat ggaccccac ccncgaggag catgtggaa aagaagacg ttccaaccac
5041 gtcttcaaag caagtggatt gatgtgataa catggtggag cacgacactc tgtctactc
5101 caagaatatc aaagatacag tctcagaaga ccaaagggct attgagactt ttaacaaag
5161 ggtaatatcg ggaaacctcc tcggattcca ttgcccagct atctgtcact tcatcaaaag
5221 gacagtagaa aaggaaggtg gcacctacaa atgccatcat tgcgataaag gaaaggctat
5281 cgttcaagat gcctctgccg acagtggtcc caagatggac ccccacccga ggagcat
5341 cgtggaaaaa gaagacgttc caaccacgtc ttcaaagcaa gtggattgat gtgatatctc
```

Figure 23.
(Cont.)

```
5401 cactgacgta agggatgacg cacaatccca ctatccttcg caagacccct cctctatata
5461 aggaagttca tttcatttgg agaggacacg ctgcaagttt gtacaaaaaa gcaggctaga
5521 acgggggca atgagatatg aaaagcctg aactcacgc gacgtctgtc gagagtttc
5581 tgatcgaaaa gttcgacagc gtcctccgacc tgatycagct ctcggagggc gaagaatctc
5641 gtgtttcag cttcgatgta ggagggcgtg gatatgcct gcgggtaaat agctgcgcg
5701 atggtttcta caaagatcgt tatgtttatc ggcacttctgc atggccgcg ctccgattc
5761 cggaagtgct tgacattggg gaattagcg agagcctgac ctattgcatc tccgccgtg
5821 cacagggtgt cacgttgcaa gacctgcctg aaacgaact gccgcgtgtt ctgcagcgg
5881 tcgcggaggc catggatgcg atcgctgcgg ccgatcttag ccagacgagc gggttcggcc
5941 cattcggaca gaaggaatc ggtcaatgaca ctacatggcg tgatttcata tgcgcgattg
6001 ctgatcccca tgtgtatac tggcaaactg tgatggacga cacgtcagt gcgtcgtcg
6061 cgcaggctct cgatgagctg atgctttggg ccgaggactg ccccgaagtc cggcacctg
6121 tgcacgcgga tttcggctcc aacaatgtcc tgacggacaa tggccgcata acagcgtca
6181 ttgactgcag cgaggcgatg ttcgggtatt cccaatacga ggtcgccaac atcttcttc
6241 gaaggccgtg gttggcttgt atggagcagc agacgcgcta cttcgagcgg aggcatccgg
6301 agcttgcagg atcgccgcgg ctccgggcgt atatgatcg cattggtctt gaccacctct
6361 atcagagctt ggttgacggc aattcgatg atgcagcttg gcgcagggt cgatgcgacg
6421 caatcgtcg atccggagcc gggactgtcg ggcgtacaca aatcgcccgca gaagcgcgg
6481 ccggccgcct ggacgatgg ctgtgtagaa gtactgcgcg atagtggaaa ccgacgccc
6541 agcactgtc cggaccagc cttcttgtac aaagtggagt ccgcaaaaat caccagtctc
6601 tctctacaaa tctatctctc tctattttc tccagaataa tgtgtgagta gttccagat
6661 aagggaatta gggttcttat agggtttcgc tcatgtgtg agcatataag aaaccttag
6721 tatgtatttg tatttgtaaa atacttctat caataaaatt tctaattctc aaaccaaaa
6781 tccagtgacc tcaactttat tatacatagt tgataattca ctggccgtgc ttattccatg
6841 gctgcaggtc gacgaattca ccgttagg ataacagggt aataactata acggtcctaa
6901 ggtagcgagc ggccgcaagc taaaacgacg gccagtgaat tatcaacttt gtatagaaaa
6961 gttggttgt gttctctaga tttaatcctcc aaacttttga tttaccaaaa aaattatcaa
7021 actaacatgt tctctttttt tctttagaaa ttctaacgaa tttatcttca tactgatttg
7081 aatatactta atttggtcat ctggatgccc tttacaacct cctaccaaa atattgatca
7141 cagtttctat tgctaaaatc accaacaaaa cgcatgtcgc cattcataat tatggttca
7201 cacctacasc taggctaata agtaaataag tagacaacta gactcaggtt tgaaaaacc
7261 ataaaagcca tatagcgttt tctcattgaa actgcgaaca cgatgtgtg aatgttgcag
7321 tttctagtt tgatacaaac aaacaaaaac acaattaat cttagattaa aagagaaaa
7381 gagaacggag cccactagca actcctcca acgtgtctta ccaactctct tctagaaaca
7441 aattaggctt cacctcctc tttccaacctc tctctctctc tctctctctt ttctcaaac
7501 catctctcca taagccctaa atttcttcat cacaagaatc agaagaagaa acaagtttgt
7561 acaaaaaagc aggcttactg caaaaaaact atggaccctgc gtctaatttt cggtccaact
7621 tgcacaggaa agacgacgac cgcgtagct cttgccccagc agacagggct tcagtcctt
7681 tcgcttgatc gggtccaatg ctgtcctcaa ctatcaaccg gaagcggacg accaacagtg
7741 gaagaactga aggaacgac gcgtctctca cttgatgatc ggcctctggt ggagggtatc
7801 atgcagcca agcaagtca tcataggctg atcgaggagg tgtataatca tgaggccaac
7861 ggcggggctta tcttgaggg aggatccacc cgttgctca actgcatggc gcgaacagc
7921 tattggagtg cagattttcg tttggtatatt attcgccaca agttacccga ccaagagacc
7981 ttcatgaaag cggccaaggc cagagttaag caggatgttgc acccgctgc aggccattct
8041 attattcaag agttggttta tctttggaat gaacctaggc tgaggccccat tctgaagag
```

Figure 23.
(Cont.)

```
8101 atcgatggat atcgtatgc catgttgttt gctagccaga accagattac ggcagatatg
8161 ctattgcagc ttgacgcaaa tatgaaggt aagttgatta atgggatcgt tcaggagtat
8221 ttcatccatg cgcgccaaca ggaacagaaa ttccccccaag ttaacgcaga cgctttcgac
8281 ggattcgaag gtcatccgtt cggaatgtat gaggtaccca gctttcttgt acaaagtggg
8341 atcgttcaaa cattggcaa taaagttcr taagattgaa tcctgttgcc ggtcttgcga
8401 tgattatcat ataatttctg ttgaattacg ttaagcatgt aataattaac atgtaatgca
8461 cgacgttatt tatgagatgg gtttttacga ttagagtccc gcaattatac atttaatacg
8521 cgatagaaaa caaaatatag cgcgcaaact aggataaatt atcgcgcgcg gtgtcatcta
8581 tgttactaga tccaactta ttatacaatag ttgataattc actggccgtc gcttattcca
8641 tggctgcagg tcgacgaatt caccggtaa ctataacggt cctaaggtag cgatggcaaa
8701 cagctattat gggtattatg ggtggttctt tatgcggaca ctgacggctt tatgcctgca
8761 gtcgcgagc gatgcggta ccgcgggc gtcgacaggc ctaagcttag cttgagcttg
8821 gatcagattg tcgttcccg ccttcagttt aasctatcag tgtttgacag gatatattgg
8881 cgggtaaacc taagagaaaa gagcgtttat tagaataacg gatatttaaa aggcgtgaa
8941 aaggtttatc cgttcgtcca tttgtatgtg catgccaacc acagggttcc cctcgggatc
9001 aaagtacttt gatccaaccc ctccgctgct atagtgcagt cggcttctga cgttcagtgc
9061 agccgttctc tgaaaacgac atgtcgcaca agtcctaagt tacgcgacag gctgcgcgcc
9121 tgccctttc ctggcgtttt cttgtcgcgt gttttagttg catasagtag aatacttgcg
9181 actagaaccg gagacattac gccatgaaca agagcgccgc cgctggcctg ctgggctatg
9241 cccgcgtcag caacgacgac caggactgga ccaaccaacg ggccgaactg cacgcggccg
9301 gctgcaccaa gctgttttcc gagaagatca ccggcaccag gcgcgaccgc ccggagctgg
9361 ccaggatgct tgaccacctg cgccctggcg acgttgtgac agtgaccagg ctagacgcc
9421 tggcccgcag cacccgcgac ctactggaca ttgccgagcg catccaggag gccggcgcgg
9481 gcctgcgtag cctggcagag ccgtgggccg acaaccacac gccggccggc cgcatggtgt
9541 tgaccgtgtt cgccggcatt gccgagttcg agcgttccct aatcatcgac cgcacccgga
9601 gcgggcgcga ggccgccaag gcccgaggcg tgaagtttgg cccccgccct accctcaccc
9661 cggcacagat cgcgcacgcc cgcgagctga tcgaccagga aggccgcacc gtgaaagagg
9721 cggctgcact gcttggcgtg catgctcga ccctgtaccg cgacttgag cgcagcgagg
9781 aagtgacgcc cacgaggcc aggcggcgcg gtgccttccg tgaggacgca ttgaccgagg
9841 ccgacgccct ggcggccgcc gagaatgaac gccaagagga acaagcatga aaccgcacca
9901 ggacggccag gacgaaccgt ttttcattac cgaagagatc gaggcggaga tgatcgcggc
9961 cgggtacgtg ttcgagccgc ccgcgcacgt ctcaaccgtg cggctgcatg aaatcctggc
10021 cggtttgtct gatgccaagc tggcggcctg gccggccagc ttggccgctg aagaaaccga
10081 gcgccgccgt ctaaaaggt gatgtgtatt tgagtaaaac agcttgcgtc atgcggtcgc
10141 tgcgtatatg atgcgatgag taaataaaca aatacgcaag gggaacgcat gaaggttatc
10201 gctgtactta accagaaagg cgggtcaggc aagacgacca tcgcaaccca tctagcccgc
10261 gccctgcaac tcgccggggc cgatgttctg ttagtcgatt ccgatcccca gggcagtgcc
10321 cgcgattggg cggccgtgcg ggaagatcaa ccgctaaccg ttgtcggcat cgaccgcccg
10381 acgattgacc gcgacgtgaa ggccatcggc cggcgcgact tgtagtgat cgacggagcg
10441 ccccaggcgg cggacttggc tgtgtccgcg atcaaggcag ccgacttcgt gctgattccg
10501 gtgcagccaa gcccttacga catatgggcc accgccgacc tggtggagct ggttaagcag
10561 cgcattgagg tcacggatgg aaggctacaa aggcctttg tcgtcgcg ggcgatcaaa
10621 ggcacgcgca tcggcggtga ggttgccgag gcgctggccg ggtacgagct gcccattctt
10681 ga
```

```
5401 aatagagttt tagttttctt aatttagagg ctaaaataga ataaaataga tgtactaaaa
5461 aaattagtct ataaaaacca ttaaccctaa accctaaatg gatgtactaa taaaatggat
5521 gaagtattat ataggtgaag ctatttgcaa aaaaaagga gaacacatgc acactaaaaa
5581 gataaaactg tagagtcctg ttgtcaaaat actcaattgt ccttttagacc atgtctaact
5641 gttcatttat atgattctct aaaacactga tattattgta gtactataga ttattatt
5701 cgtagagtaa agtttaaata tatgtataaa gatgataaa ctgcacttca aacaagtgtg
5761 acaaaaaaaa tatgtggtaa tttttttataa cttagacatg caatgctcat tatctctaga
5821 gaggggcacg acgggtcac gctgcactgc aggcatgcaa gcttgaattc ctgcagccc
5881 gccaagctat caacttgta tagaaagtt ggtttgtgtc ttctagatta atcctccaaa
5941 cttttgatta aacaaaaaaa ttatcaaact aacatgttct ccttttttct ttagaaattc
6001 taacgaattt atcttatac tgatttgaat atacttaatt tggtcatttg gatgcctttt
6061 acaacctcct taccaaactc actatggaaa atatatacta tttccattg taacataaat
6121 gtccatcatt tgaattaaat tcgttgcagt acgaaaccat ccaactttgt ccaaaaacaa
6181 aatccttata actattact ttaatgtaaa tatatcctct acttttgttt ttacaaccct
6241 agctcaaaca aatttattct ttgcgataaaa aaatcatatc gaacaaactc gatgattttt
6301 tttttcttac gttattaatg aaactaaaat atagaaaaaa acaagatgaa ccaaatttc
6361 acctatctaa ctacttaaat ataatatgat taaatttggt aaagtttgaa aagttctt
6421 agaaatgtga aatattgatc acagtttcta ttgctaaaaat caccaacaaa acgcatgtcg
6481 ccattcataa ttatggtttc acacctacaa ctaggctaat aagtaaataa gtagacaact
6541 agactcaggt ttgaaaaaac catagagcc atatagcgtt ttctcattga aactgcgaac
6601 acgatcgtgt gaatgctgca gtttctagtt ttgatacaaa caaacaaaaa cacaatttaa
6661 tcttagatta aaagaaaaa agagaacgga gcccactagc cactccttca aacgtgtctt
6721 accaactctc ttctagaaac aaattaggct tcaccttcct cttccaacct ctctctctct
6781 ctctctctgt ttttctcaaa ccatctatcc ataaaagcct aatttcttca tcacaagaat
6841 cagaagaaga aacaagtttg tacaaaaaag caggcttact gcaaaaaact tatggaactg
6901 catctaattt tcggtccaac ttgcacagga aagacgacga acgcgatagc tcttgccag
6961 cagacaggc ttccagtcct ttcgattgat cgggtccaat gctgtcctca actatcaacc
7021 ggaagcggac gaccaacagt ggaagaactg aaaggaacga cgcgtctcta ccttgatgat
7081 cggcctctgg tggagggtat catcgcagcc aagcaagctc atcataggct gatcgaggag
7141 gtgtataatc atgaggccaa cggcgggctt attcttgagg gaggatccac ctcgttgatc
7201 aactgcatgg cgcgaaacag ctattggagt gcagattttc gttggcatat tattcgcacc
7261 aagttacccg accaagagac cttcatgaaa gcggccaagg ccagagttaa gcagatgttg
7321 caccccgctg caggccattc tattattcaa gagttggttt atctttggaa tgaacctcgg
7381 ctgaggccca ttctgaaaga gatcgatgga tatcgatatg ccatgttgtt tgctagccag
7441 aaccagatca cggcagatat gctattgcag cttgacgcaa atatggaagg taagttgatt
7501 aatgggatcg ctcaggagta tttcatccat gcgcgacaac aggaacagaa attcccccaa
7561 gttaacgcag ccgttttcga cggattcgaa ggtcatccgt tcggaatgta ttaggtaccc
7621 agcttcttg tacaaagtgg agtccgcaaa aatcaccagt ctctctctac aaatctatct
7681 ctctctattt ttctccagaa taatgtgta gtagttccca gataagggaa ttagggttct
7741 tatagggttt cgctcatgtg ttgagcatat aagaaaccct tagtatgtat ttgtatttgt
7801 aaaatacttc tatcaataaa atttctaatt cctaaaaccaa aaatccagtg acctcaactt
7861 ta
```

Figure 25.
(Cont.)

A.
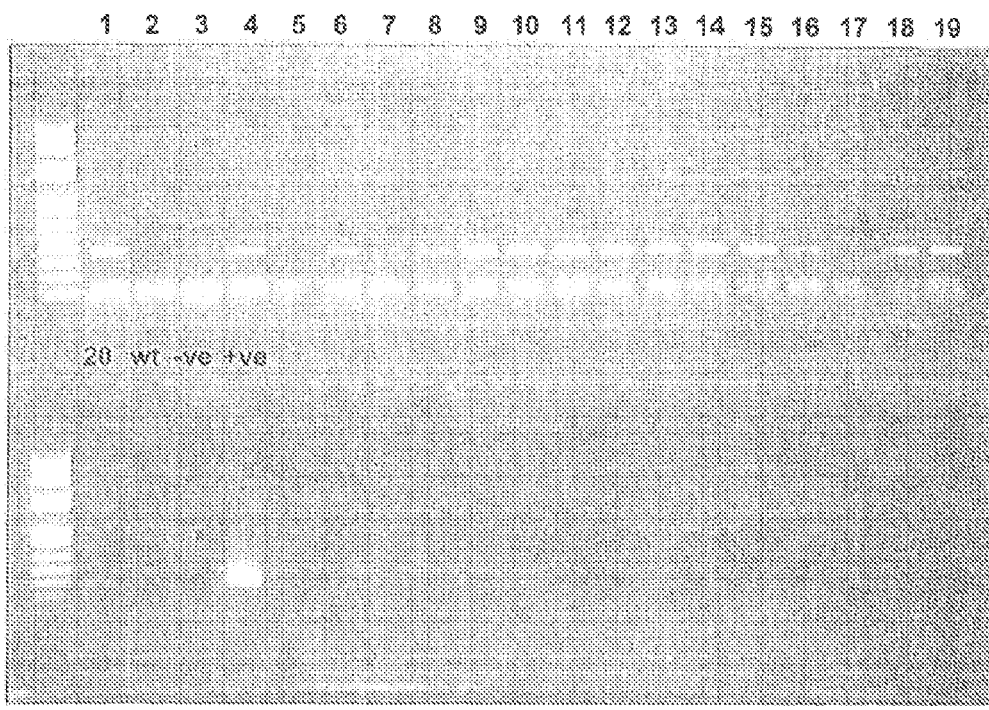
B.
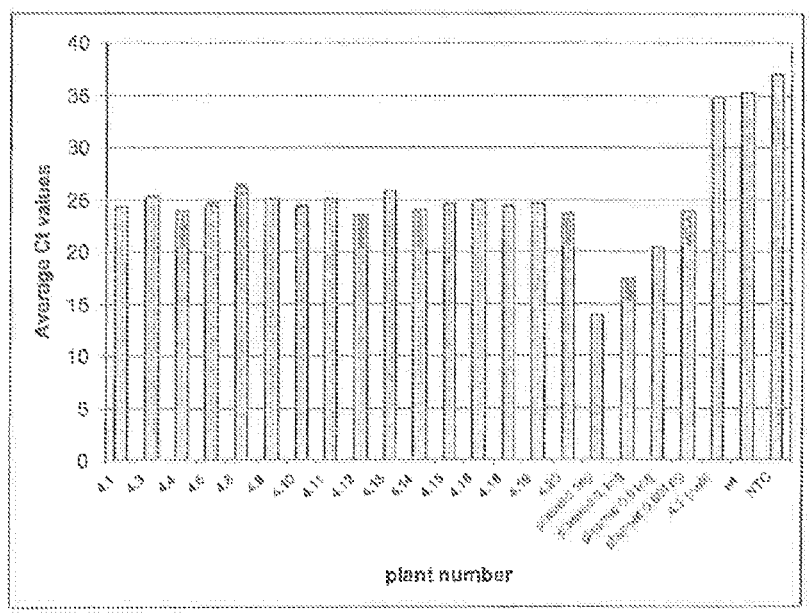
Figure 36

MANIPULATION OF PLANT SENESCENCE USING MODIFIED PROMOTERS

CROSS-REFERENCE TO RELATED APPLICATIONS

This application is a continuation of U.S. patent application Ser. No. 12/605,214, filed Oct. 23, 2009, issued as U.S. Pat. No. 8,399,739, which is a continuation-in-part of U.S. patent application Ser. No. 11/789,526, filed Apr. 24, 2007, now abandoned, and which is also a continuation-in-part of International Patent Application No. PCT/AU2008/000566, filed Apr. 21, 2008. The contents of the foregoing are hereby incorporated herein by reference in their entireties.

STATEMENT REGARDING SEQUENCE LISTING

The sequence listing associated with this application is provided in text format in lieu of a paper copy and is hereby incorporated by reference into the specification. The name of the text file containing the sequence listing is 40774_Sequence_Final_2013-02-26.txt. The text file is 80 KB; was created on Feb. 26, 2013; and is being submitted via EFS-Web with the filing of the specification.

BACKGROUND

The present invention relates to methods of manipulating senescence in plants. The invention also relates to vectors useful in such methods, transformed plants with modified senescence characteristics and plant cells, seeds and other parts of such plants.

Leaf senescence involves metabolic and structural changes in cells prior to cell death. It also involves the recycling of nutrients to actively growing regions.

The regulation of plant and plant organ senescence by cytokinins has important agricultural consequences. Elevated cytokinin levels in leaves tend to retard senescence. A number of promoters have been used to regulate the expression of the ipt gene, whose product (isopentenyltransferase) catalyses a key step in cytokinin synthesis. However, in general, transgenic plants over-expressing the ipt gene have been reported to have retarded root and shoot growth, no root formation, reduced apical dominance, and reduced leaf area.

It is an object of the present invention to overcome, or at least alleviate, one or more of the difficulties or deficiencies associated with the prior art.

In one aspect, the present invention provides a method of manipulating senescence in a plant, said method including introducing into said plant a genetic construct including a modified myb gene promoter, or a functionally active fragment or variant thereof, operatively linked to a gene encoding an enzyme involved in biosynthesis of a cytokinin, or a functionally active fragment or variant thereof.

The manipulation of senescence relates to the plant and/or specific plant organs. Senescence of different plant organs, such as leaves, roots, shoots, stems, tubers, flowers, stolons, and fruits may be manipulated. The manipulation of plant and plant organ senescence may have important agricultural consequences, such as increased shelf life of e.g., fruits, flowers, leaves and tubers in horticultural produce and cut flowers, reduced perishability of horticultural crops, increased carbon fixation in senescence-retarded leaves leading to enhanced yields, enhanced biomass production in forage plants, enhanced seed production, etc.

"Manipulating senescence" generally relates to delaying senescence in the transformed plant relative to an untransformed control plant. However, for some applications it may be desirable to promote or otherwise modify senescence in the plant. Senescence may be promoted or otherwise modified for example, by utilizing an antisense gene.

An effective amount of said genetic construct may be introduced into said plant, by any suitable technique, for example by transduction, transfection or transformation. By "an effective amount" is meant an amount sufficient to result in an identifiable phenotypic trait in said plant, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

By a "modified myb gene promoter" is meant a promoter normally associated with a myb gene, which promoter is modified to delete or inactivate one or more root specific motifs and/or pollen specific motifs in said promoter.

While applicant does not wish to be restricted by theory, it is postulated that deletion or inactivation of one or more root specific motifs in said myb gene promoter may alleviate or overcome the problem of leaky expression of the gene encoding a cytokinin biosynthetic enzyme in plant meristems, which may affect root development in some species of plants. It is also postulated that deletion or inactivation of one or more pollen specific motifs in said myb gene promoter may alleviate or overcome the problem of leaky expression of the gene encoding a cytokinin biosynthetic enzyme in pollen, which may affect pollen development in some species of plants.

Preferably the modified myb gene promoter is a modified myb32 gene promoter. Preferably the modified myb gene promoter is from *Arabidopsis*, more preferably *Arabidopsis thaliana*.

A suitable promoter which may be modified according to the present invention is described in Li et al., Cloning of three MYB-like genes from *Arabidopsis* (PGR 99-138) Plant Physiology 121:313 (1999), the entire disclosure of which is incorporated herein by reference.

By a "root specific motif" is meant a sequence of 3-7 nucleotides, preferably 4-6 nucleotides, more preferably 5 nucleotides, which directs expression of an associated gene in the roots of a plant.

Preferably the root specific motif includes a consensus sequence ATATT or AATAT.

Preferably, between one and ten, more preferably between three and eight, even more preferably between five and seven root specific motifs are deleted or inactivated, preferably deleted, in said myb gene promoter.

The root specific motifs may be deleted by removing individual motifs or by removing a fragment of the promoter containing one or more motifs. For example, all or part of the region between nucleotides 1 and 530, preferably between nucleotides 110 and 530 of the *Arabidopsis thaliana* myb gene promoter may be deleted.

The deletion may be effected by cutting the nucleic acid, for example with restriction endonucleases, and ligating the cut ends to generate a promoter with a fragment removed.

For example, a modified *Arabidopsis thaliana* myb gene promoter may be prepared by removing a fragment between the Xcm1 site at positions 162-176 and the SspI site at positions 520-525. This generates a modified myb gene promoter with 6 of the 7 root specific motifs deleted. Alternatively, all 7 of the root specific motifs may be deleted, for example by deleting the region upstream of the SspI site at positions 520-525, or by deleting the region between nucleotides 1 and 120 together with the region between the XcmI site at positions 162-176 and the SspI site at positions 520-525.

A root specific motif may be inactivated by adding, deleting, substituting or derivatizing one or more nucleotides within the motif, so that it no longer has the preferred consensus sequence.

Preferably the modified myb gene promoter includes a nucleotide sequence selected from the group consisting of the sequences shown in FIGS. 2, 3 and 4 hereto (Sequence ID Nos: 2, 3 and 4, respectively) and functionally active fragments and variants thereof.

By a "pollen specific motif" is meant a sequence of 3-7 nucleotides, preferably 4-6 nucleotides, more preferably 4 or 5 nucleotides, which directs expression of an associated gene in the pollen of a plant.

Preferably the pollen specific motif includes a consensus sequence selected from the group consisting of TTCT and AGAA.

Preferably, between one and thirty, more preferably between three and fifteen, even more preferably between four and ten pollen specific motifs are deleted or inactivated, preferably deleted, in said myb gene promoter.

The pollen specific motifs may be deleted by removing individual motifs or by removing a fragment of the promoter containing one or more motifs. For example, all or part of the region between nucleotides 1 and 540, preferably between nucleotides 390 and 540 of the *Arabidopsis thaliana* myb gene promoter may be deleted.

The deletion may be effected by cutting the nucleic acid, for example with restriction endonucleases, and ligating the cut ends to generate a promoter with a fragment removed.

For example, a modified *Arabidopsis thaliana* myb gene promoter may be prepared by removing a fragment between the XcmI site at positions 162-176 and the SspI site at positions 520-525. This generates a modified myb gene promoter with 4 of the 23 pollen specific motifs deleted. Alternatively, 10 of the pollen specific motifs may be deleted, for example by deleting the region upstream of the SspI site at positions 520-525.

A pollen specific motif may be inactivated by adding, deleting, substituting or derivatizing one or more nucleotides within the motif, so that it no longer has the preferred consensus sequence.

Preferably the modified myb gene promoter includes a nucleotide sequence selected from the group consisting of the sequences shown in FIGS. 2, 3 and 4 hereto (Sequence ID Nos: 2, 3 and 4, respectively) and functionally active fragments and variants thereof.

In a further aspect of the present invention there is provided a method of enhancing biomass in a plant, said method include introducing into said plant a genetic construct including a myb gene promoter, or a functionally active fragment or variant thereof, operatively linked to a gene encoding an enzyme involved in biosynthesis of a cytokinin, or a functionally active fragment or variant thereof.

The myb gene promoter or a functionally active fragment or variant thereof may be a full length myb gene promoter or a modified myb gene promoter.

The full length myb gene promoter may be a myb32 gene promoter. Preferably the myb gene promoter is from *Arabidopsis*, more preferably *Arabidopsis thaliana*. Most preferably the myb gene promoter includes a nucleotide sequence selected from the group consisting of the sequence shown in FIG. 1 hereto (Sequence ID No: 1) and functionally active fragments and variants thereof.

A suitable promoter is described in Li et al., Cloning of three MYB-like genes from *Arabidopsis* (PGR 99-138) Plant Physiology 121:313 (1999).

The modified myb gene promoter may be a modified myb gene promoter as hereinbefore described.

By "enhancing biomass" is meant enhancing or increasing in a transformed plant relative to an untransformed control plant a growth characteristic selected from the group consisting of total leaf area, cumulative leaf area, leaf growth dynamics (i.e., number of leaves over time), stolon length, percentage of flowering plants and seed yield per flower or per area sown. "Enhancing biomass" also includes reducing or decreasing percentage stolon death in a transformed plant relative to an untransformed control plant.

In particular, applicants have found that while the seed weight (i.e., weight of thousand seeds) of transgenic plants according to the present invention was indistinguishable from non-transgenic control plants, the total seed yield expressed on the basis of per flower or per area sown was significantly higher in the transgenic plants when compared with non-transgenic control plants of equivalent flowering intensity.

By "functionally active" in relation to a myb gene promoter or modified myb gene promoter is meant that the fragment or variant (such as an analogue, derivative or mutant) is capable of manipulating senescence in a plant by the method of the present invention. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence to which the fragment or variant corresponds, more preferably at least approximately 90% identity, most preferably at least approximately 95% identity. Preferably the fragment has a size of at least 20 nucleotides, more preferably at least 50 nucleotides, more preferably at least 100 nucleotides, more preferably at least 200 nucleotides, most preferably at least 300 nucleotides.

By a "gene encoding an enzyme involved in biosynthesis of a cytokinin" is meant a gene encoding an enzyme involved in the synthesis of cytokines such as kinetin, zeatin and benzyl adenine, for example a gene encoding isopentyl transferase (ipt), or an ipt-like gene such as the sho gene (eg. from petunia). Preferably the gene is an isopentenyl transferase (ipt) gene or sho gene. In a preferred embodiment, the gene is from a species selected from the group consisting of *Agrobacterium*, more preferably *Agrobacterium tumefaciens*; *Lotus*, more preferably *Lotus japonicus*; and *Petunia*, more preferably *Petunia hybrida*.

Most preferably the gene includes a nucleotide sequence selected from the group consisting of the sequences shown in FIGS. 6, 8 and 10 hereto (Sequence ID Nos: 5, 7 and 9) sequences encoding the polypeptides shown in FIGS. 7, 9 and 11 hereto (Sequence ID Nos: 6, 8 and 10), and functionally active fragments and variants thereof.

By "functionally active" in relation to a gene encoding a cytokinin biosynthetic enzyme is meant that the fragment or variant (such as an analogue, derivative or mutant) is capable of manipulating senescence in a plant by the method of the present invention. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence, to which the fragment or variant corresponds more preferably at least approximately 90% identity, most preferably at least approximately 95% identity. Such functionally active variants and fragments include, for example, those having conservative nucleic acid changes or nucleic acid changes which result in conservative amino acid substitutions of one or more residues in the corresponding amino acid sequence. For example, the functionally active variant may include one or more conservative nucleic acid substitutions of a sequence shown in FIG. 6, 8 or 10, the resulting functionally active variant encoding an amino acid sequence shown in FIG. 7, 9 or 11, respectively. Preferably the fragment has a size of at least 20 nucleotides, more preferably at least 50 nucleotides, more preferably at least 100 nucleotides, more preferably at least 500 nucleotides.

The genetic construct may be introduced into the plant by any suitable technique. Techniques for incorporating the genetic constructs of the present invention into plant cells (for example by transduction, transfection or transformation) are well known to those skilled in the art. Such techniques include *Agrobacterium* mediated introduction, electroporation to tissues, cells and protoplasts, protoplast fusion, injection into reproductive organs, injection into immature embryos and high velocity projectile introduction to cells, tissues, calli, immature and mature embryos, biolistic transformation and combinations thereof. The choice of technique will depend largely on the type of plant to be transformed, and may be readily determined by an appropriately skilled person.

Cells incorporating the genetic construct of the present invention may be selected, as described below, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

The methods of the present invention may be applied to a variety of plants, including monocotyledons [such as grasses (e.g., forage, turf and bioenergy grasses including perennial ryegrass, tall fescue, Italian ryegrass, red fescue, reed canary grass, big bluestem, cordgrass, napiergrass, wildrye, wild sugarcane, Miscanthus), corn, oat, wheat and barley)], dicotyledons [such as *Arabidopsis*, tobacco, soybean, clovers (e.g., white clover, red clover, subterranean clover), alfalfa, canola, vegetable brassicas, lettuce, spinach] and gymnosperms.

In a further aspect of the present invention there is provided a vector capable of manipulating senescence in a plant, said vector including a modified myb gene promoter, or a functionally active fragment or variant thereof, operatively linked to a gene encoding an enzyme involved in the biosynthesis of a cytokinin, or a functionally active fragment or variant thereof.

In a still further aspect of the present invention there is provided a vector capable of enhancing biomass in a plant, said vector including a myb gene promoter, or a functionally active fragment or variant thereof, operatively linked to a gene encoding an enzyme involved in the biosynthesis of a cytokinin, or a functionally active fragment or variant thereof.

The myb gene promoter or a functionally active fragment or variant thereof may be a full length myb gene promoter or a modified myb gene promoter, as described herein.

In a preferred embodiment of this aspect of the invention, the vector may further include a terminator; said promoter, gene and terminator being operably linked.

By "operably linked" is meant that said promoter is capable of causing expression of said gene in a plant cell and said terminator is capable of terminating expression of said gene in a plant cell. Preferably, said promoter is upstream of said gene and said terminator is downstream of said gene.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*; derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable or integrative or viable in the plant cell.

The promoter, gene and terminator may be of any suitable type and may be endogenous to the target plant cell or may be exogenous, provided that they are functional in the target plant cell.

A variety of terminators which may be employed in the vectors of the present invention are also well known to those skilled in the art. The terminator may be from the same gene as the promoter sequence or a different gene. Particularly suitable terminators are polyadenylation signals, such as the CaMV 35S polyA and other terminators from the nopaline synthase (nos) and the octopine synthase (ocs) genes.

The vector, in addition to the promoter, the gene and the terminator, may include further elements necessary for expression of the gene, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (nptII) gene, the hygromycin phosphotransferase (hph) gene, the phosphinothricin acetyltransferase (bar or pat) gene], and reporter genes (such as beta-glucuronidase (GUS) gene (gusA)]. The vector may also contain a ribosome binding site for translation initiation. The vector may also include appropriate sequences for amplifying expression.

As an alternative to use of a selectable marker gene to provide a phenotypic trait for selection of transformed host cells, the presence of the vector in transformed cells may be determined by other techniques well known in the art, such as PCR (polymerase chain reaction), Southern blot hybridisation analysis, histochemical assays (e.g., GUS assays), thin layer chromatography (TLC), northern and western blot hybridisation analyses.

Those skilled in the art will appreciate that the various components of the vector are operably linked, so as to result in expression of said gene. Techniques for operably linking the components of the vector of the present invention are well known to those skilled in the art. Such techniques include the use of linkers, such as synthetic linkers, for example including one or more restriction enzyme sites.

In a further aspect of the present invention there is provided a transgenic plant cell, plant, plant seed or other plant part, with modified senescence characteristics or enhanced biomass. Preferably said plant cell, plant, plant seed or other plant part includes a vector according to the present invention. Preferably the transgenic plant cell, plant, plant seed or other plant part is produced by a method according to the present invention.

The present invention also provides a transgenic plant, plant seed or other plant part derived from a plant cell of the present invention.

The present invention also provides a transgenic plant, plant seed or other plant part derived from a plant of the present invention.

The present invention will now be more fully described with reference to the accompanying examples and drawings. It should be understood, however, that the description following is illustrative only and should not be taken in any way as a restriction on the generality of the invention described above.

FIGURES

FIG. 1 shows the nucleotide sequence of the promoter from myb32 gene (atmyb32) from *Arabidopsis thaliana* (Sequence ID No: 1), Atmyb32 promoter sequence with MYB type, pollen specific and Root specific motifs highlighted. WAACCA (underline/italics) MYB1AT; GTTAGTT (bold/box) MYB1LEPR; CCWACC (box) MYBPZM; GGATA (italics) MYBST1; AGAAA (underline) POLLEN1LELAT52; ATAT (bold) ROOTMOTIFTAPOX1.

FIG. 2 shows an Atmyb32 promoter sequence variant (Atmyb32xs) with the XcmI-SspI plant sequence deleted. MYB type, pollen specific and Root specific motifs are highlighted. WAACCA (underline/italics) MYB1AT; GTTAGTT (bold/box) MYB1LEPR; CCWACC (box) MYBPZM; AGAAA (underline) POLLEN1LELAT52; ATATT (bold) ROOTMOTIFTAPOX1 (Sequence ID No: 2).

FIG. 3 shows an Atmyb32 promoter variant sequence with all root motifs deleted. MYB type, pollen specific and Root specific motifs are highlighted. WAACCA (underline/italics) MYB1AT; CCWACC (box) MYBPZM; AGAAA (underline) POLLEN1LELAT52 (Sequence ID No: 3).

FIG. 4 shows an Atmyb32 promoter variant sequence with the SspI site upstream sequence deleted. MYB type, pollen specific and Root specific motifs are highlighted. WAACCA (underline/italics) MYB1AT; CCWACC (box) MYBPZM; AGAAA (underline) POLLEN1LELAT52 (Sequence ID No: 4).

FIG. 6 shows the nucleotide sequence of the isopentenyl transferase (ipt) gene from *Agrobacterium tumefaciens* (Sequence ID No: 5).

FIG. 7 shows the deduced amino acid sequence of the isopentyl transferase gene from *Agrobacterium tumefaciens* (Sequence ID No. 6).

FIG. 8 shows the nucleotide sequence of the isopentyl transferase gene from *Lotus japonicus* (Sequence ID No. 7).

FIG. 9 shows the deduced amino acid sequence of the isopentyl transferase gene from *Lotus japonicus* (Sequence ID No. 8).

FIG. 10 shows the Nucleotide sequence of the cytokinin biosynthesis Sho gene from *Petunia hybrida* (Sequence ID No. 9).

FIG. 11 shows the Deduced amino acid sequence of the cytokinin biosynthesis Sho gene from *Petunia hybrida* (Sequence ID No. 10).

Figure 5:
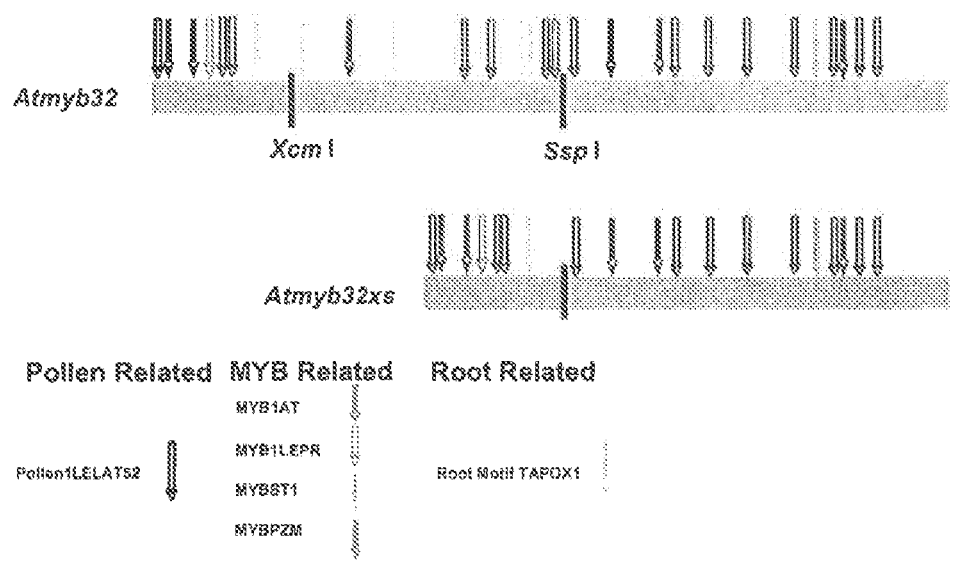
FIG. 5 shows Motifs in Atmyb32 and Atmyb32xs promoter sequences.
Figure 12:
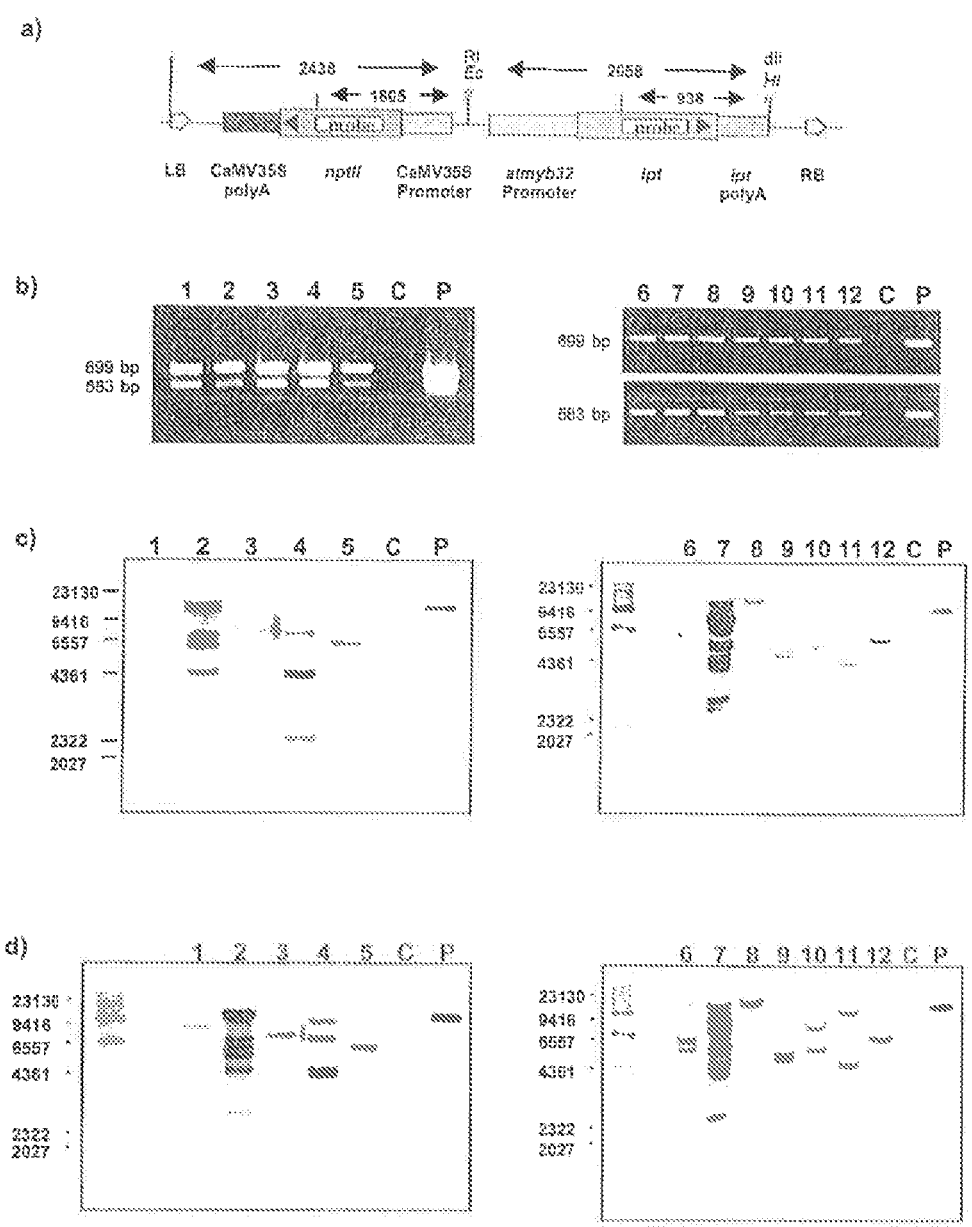

FIG. 12 shows PCR and Southern DNA analysis of atmyb32::ipt transgenic white clover (*Trifolium repens*) plants. a) The T-DNA region of patmyb32:ipt showing restriction enzyme sites and location of the probes used for Southern hybridization analysis. b) Ethidium bromide stained 1% agarose gel of the PCR amplified 599 bp nptII and 583 bp ipt products. c) Southern blot hybridization with HindIII digested total genomic DNA isolated from PCR positive white clover plants hybridized with the ipt probe. d) Southern blot hybridization with HindIII digested total genomic DNA isolated from PCR positive white clover plants hybridized with the nptII probe. Lanes 1-2: two independent kanamycin resistant cv. Haifa regenerants, code: Hmi01, Hmi08 respectively; Lanes 3-12: twelve independent kanamycin resistant cv. Irrigation regenerants, codes: Imi06, Imi07, Imi08, Imi09, Imi10, Imi11, Imi12, Imi14, Imi16, Imi18 respectively; Lane C: non-transformed white clover; Lane P: positive control plasmid patmyb32ipt.

Figure 13:
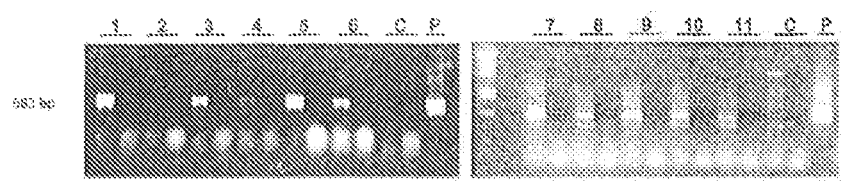

FIG. 13 shows RT-PCR analysis of ipt mRNA expression in atmyb32::ipt transgenic white clover (*T. repens*) plants. Lane 1-11 are samples from 11 independent transgenic lines with corresponding plant codes as in FIG. 4.8; Lane C, Control non-transformed plant; Lane P, plasmid as positive control. Total RNA was isolated from leaf tissues. Total RNA (13 μg) was used for each reverse transcription reaction and ⅕ of RT product was amplified by PCR. DNA products on the gel on the right were amplified by 2×30 cycles intensive PCR. No reverse transcriptase was added to the corresponding RT-PCR reaction loaded into alternate lanes.

Figure 14:
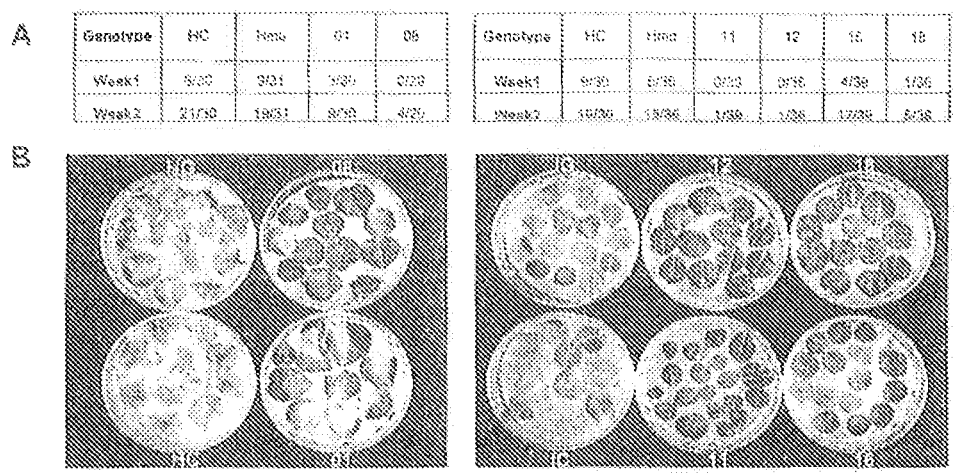

FIG. 14 shows a senescence bioassay of excised leaves from atmyb32::ipt transgenic white clover (*T. repens*) plants. At least 30 leaves were collected from each line from similar positions on stolons of plant lines. A. The number of yellowing leaves as a fraction of the total number of excised leaves. B. Typical appearance of leaves kept on water under light for two weeks. Key to plant lines: HC, IC and Hmg, Img, non-transformed and atmyb32::gusA transgenic plants (cv. Haifa and Irrigation) respectively; 01 and 08, atmyb32::ipt transgenic Haifa lines Hmi01 and Hmi08 respectively; 11, 12, 16 and 18 atmyb32::ipt transgenic Irrigation lines Imi11, Imi12, Imi16 and Imi18 respectively.

Figure 15:
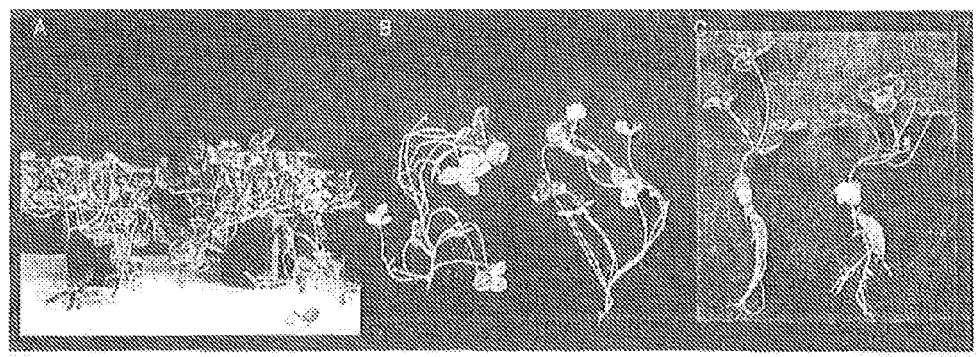

FIG. 15 shows A) General plant morphology, B) Normal shoot development, and C) Normal root development in atmyb32::ipt transgenic white clover (*T. repens*) (right) plants compared to control plants (left).

Figure 16:
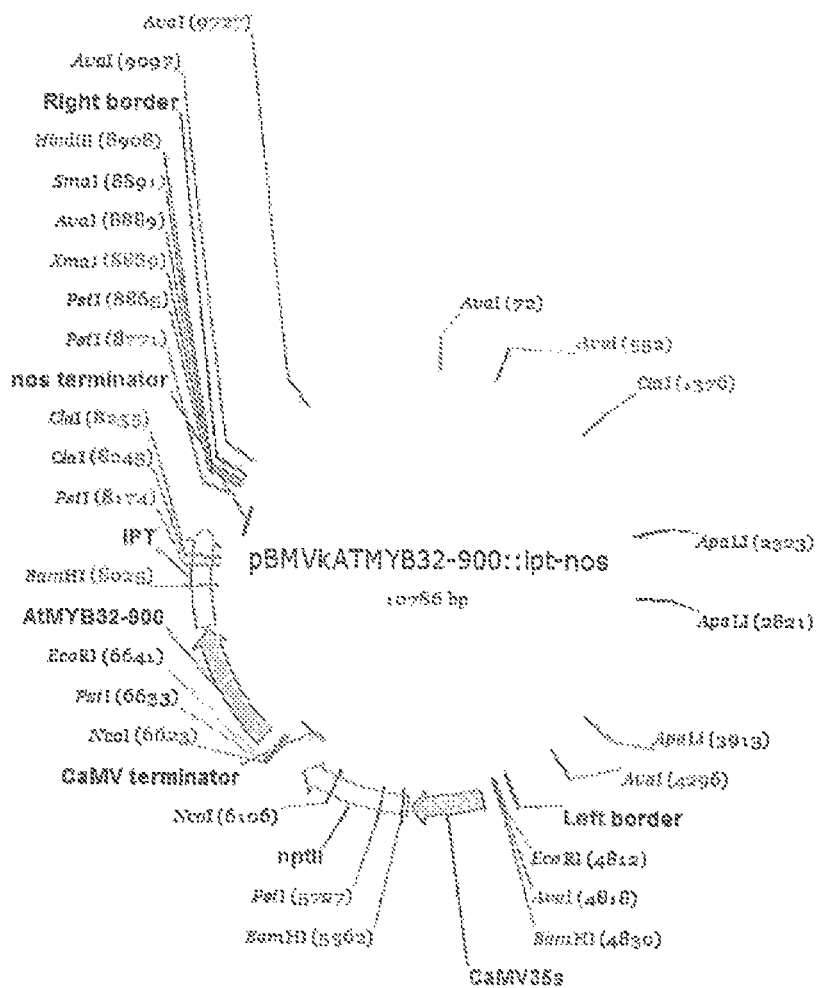

FIG. 16 shows vector details for pBMVkAtMYB32-900::ipt [Gene: Isopentyl transferase (IPT); Vector: pBMVkAtMYB32-900::ipt-nos (backbone pPZPRCS2); Selectable marker: spec; Plant selectable marker cassette: 35S::kan::35ST; Gene promoter: AtMYB32-900; Gene terminator: nos.].

Figure 17:
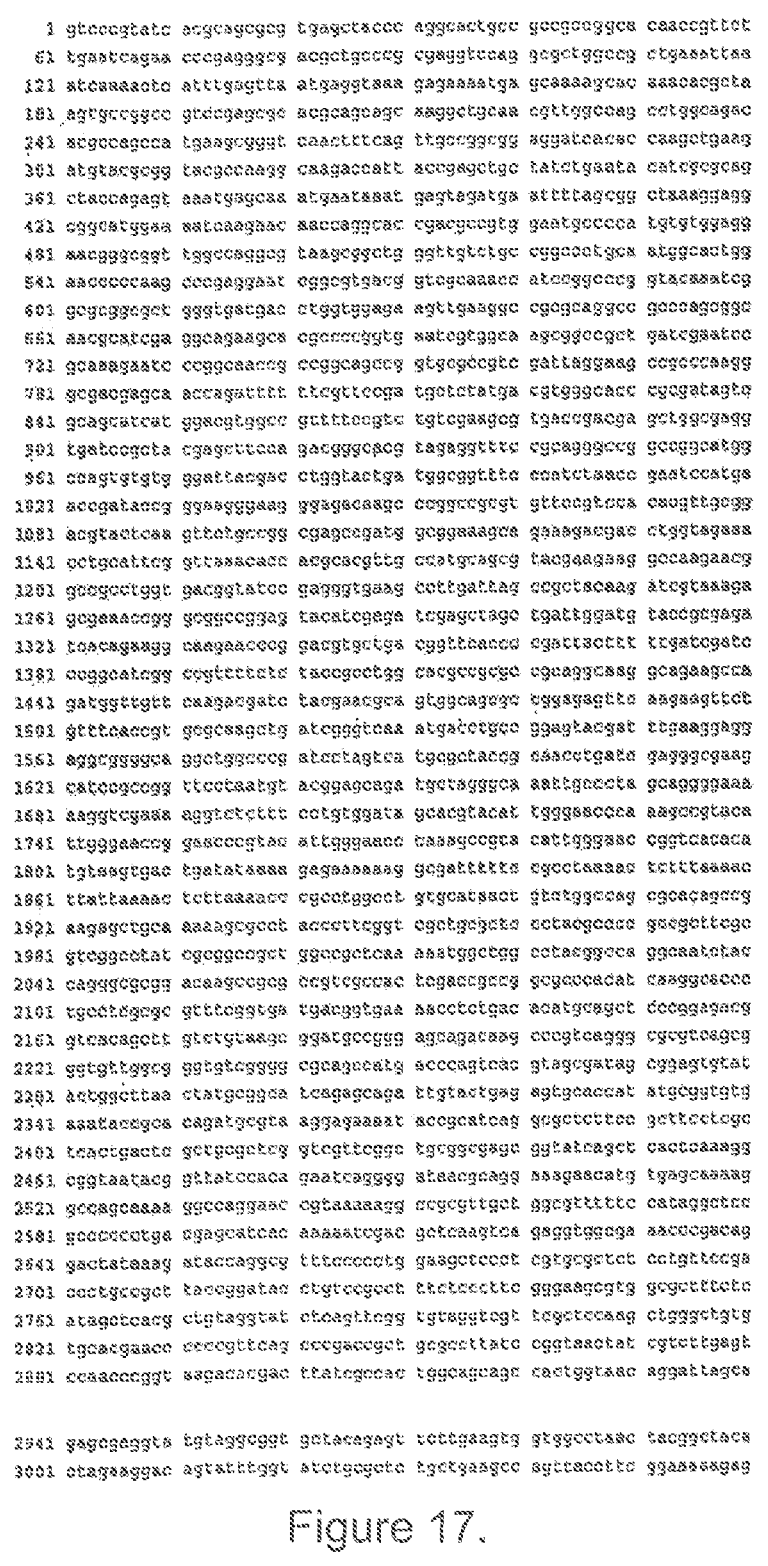
Figure 17:
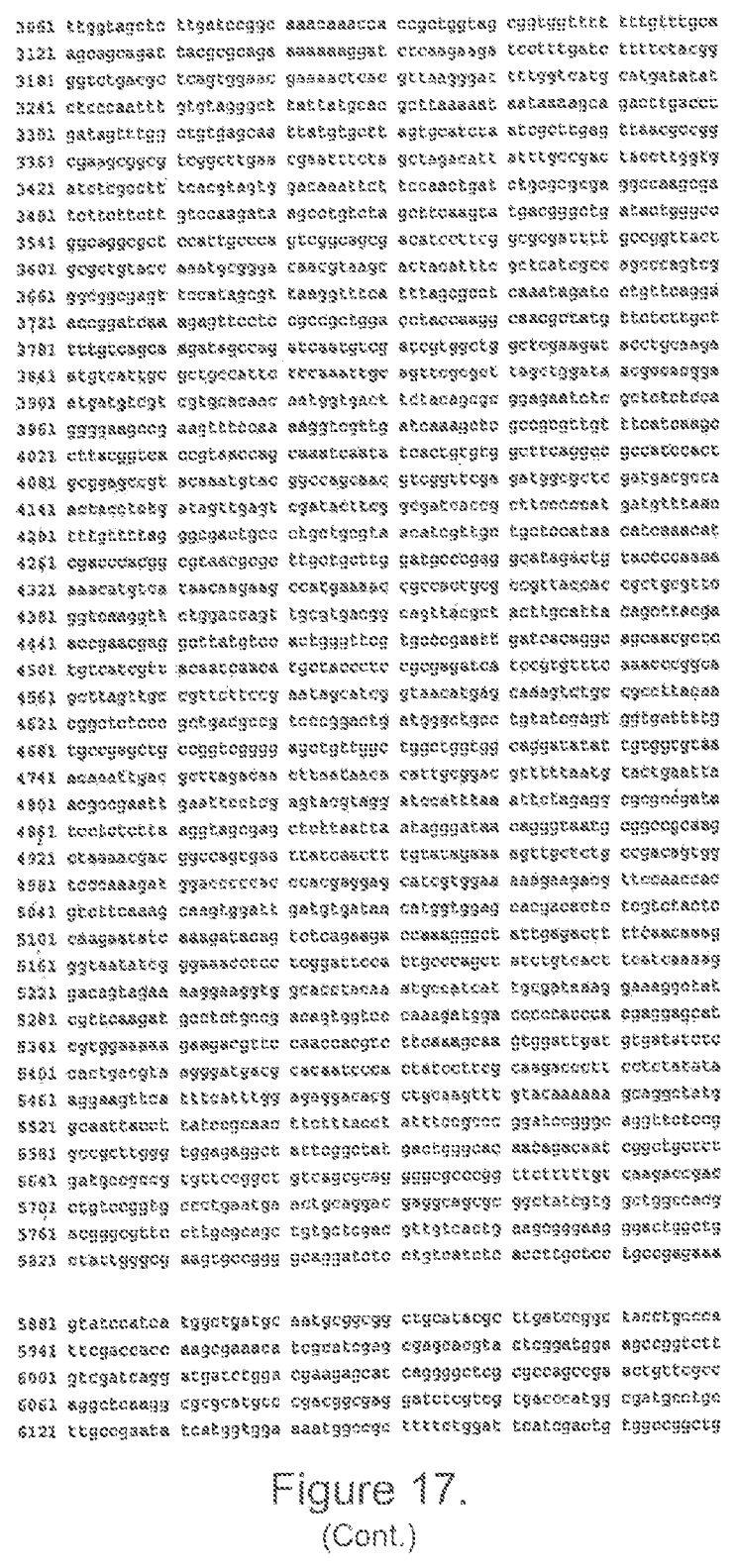

FIG. 17 shows nucleotide sequence of vector pBMVkAtMYB32-900::ipt-nos (Sequence ID No. 11).

Figure 18:
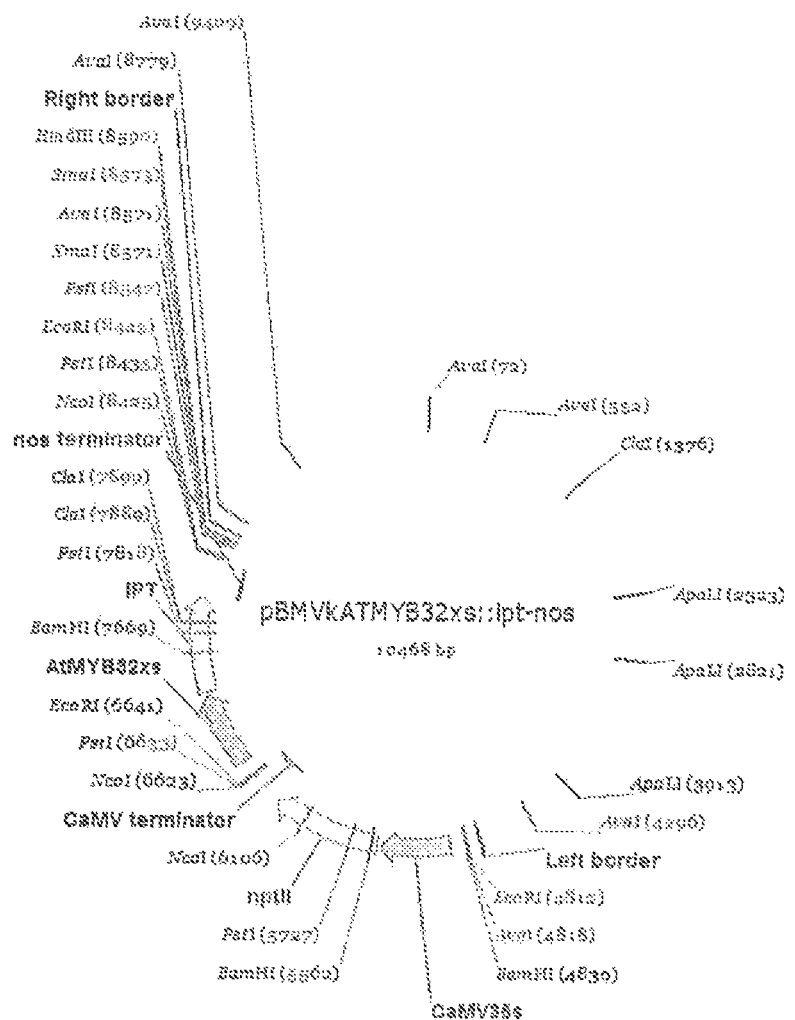

FIG. 18 shows vector details for pBMVkAtMYB32xs::ipt-nos [Gene: Isopentyl transferase (IPT); Vector: pBMVkAtMYB32XS::ipt-nos (backbone pPZPRCS2); Selectable marker: spec; Plant selectable marker cassette: 35S::kan::35ST; Gene promoter: AtMYB32-xs; Gene terminator: nos.].

Figure 19:
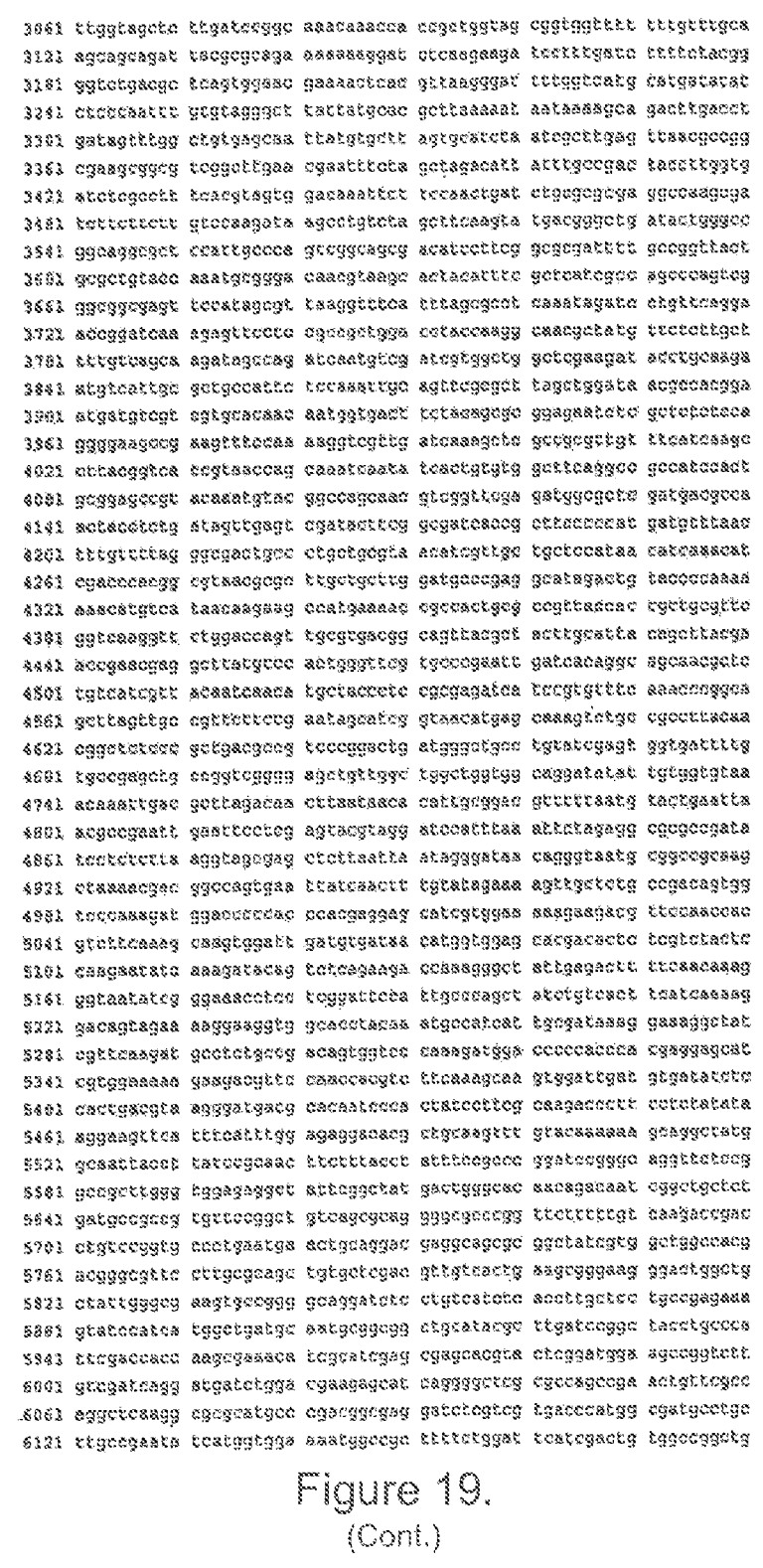
Figure 19:
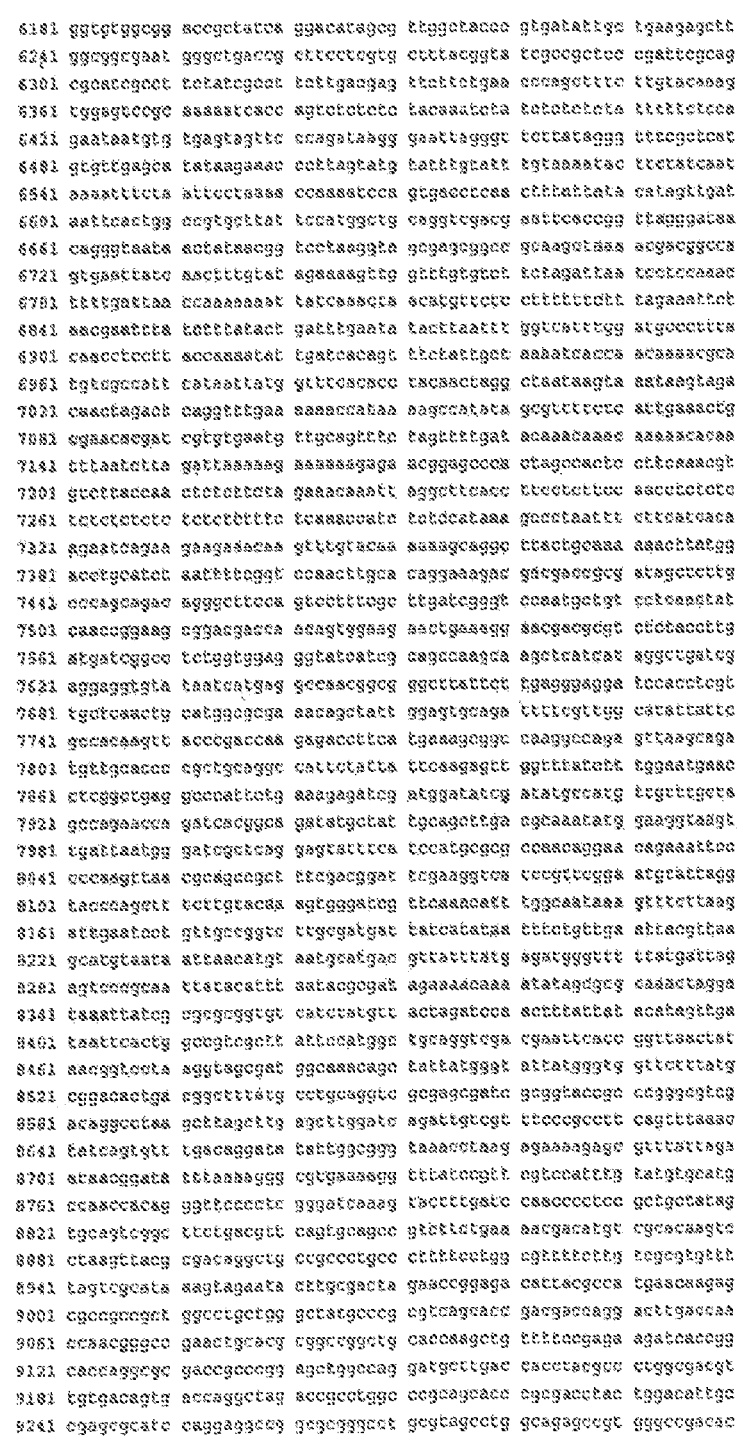
Figure 19:
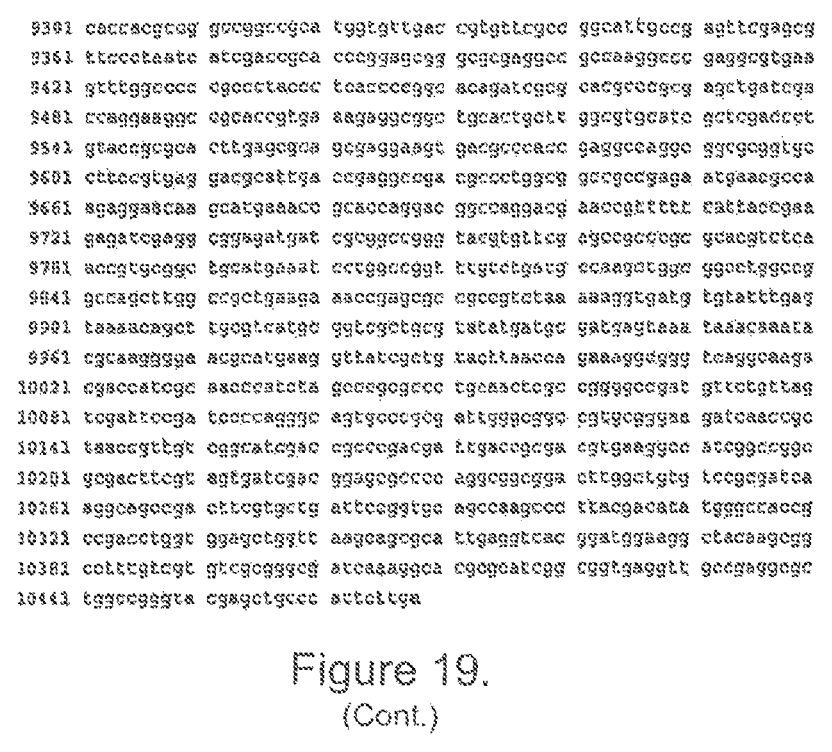

FIG. 19 shows nucleotide sequence of vector pBMVkAtMYB32xs::ipt-nos (Sequence ID No. 12).

Figure 20:
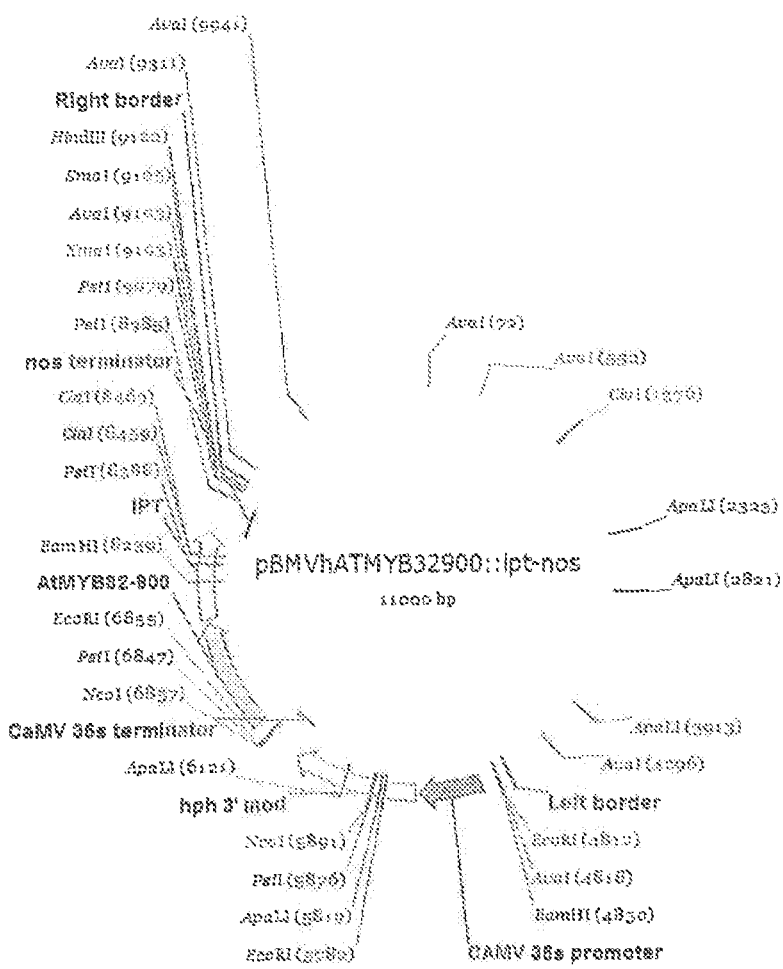

FIG. 20 shows vector details for pBMVhAtMYB32-900::ipt-nos [Gene: Isopentyl transferase (IPT); Vector: pBMVhAtMYB32-900::ipt-nos (backbone pPZPRCS2); Selectable marker: spec; Plant selectable marker cassette: 35S::hph::35ST; Gene promoter: AtMYB32-900; Gene terminator: nos.].

Figure 21:
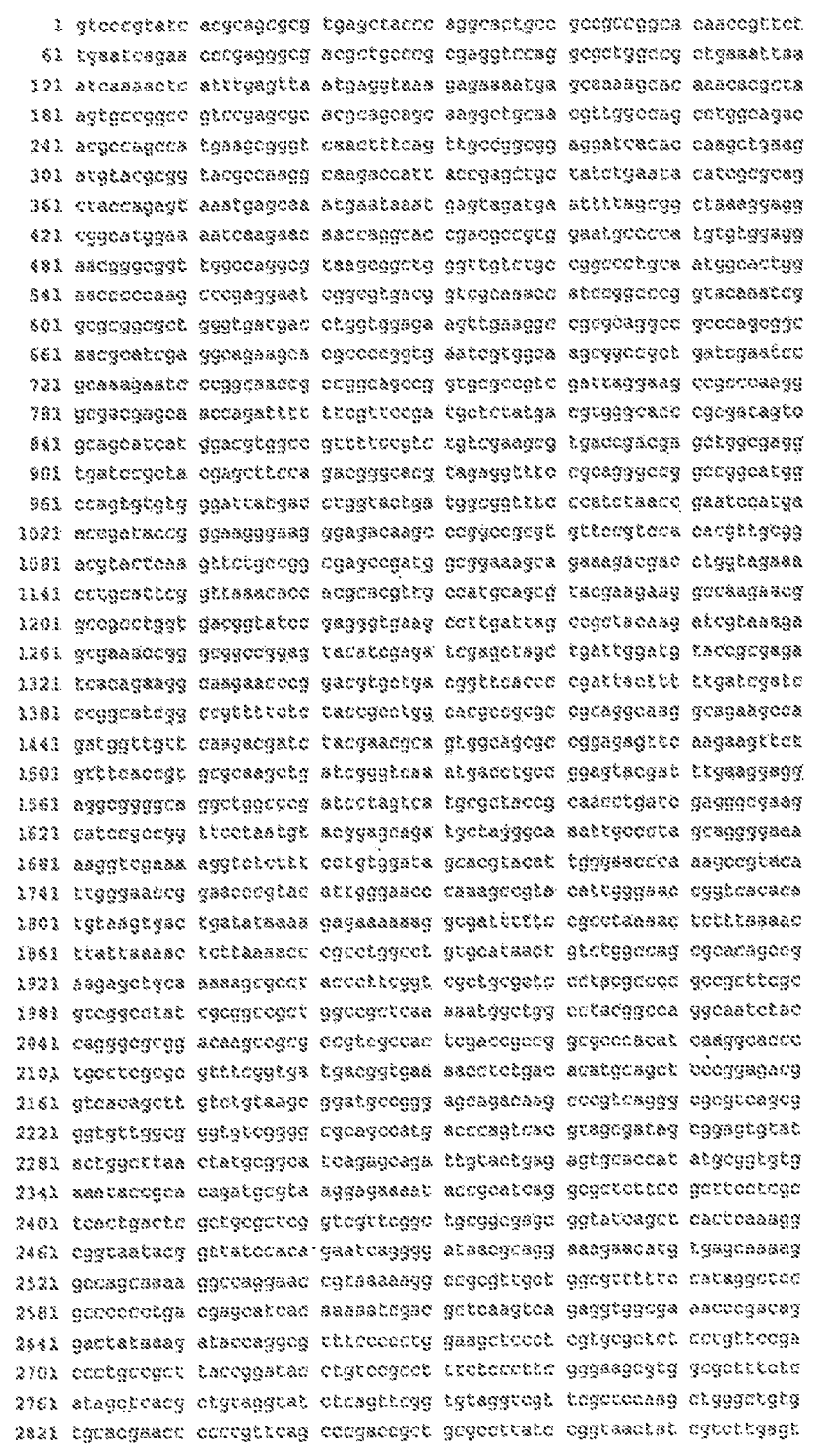

FIG. 21 shows nucleotide sequence of vector pBMVhAtMYB32-900::ipt-nos (Sequence ID No. 13).

Figure 22:
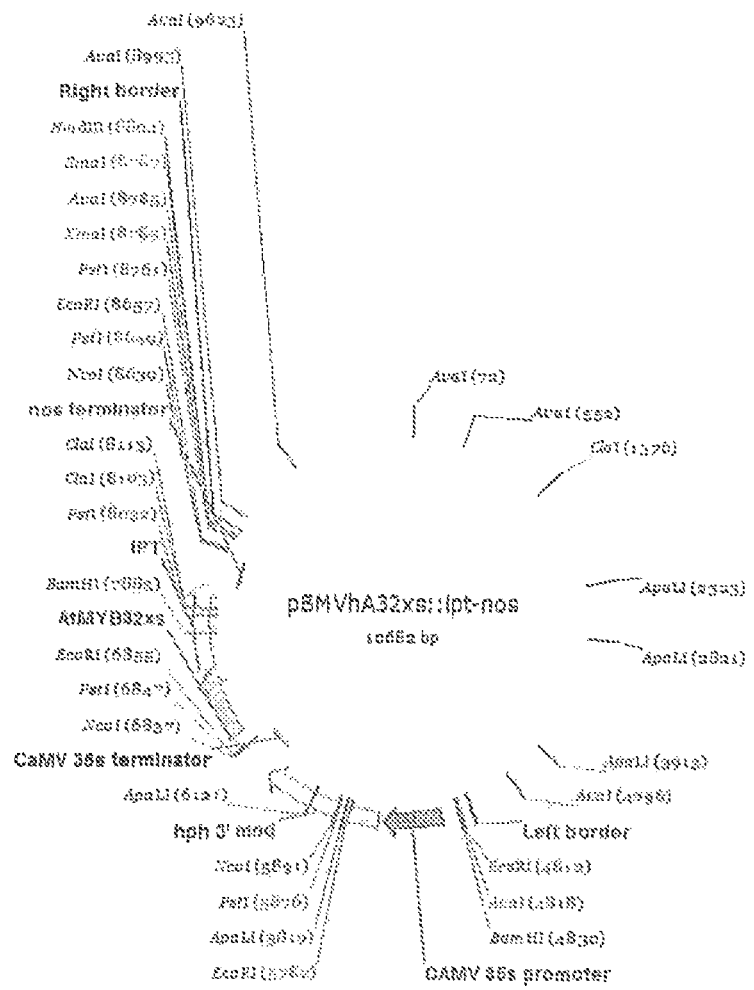

FIG. 22 shows vector details for pBMVhAtMYB32xs::ipt-nos [Gene: Isopentyl transferase (IPT); Vector: pBMVhAtMYB32XS::ipt-nos (backbone pPZPRCS2); Selectable marker: spec; Plant selectable marker cassette: 35S::hph::35ST; Gene promoter: AtMYB32-xs; Gene terminator: nos.].

Figure 23:
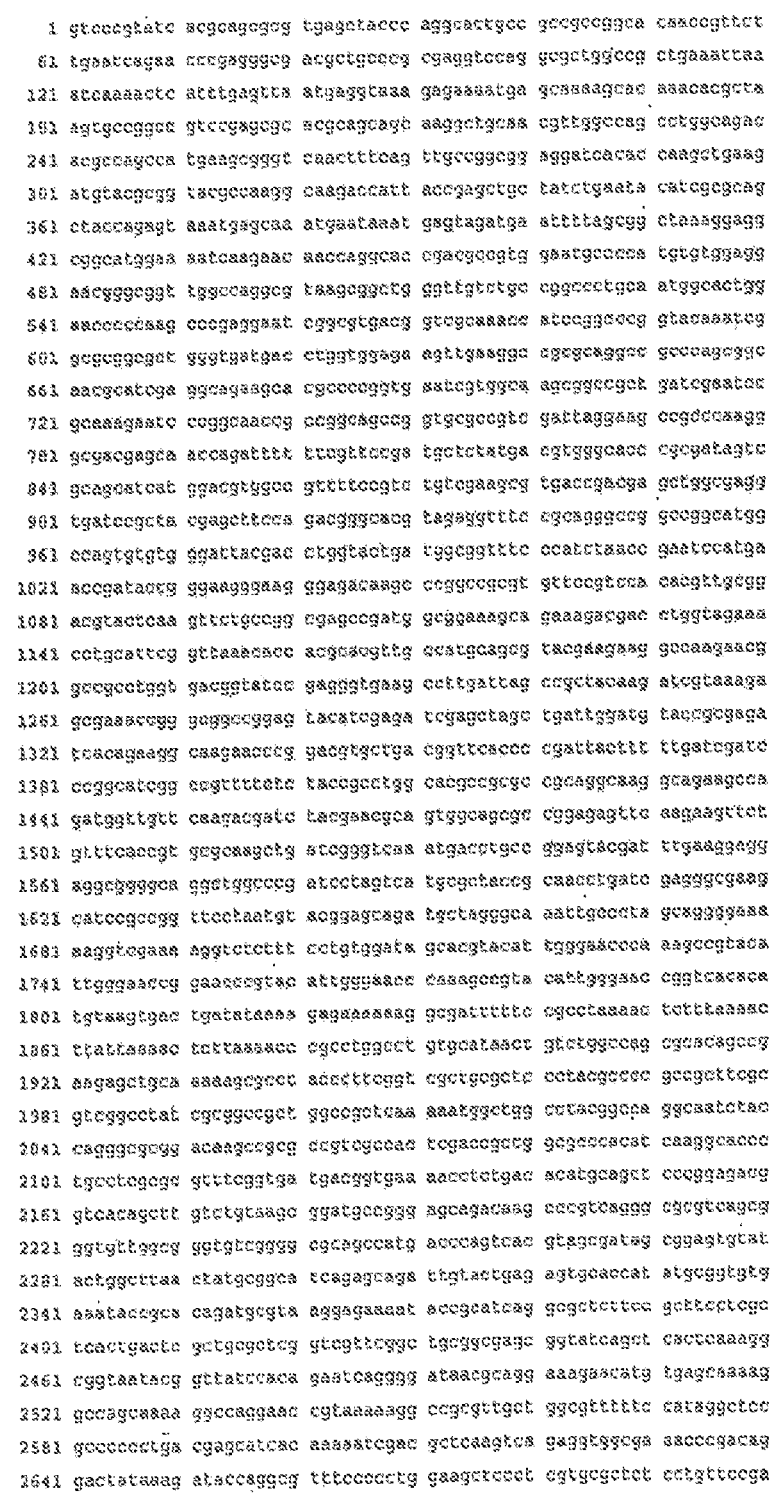

FIG. 23 shows nucleotide sequence of vector pBMVhAtMYB32xs::ipt-nos (Sequence ID No. 14).

Figure 24:
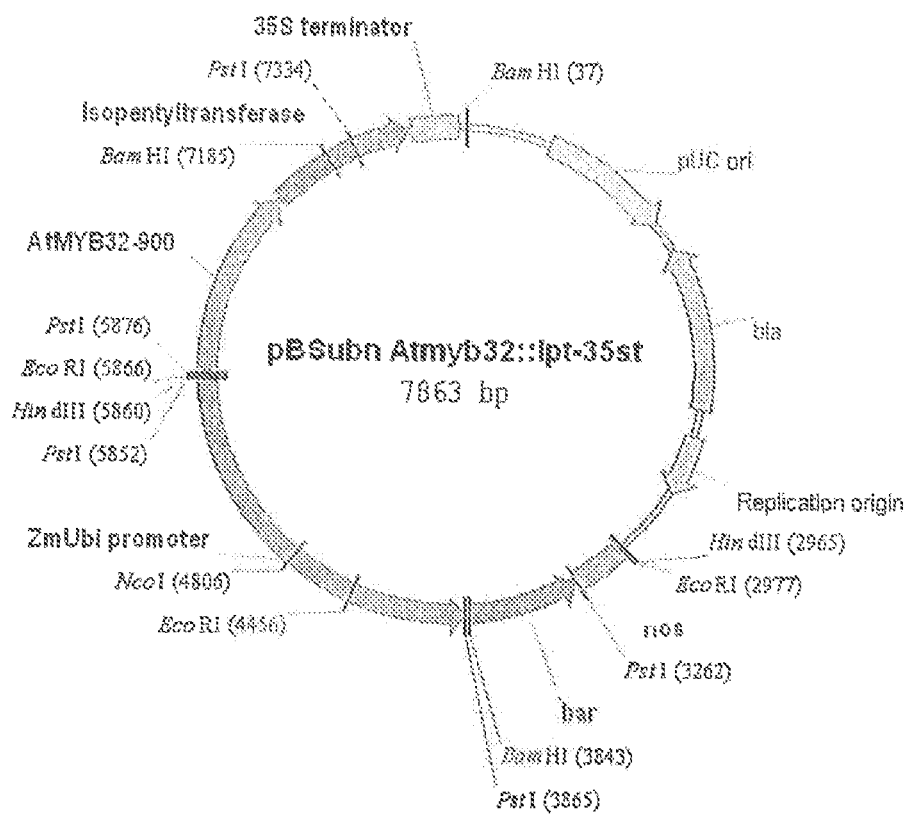
Figure 26A:
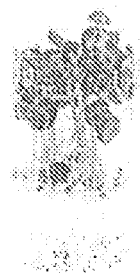
Figure 26B:
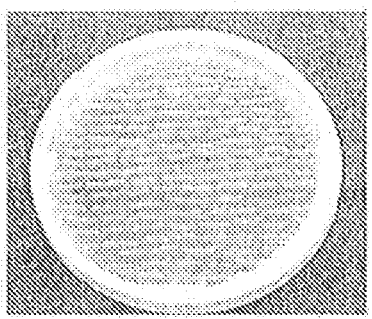
Figure 26C:
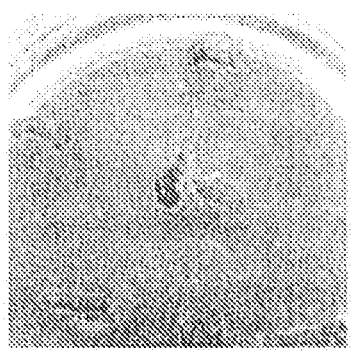
Figure 26D:
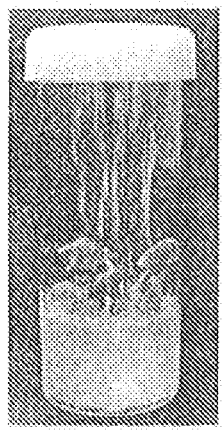
Figure 26E:
Figure 26F:
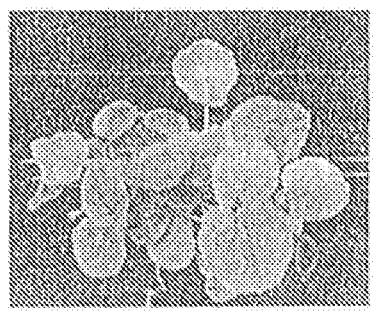
Figure 26G:
Figure 26H:
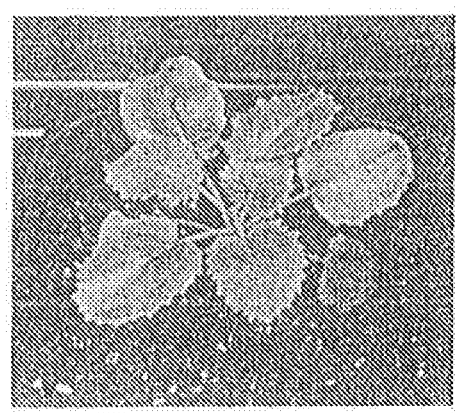
Figure 26I:
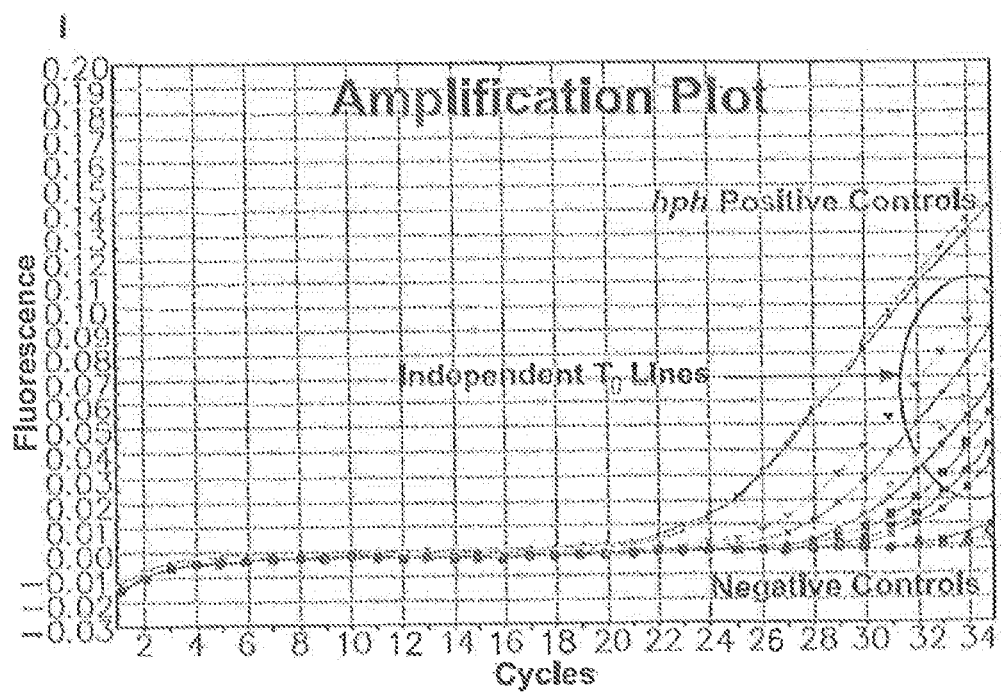
Figure 26J:

FIG. 24 shows vector details for pBSubn-AtMYB32-900::ipt-nos [Gene: Isopentyl transferase (IPT); Vector: pBSubn-AtMYB32-900::ipt-nos (backbone pPZPRCS2); Selectable marker: spec; Plant selectable marker cassette: Ubi::bar::nos; Gene promoter: AtMYB32-900; Gene terminator: nos.].

Figure 25:
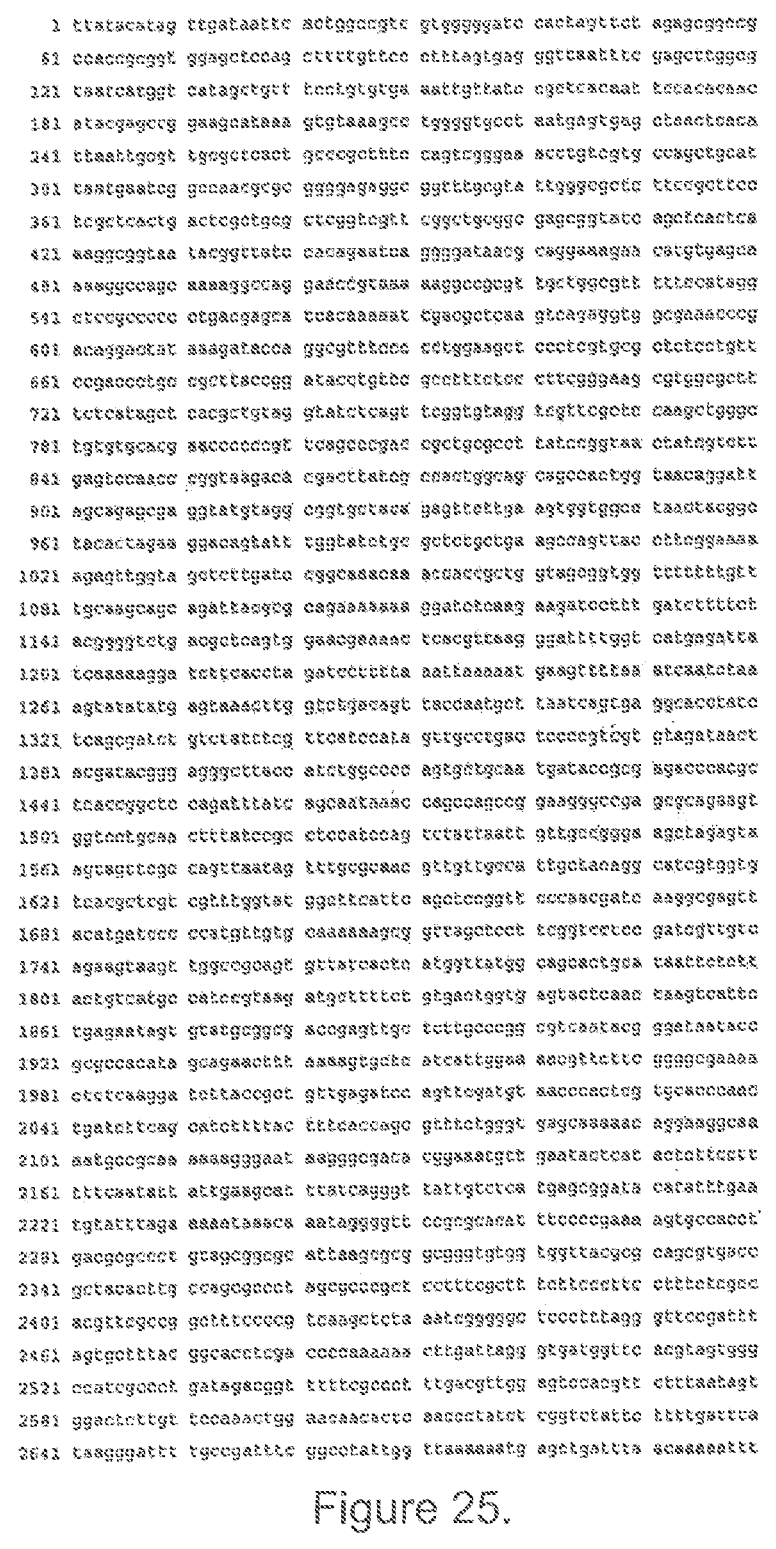
Figure 25:
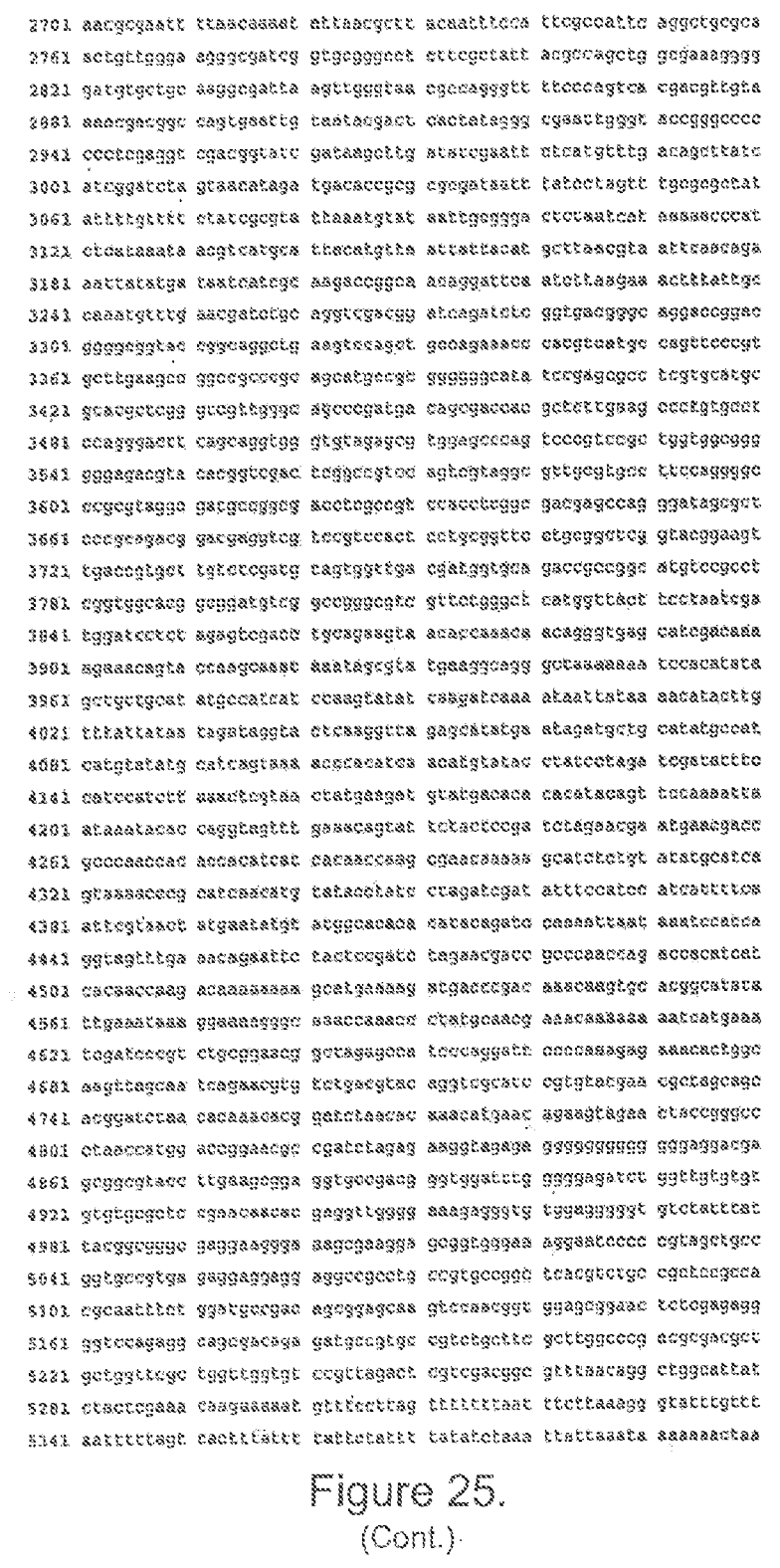

FIG. 25 shows nucleotide sequence of vector pBSAtMYB32900::ipt-nos (Sequence ID No. 15).

FIG. 26 shows generation of transgenic canola containing the pBMVhATMYB3-900::ipt-nos and pBMVhATMYB32xs::ipt-nos. A. Canola seeds are germinated in vitro; B. Hypocotyl sections are excised from 7-day-old seedlings and inoculated with an *Agrobacterium* suspension; C&D. Regeneration from inoculated hypocotyl sections under hygromycin selection; E-J. Transgenic $T_0$ canola plants carrying the pBMVhATMYB3-900::ipt-nos and pBMVhATMYB32xs::ipt-nos vectors.

Figure 27:
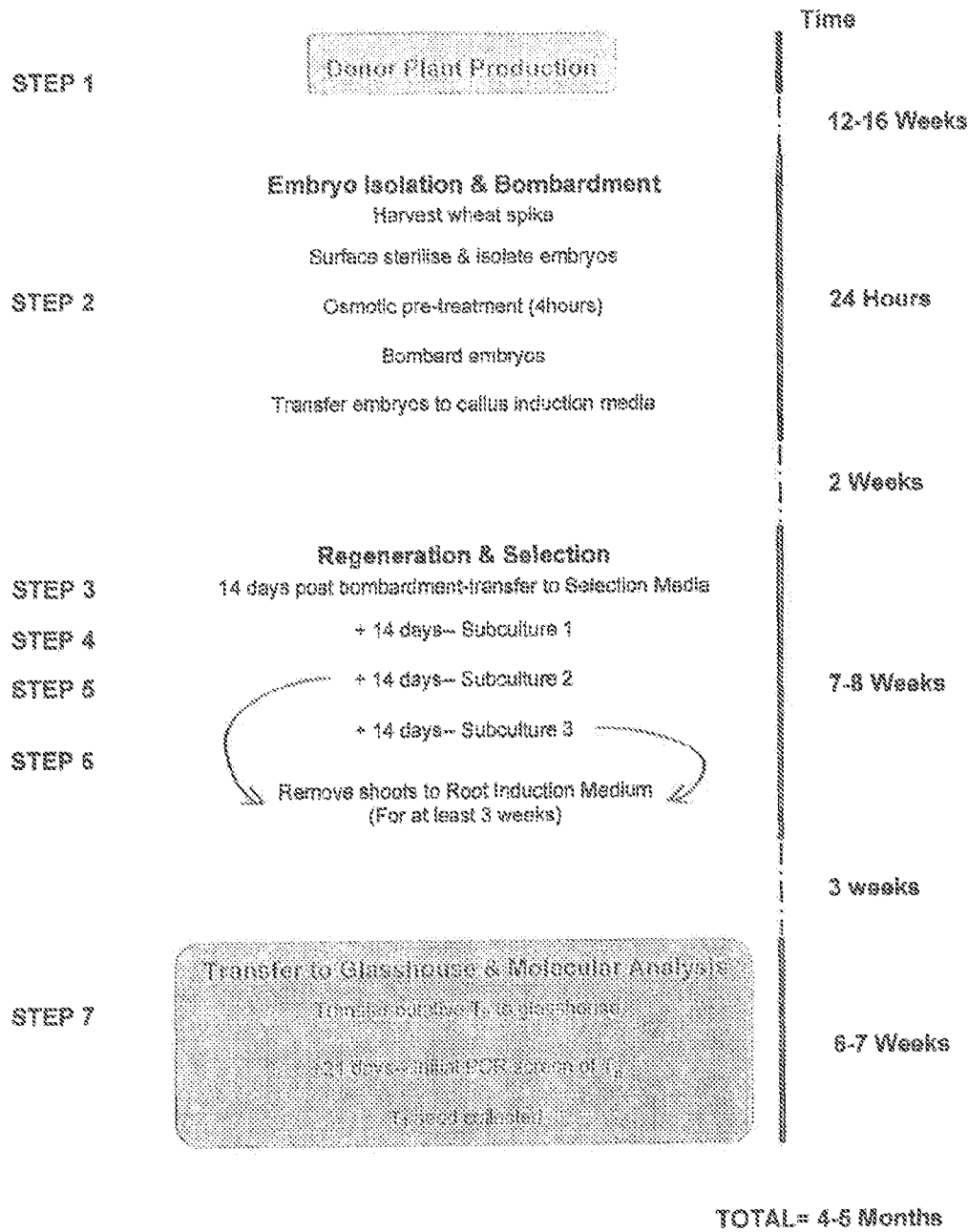

FIG. 27 shows a process for biolistic transformation of wheat.

Figure 28:
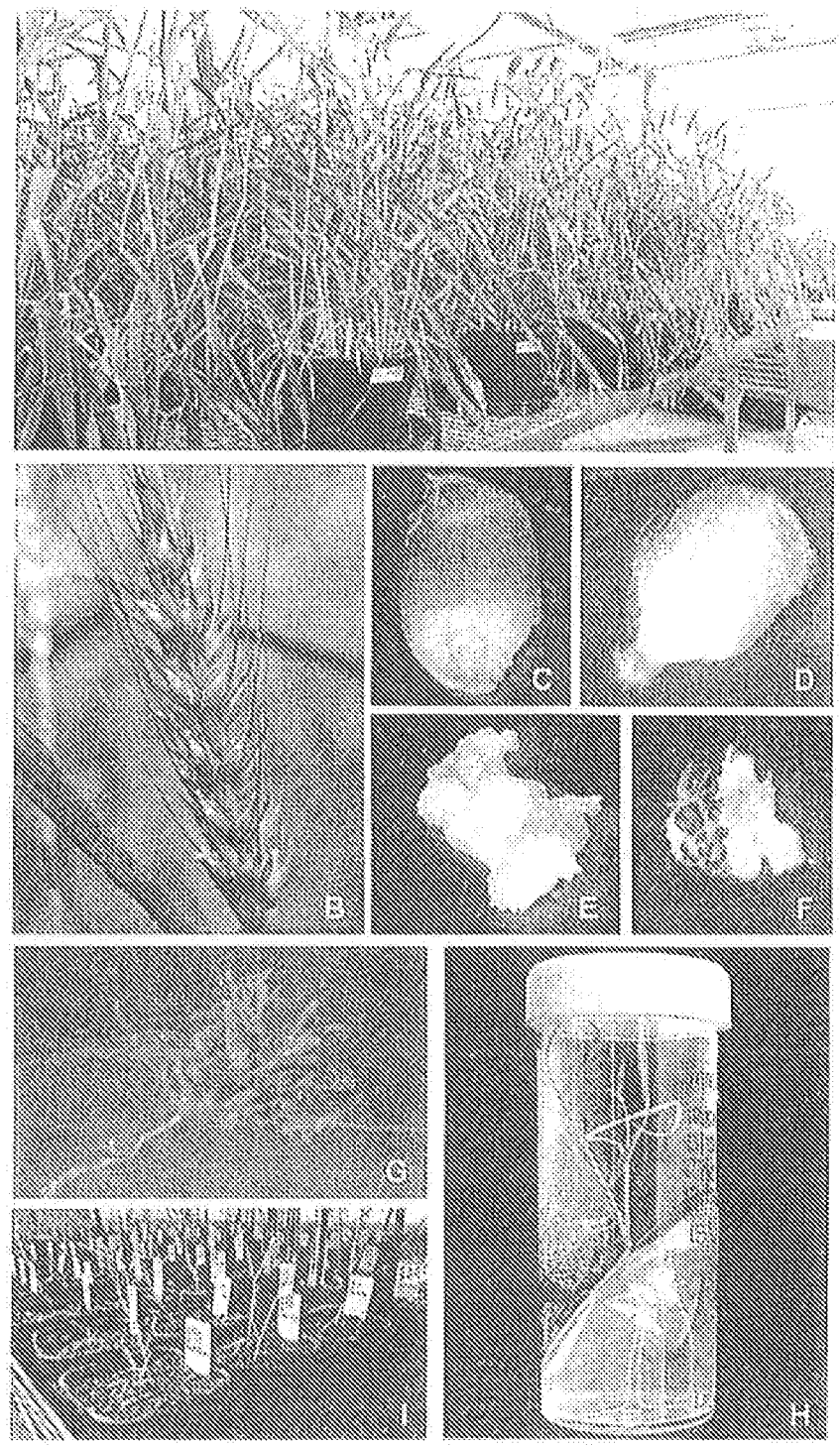

FIG. 28 shows biolistic transformation of wheat (*Triticum aestivum* L. MPB Bobwhite 26). Donor plant production (A & B); zygotic embryo isolation (C&D); Regeneration under glufosinate selection (E-G); Root formation under selection (H); $T_0$ plants growing under containment glasshouse conditions for recovery of transgenic offspring (I).

Figure 29:
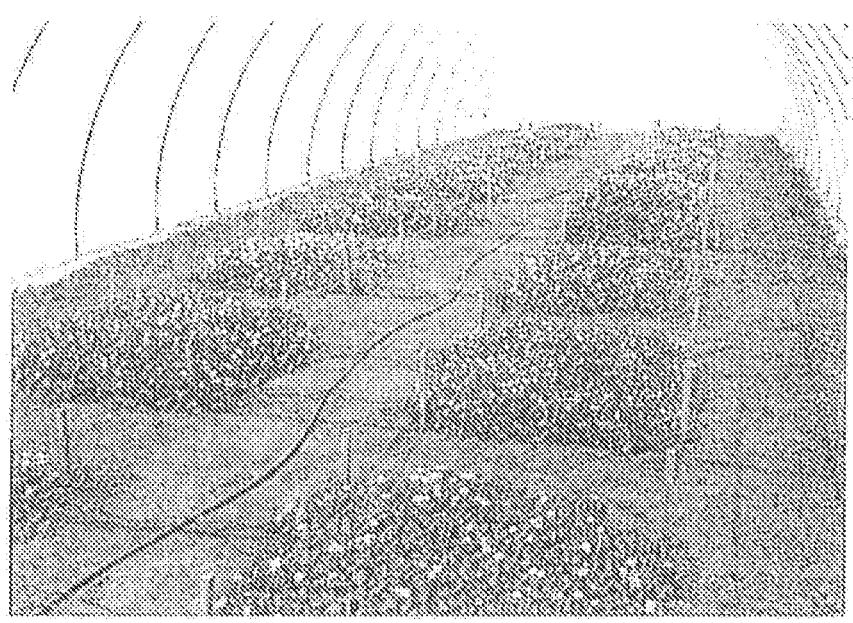

FIG. 29 shows contained field trial of transgenic white clover plants expressing chimeric Atmyb32::ipt genes.

Figure 30:
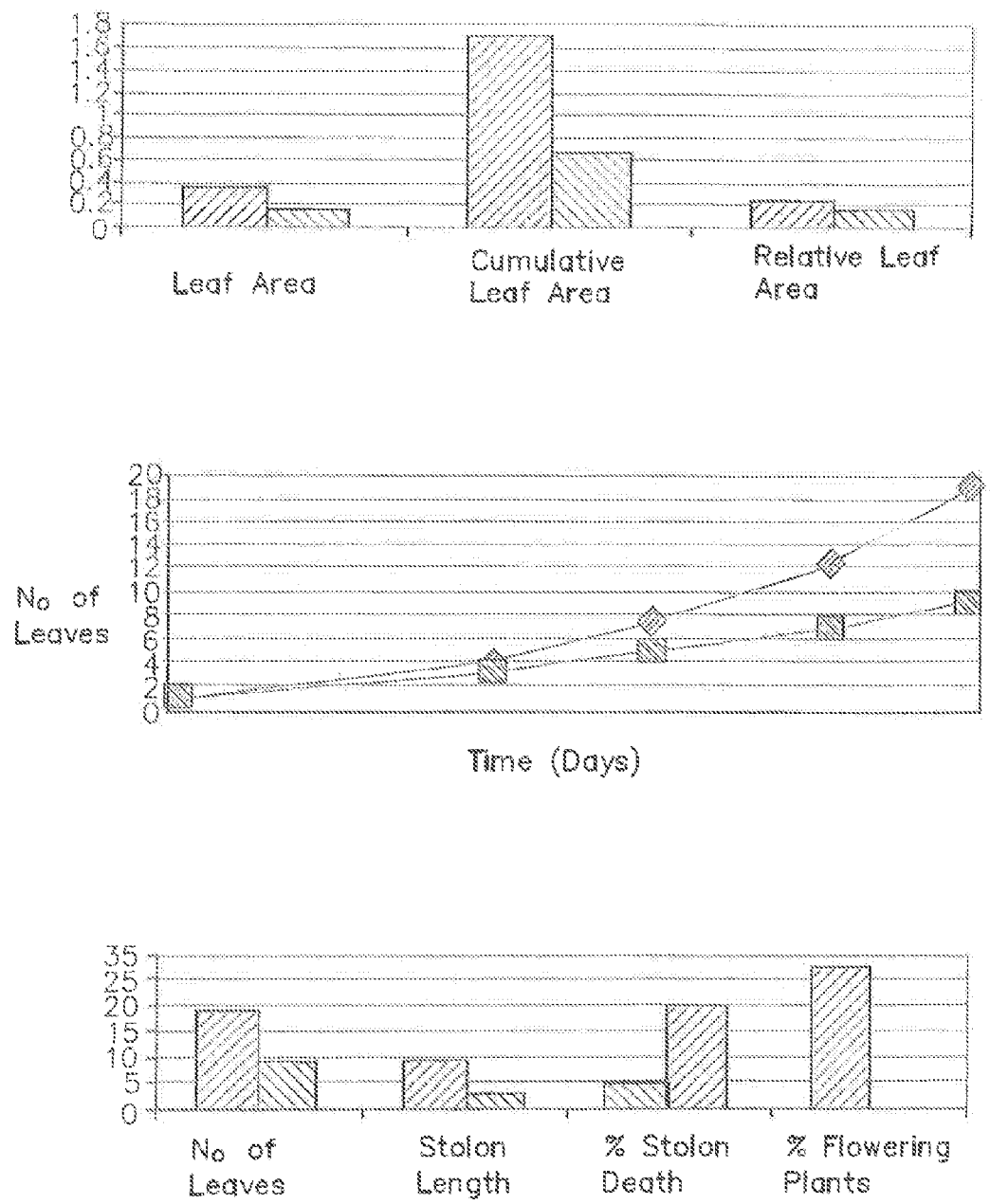

FIG. 30 shows comparative assessment of growth rates and growth dynamics of transgenic white clover plants expressing chimeric Atmyb32::ipt genes with non-transgenic control white clover plants. A) Growth Rates B) Growth Dynamics C) Growth Characteristics (after 45 days).

■ Transgenic white clover ■ Non-transgenic control white clover
(light) (dark)

Figure 31:
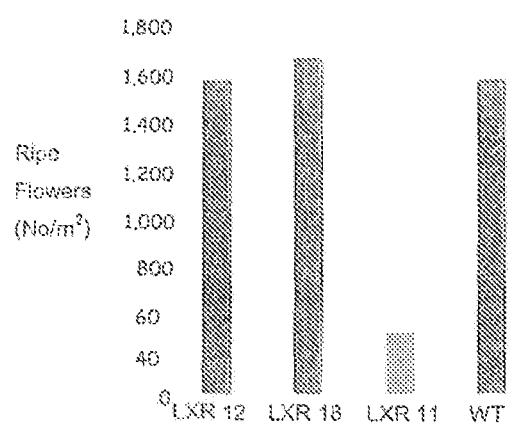

FIG. 31 shows flowering intensity (i.e., number of ripe flower per $m^2$) of transgenic white clover plants expressing chimeric Atmyb32::ipt genes (i.e., LXR 12, LXR 18 and LXR 11) and non-transgenic control white clover plants (i.e., WT) under contained field conditions.

Figure 32:
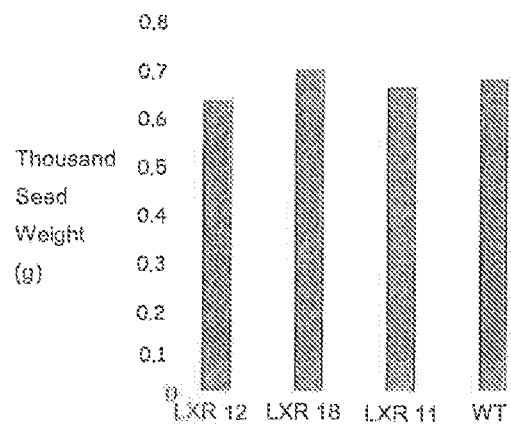

FIG. 32 shows seed weight (i.e., weight of thousand seeds, in grams) of transgenic white clover plants expressing chimeric Atmyb32::ipt genes (i.e., LXR 12, LXR 18 and LXR 11) and non-transgenic control white clover plants (i.e., WT) under contained field conditions.

Figure 33:
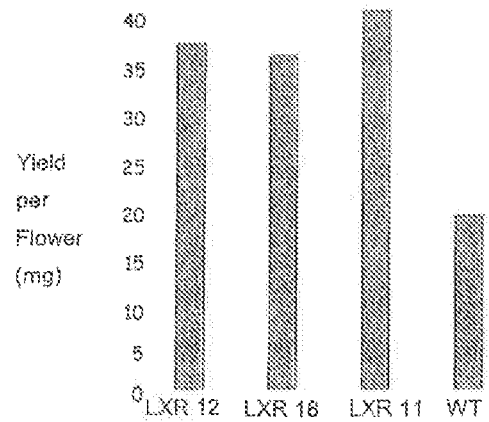

FIG. 33 shows seed yield per flower (in milligrams) of transgenic white clover plants expressing chimeric Atmyb32::ipt genes (i.e., LXR 12, LXR 18 and LXR 11) and non-transgenic control white clover plants (i.e., WT) under contained field conditions.

Figure 34:
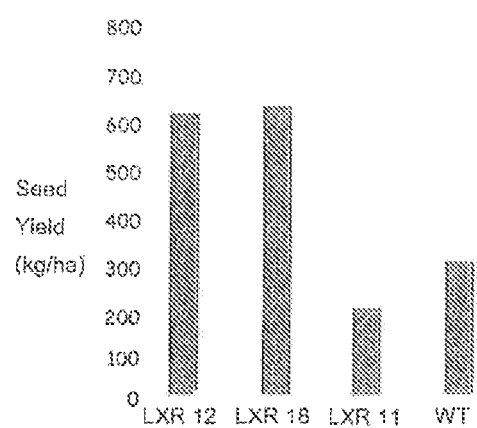
Figure 35A:
Figure 35B:
Figure 35C:
Figure 35D:

FIG. 34 shows seed yield per area (in kg/ha) of transgenic white clover plants expressing chimeric Atmyb32::ipt genes (i.e., LXR 12, LXR 18 and LXR 11) and non-transgenic control white clover plants (i.e., WT) under contained field conditions.

FIG. 35 shows generation of transgenic alfalfa plants containing the chimeric pBMVkATMYB3-900::ipt-nos and pBMVkATMYB32xs:: ipt-nos genes A. Petiole explants from alfalfa clones C2-3, C2-4 and 19-17 are used for inoculation with an *Agrobacterium* suspension and lead to the production of transformed embryogenic calli following selection in presence of kanamycin; B-D. Regeneration of transgenic alfalfa plantlets carrying chimeric genes from pBMVkATMYB3-900::ipt-nos and pBMVkATMYB32xs::ipt-nos vectors, from somatic embryos grown in vitro.

FIG. 36 shows PCR analysis of transgenic canola plants (T1 LXR canola plants Line 4). Genomic DNA was isolated from different transgenic canola plants of $T_1$ LXR04 lines and subjected to PCR using primers specific for A. the selectable marker (hph) or B. the candidate gene of interest (IPT).

Figure 37:
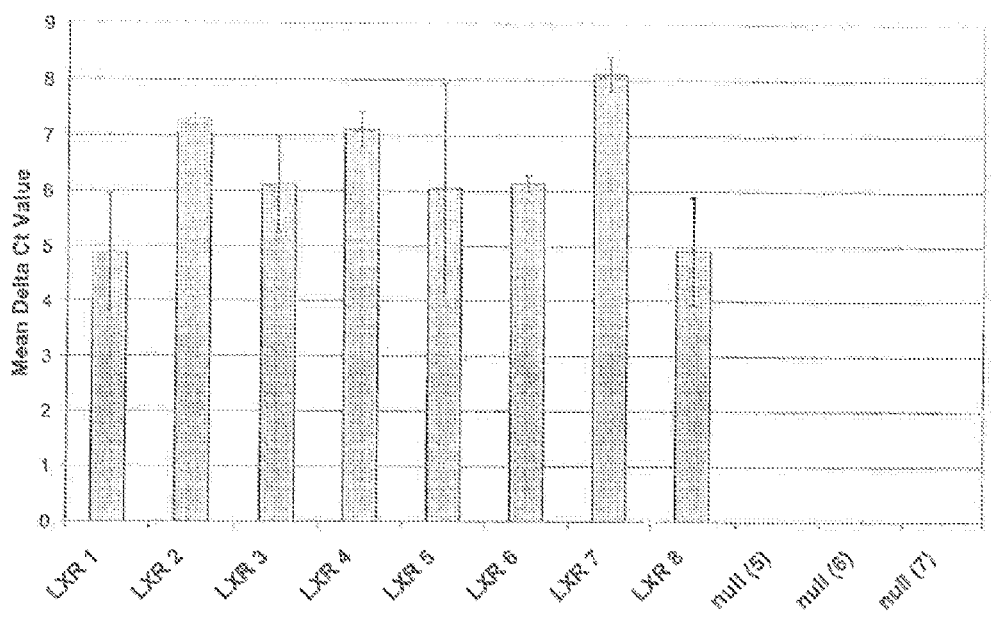

FIG. 37 shows expression analysis of the IPT gene in $T_1$ transgenic canola plants (T1 LXR canola relative IPT leaf expression).

Figure 38:
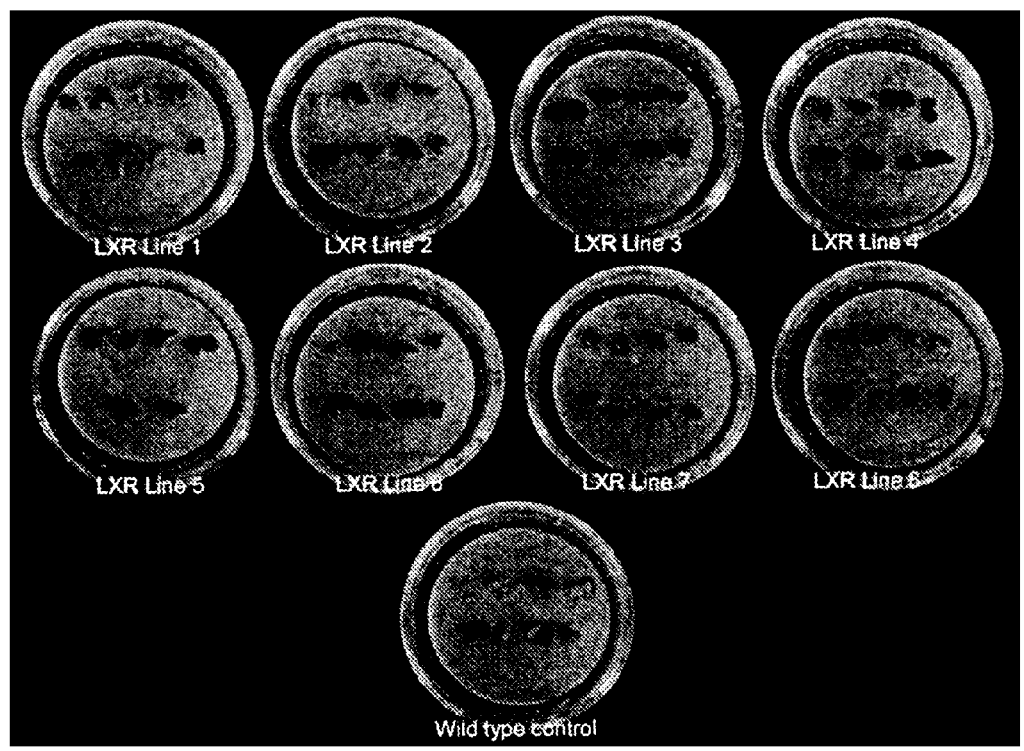

FIG. 38 shows transgenic canola displaying delay of detached cotyledon senescence as compared to wild-type control cotyledons 7 days following detachment.

Figure 39:
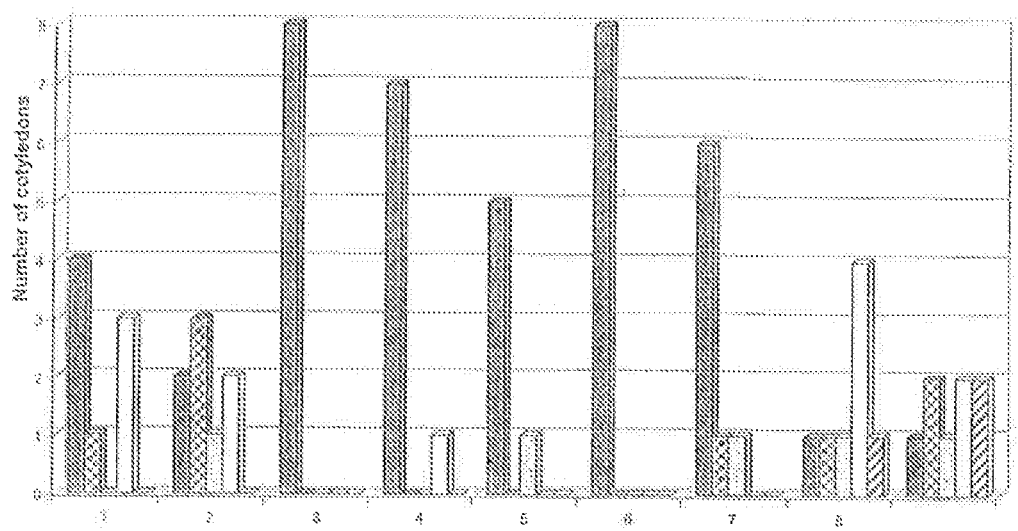

FIG. 39 shows the senescence score of $T_1$ transgenic canola cotyledons at 7 days following detachment.

■ 0 (dark solid column)=No Visible senescence; ▨ 1 (checkered column)=Pale Green; ▨ 2 (wavy-lined column)=Some Yellowing; ☐ 3 (light solid column)= Mostly Yellow; ▨ 4 (diagonally-lined column)=Completely Yellow.

Figure 40:
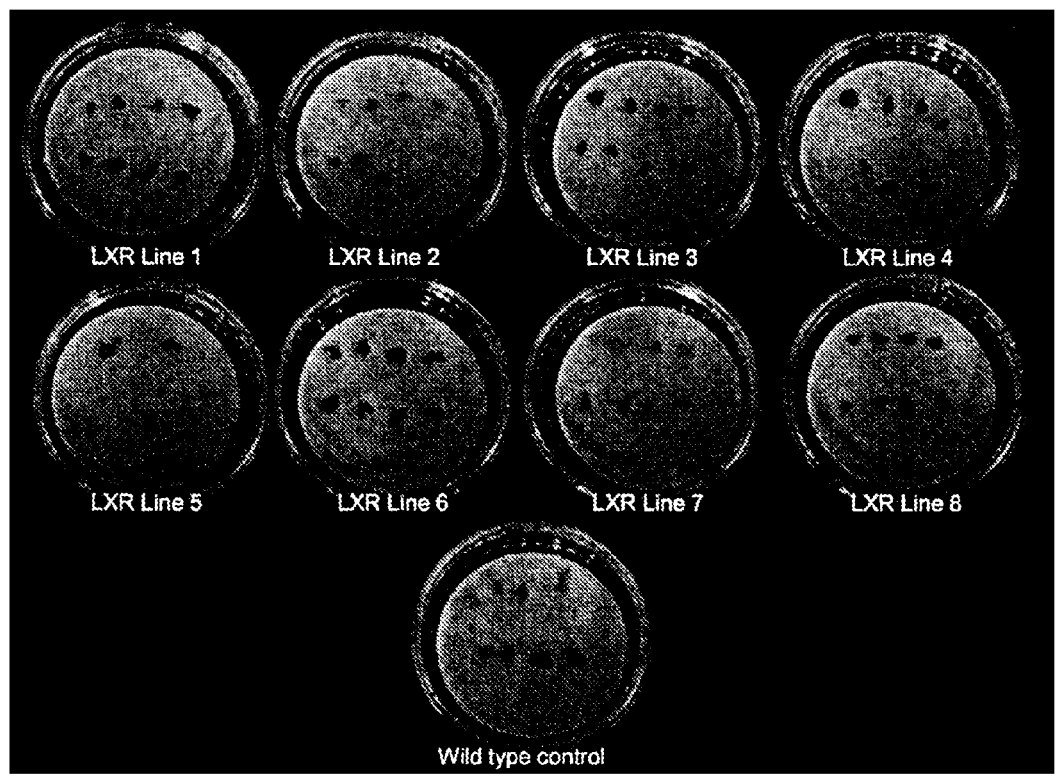

FIG. 40 shows transgenic canola displaying delay of detached juvenile leaf senescence as compared to wild-type control cotyledons 14 days following detachment.

Figure 41:
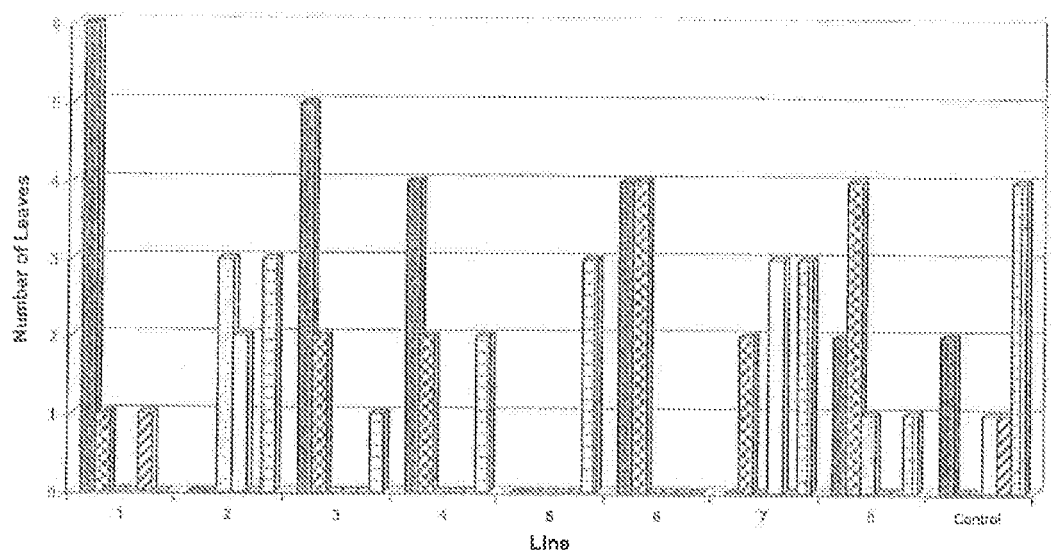

FIG. 41 shows senescence score of $T_1$ transgenic canola juvenile first leaves at 14 days following detachment.

■ 0 (dark solid column)=No Visible Senescence; ▨ 1 (checkered column)=Pale Green; ▨ 2 (wavy-lined column)=Some Yellowing ☐ 3 (light solid column)=Mostly Yellow; ▨ 4 (diagonally-lined column)=Completely Yellow; ▦ 5 (horizontally/vertically-lined column)=Rotting/Necrosis.

Figure 42:
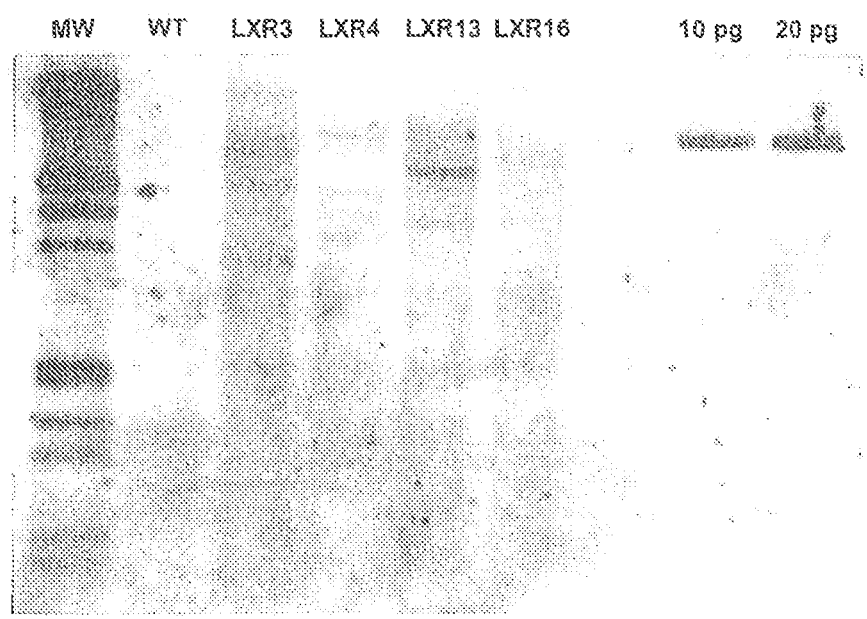

FIG. 42 shows Southern hybridisation analysis of transgenic wheat lines. Lanes include: MW—molecular weight; WT—wild-type; Transgenic wheat lines LXR3, LXR4, LXR13, LXR16 and positive plasmid controls containing 10 and 20 pg.

Figure 43:
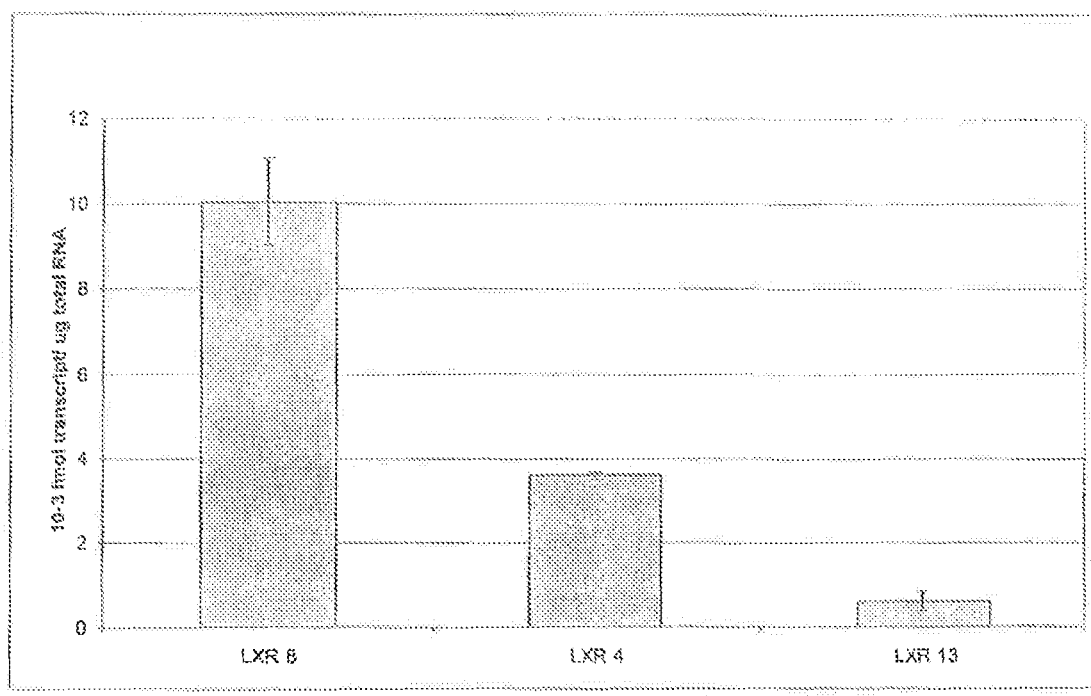

FIG. 43 shows expression analysis of independent $T_1$ transgenic wheat lines (IPT quantitative expression in wheat). Quantitative transcript values were determined in femtomoles (fmol) per microgram of RNA using a standard curve derived from plasmid DNA containing the target sequence. Samples represent high, medium and low expression classes for candidate gene IPT.

Figure 44:
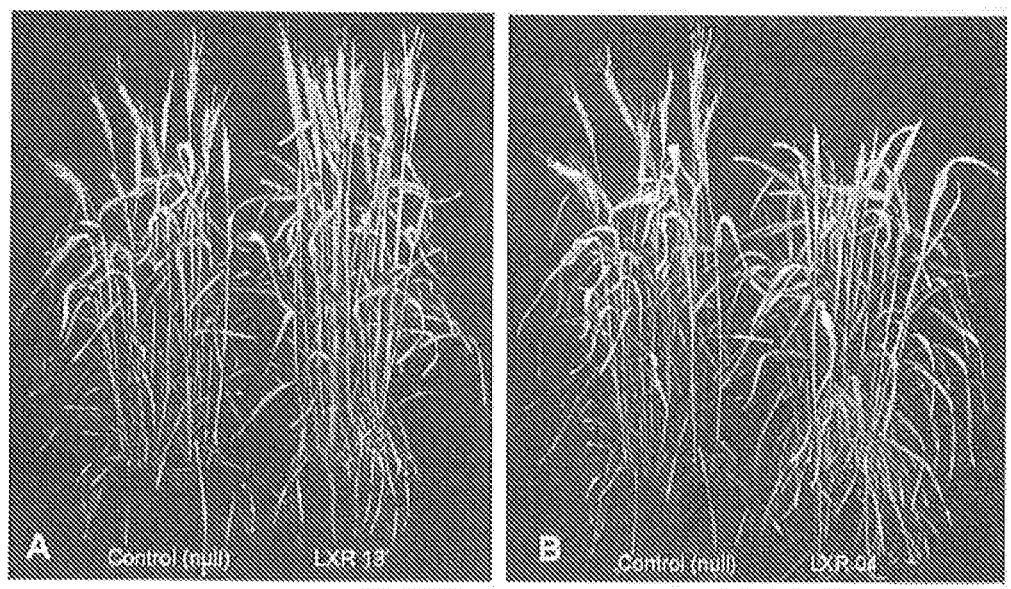

FIG. 44 shows phenotypic variation of glasshouse grown $T_1$ transgenic wheat plants. A. $T_1$ LXR 13 wheat plants displaying normal phenotype as compared to null control wheat plants. B. $T_1$ LXR 04 wheat plants displaying stunted phenotype and increased flag leaf number as compared to null control wheat plants.

Figure 45:
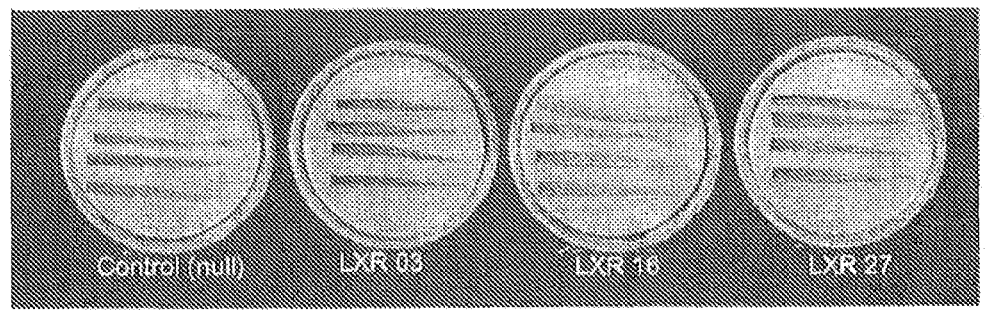

FIG. 45 shows transgenic wheat displaying delay of leaf senescence as compared to null control leaves 7 days following detachment.

Figure 46:
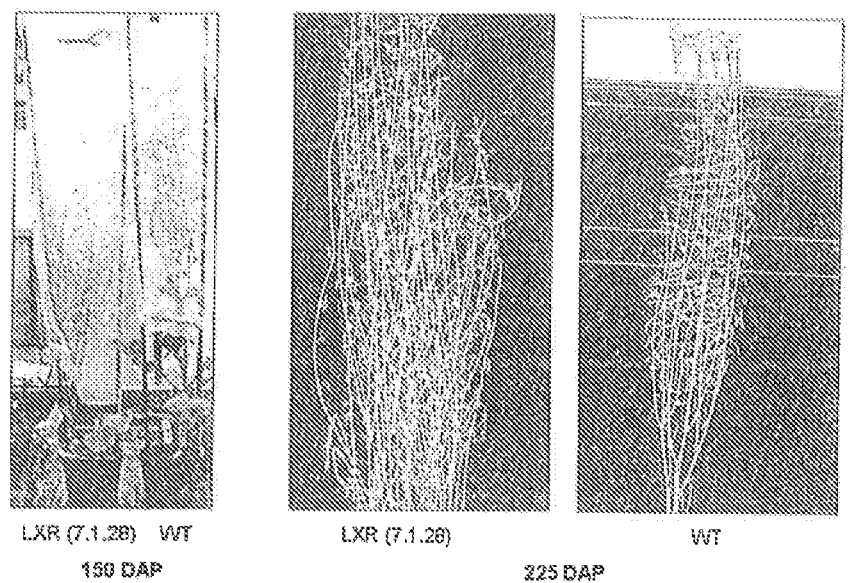

FIG. 46 shows phenotypes of the T2 transgenic canola plants expressing the chimeric atmyb32::ipt transgene (i.e., LXR lines), compared to wild-type non-transgenic control canola plants (i.e., WT), 150 DAP (left) and 225 DAP (right).

Figure 47:
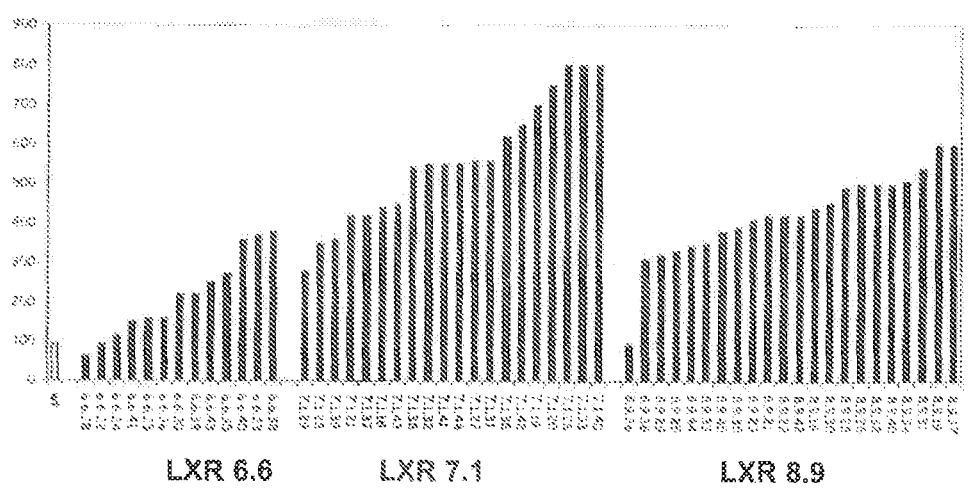

FIG. 47 shows flowering intensity in transgenic canola plants expressing the chimeric atmyb32::ipt transgene (i.e., LXR lines), compared to wild-type non-transgenic control canola plants (i.e., WT).

Figure 48:
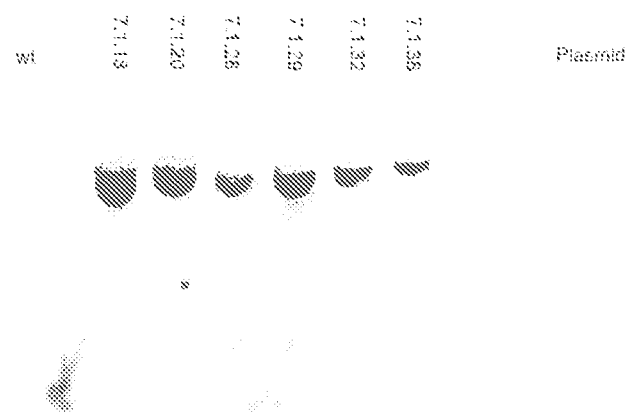

FIG. 48 shows southern hybridisation analyses of T2 transgenic canola lines (i.e., LXR 7.1 lines) expressing the chimeric atmyb32::ipt transgene. WT: wild-type, negative, non-transgenic control.

Figure 49:
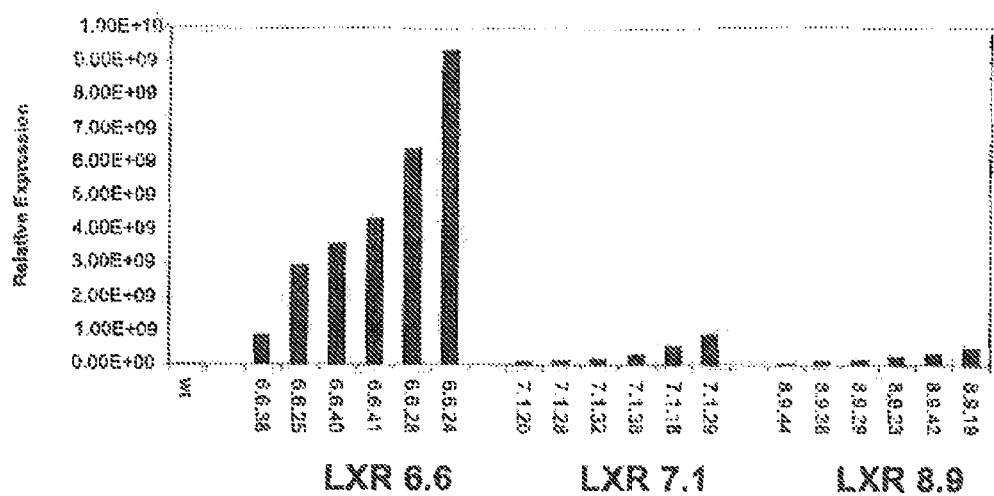

FIG. 49 Relative expression level of atmyb32::ipt transgene in T2 transgenic canola lines (i.e., LXR 6.6-, 7.1- and 8.9 T2 lines). WT: wild-type, negative, non-transgenic control.

Figure 50:
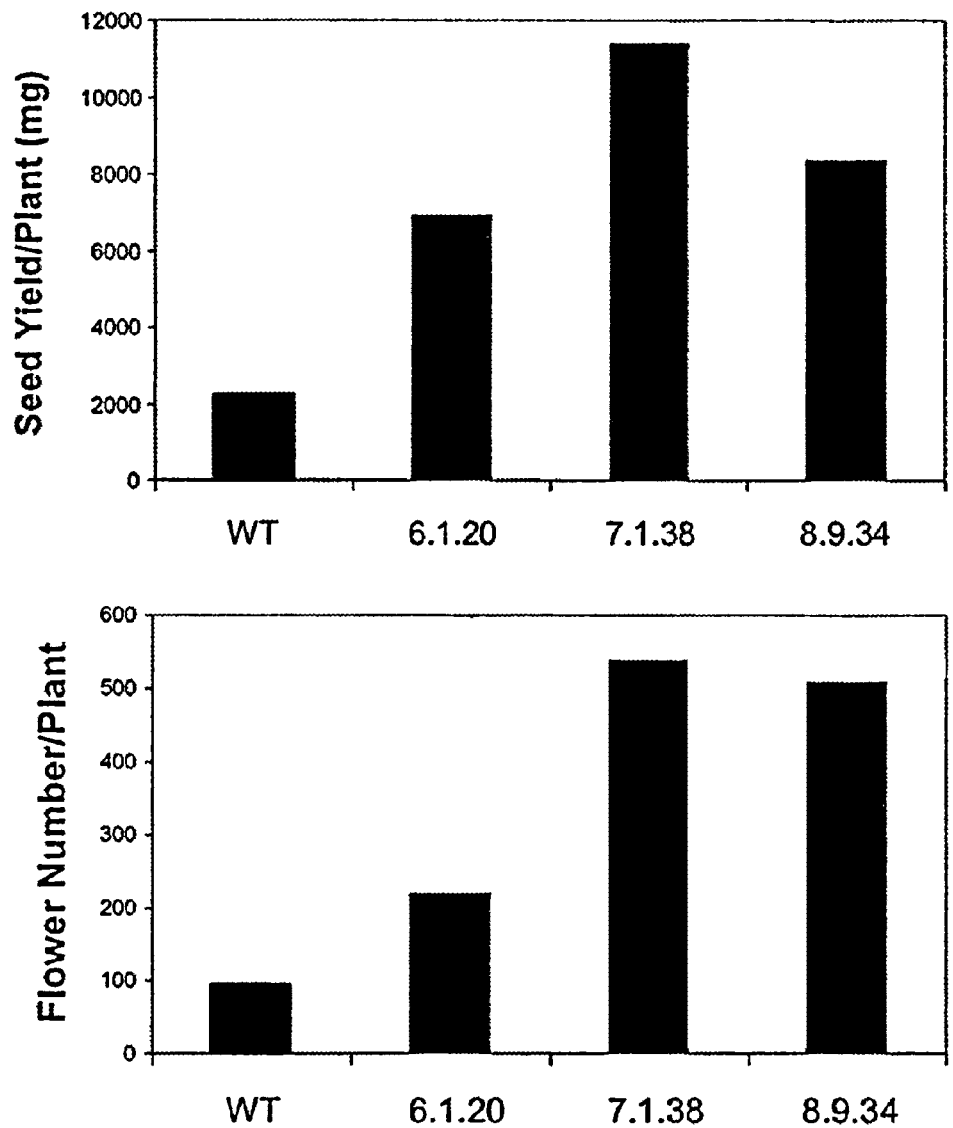

FIG. 50 Flowering intensity and seed yield in T2 transgenic canola lines expressing the chimeric atmyb32::ipt transgene (i.e., lines 6.6-, 7.1- and 8.9) compared to wild-type, negative, non-transgenic control (i.e., WT).

Figure 51:
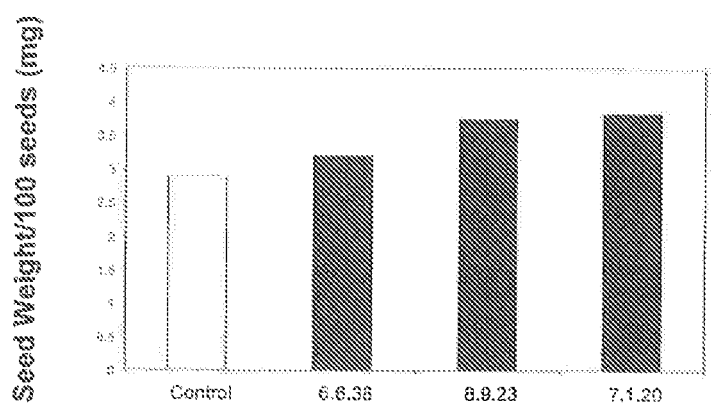

FIG. 51 Seed weight of T2 transgenic canola lines expressing the chimeric atmyb32::ipt transgene (i.e., lines 6.6-, 7.1- and 8.9) compared to wild-type, negative, non-transgenic control (i.e., WT).

EXAMPLES

Example 1

Atmyb32 Promoter Sequence and Promoter Sequence Variants

The Atmybb32 promoter sequence and variants thereof are shown in FIGS. 1-4.

Example 2

Cytokinin Biosynthesis Genes

Examples of cytokinin biosynthesis genes suitable for use in the present invention are shown in FIGS. 6, 8 and 10. Suitable genes also include those encoding the polypeptides shown in FIGS. 7, 9 and 11.

Example 3

Production of Transgenic White Clover Plants

Transgenic white clover plants (*Trifolium repens* cv. Haifa and Irrigation) were produced by *Agrobacterium*-mediated transformation using a binary vector carrying the chimeric atmyb32::ipt gene (FIG. 12a). The transgenic plants were screened by PCR using ipt and nptII primers (FIG. 12b). HindIII digested genomic DNA samples subjected to Southern DNA hybridization analysis showed that the DNA fragments greater than 4.4 kb were detected in all lanes by both ipt and nptII probes, demonstrating the presence and integration of full-length T-DNA into the white clover genome (FIG. 12). Transgenic lines Hmi01, Imi06, Imi11, and Imi18 (Lane 1, 3, 5, 8 and 12 respectively) appeared to have a single copy of full-length T-DNA integrated in the genome. Other transgenic lines had multiple copies of the atmyb32::ipt transgene.

Example 4

IPT Gene Expression in Transgenic White Clover Plants

The expression of the atmyb32::ipt transgene in transgenic white clover (*T. repens*) plants was assessed by RT-PCR. The ipt mRNA was detected in leaf tissues of all atmyb32::ipt transgenic white clover plants examined, with varying levels of PCR products detected (FIG. 13).

Example 5

Delayed Detached Leaf Senescence in Transgenic White Clover Plants

Experiments were performed to assess detached leaf senescence of atmyb32::ipt transgenic plants. Rapid yellowing was observed in detached leaves from non-transformed and atmyb32::gusA transgenic white clover plants of both cultivars within one week. Transgenic lines Hmi01, Hmi08, Imi16 and Imi18 showed delayed senescence while Imi11 and Imi12 showed no sign of yellowing by the end of 7 days. After two weeks, the leaves of all atmyb32::ipt transgenic plants were much greener than those of non-transformed and atmyb32::gusA control transgenic plants (FIG. 14). The degree of senescence in excised leaves was in the order HC, Hmg>Hmi01>Hmi08 for cv. Haifa, and IC and Img>Imi16>Imi18>Imi11 and Imi12 for cv. Irrigation. HC is Haifa untransformed control, Hmg is Haifa atmyb32::gusA control, IC is Irrigation untransformed control, 1 mg is Irrigation atmyb32::gusA control. Hmi01, Hmi08, Imi16, Imi18, Imi11 and Imi12 are independent atmyb32::ipt transgenic white clover plants from the cultivar Haifa (H) and Irrigation (I), respectively.

Example 6

Plant Morphology and Root Development in Transgenic White Clover Plants

Normal plant morphology as well as normal shoot and normal root development was observed in atmyb32:ipt transgenic white clover plants (FIG. 6), thus indicating that the regulated expression of the ipt gene under control of the atmyb32 promoter did not negatively affect neither rooting nor apical dominance of the transgenic white clover plants (Table 1).

TABLE 1

| Transformant | Cultivar | Construct | ipt copy No | Phenotype |
| --- | --- | --- | --- | --- |
| Hmi01 | Haifa | Atmyb32::ipt | 1 | Normal |
| Hmi08 | Haifa | Atmyb32::ipt | >3 | Normal |
| Imi06 | Irrigation | Atmyb32::ipt | 1 | Normal |
| Imi07 | Irrigation | Atmyb32::ipt | 3 | Normal |
| Imi09 | Irrigation | Atmyb32::ipt | >3 | Normal |
| Imi10 | Irrigation | Atmyb32::ipt | >3 | Normal |
| Imi11 | Irrigation | Atmyb32::ipt | 1 | Normal |
| Imi12 | Irrigation | Atmyb32::ipt | 2 | Normal |
| Imi16 | Irrigation | Atmyb32::ipt | 2 | Normal |
| Imi18 | Irrigation | Atmyb32::ipt | 1 | Normal |

Normal plant morphology and normal rooting was observed in ten independent atmyb32::ipt transgenic white clover lines analysed. Estimated ipt gene copy numbers in the ten independent atmyb32::ipt transgenic white clover lines are shown.

Example 7

Generation of Vectors for Plant Transformation

Four binary vectors have been generated for *Agrobacterium*-mediated transformation of plants (FIGS. 16-19). Each vector has a pPZP200 vector backbone (Hajdukiewicz et al., 1994) and contains either chimeric Atmyb32-900::ipt-nos or Atmyb32-xs::ipt-nos with or without a chimeric 35S::nptII-35st or 35S::hph-35st selectable marker cassettes.

One transformation vector has been constructed for biolistic transformation (FIGS. 20 and 21). The transformation vector contains chimeric Atmyb32-900::ipt-35st with a chimeric Ubi::bar-nos selectable marker cassette.

The Atmyb32 promoter, promoter variant Atmyb32xs, the isopentyl transferase gene and terminators 35st and nos were amplified by PCR using Gateway™ (Invitrogen) adapted primers and cloned into a pDONR221 entry vectors. These were subsequently cloned using recombination into destination vectors containing the conventionally cloned selectable marker cassettes. All vectors were fully sequenced following strict quality assurance protocols.

Example 8

*Agrobacterium*-Mediated Transformation of Canola

*Brassica napus*

Binary vectors pBMVhATMYB3-900::ipt-nos (FIG. 20) and pBMVhATMYB32xs::ipt-nos (FIG. 22) containing chimeric ipt genes under control of Atmyb32 promoter (FIG. 1) and Atmyb32xs variant promoter sequence with deleted root-specific motifs (FIG. 2) were used for *Agrobacterium*-mediated transformation of *Brassica napus* hypocotyl segments (FIG. 26).

*Brassica napus* seeds are surface sterilised in 70% ethanol for 2 minutes, washed 3 times in sterile water then further surface sterilised in a solution containing 1% (w/v) Calcium hypochlorite and 0.1% (v/v) Tween 20 for 30 minutes. The seeds are washed at least 3 times in sterile water and planted in 120 ml culture vessels containing a solidified germination medium containing 1× Murashige and Skoog (Murashige and Skoog *Physiol. Plant,* 15: 473-497, 1962) macronutrients, 1× micronutrients and B5 organic vitamins, supplemented with 500 mg/L MES, 2% (w/v) sucrose at a pH of 5.8 with the addition of 4 g/L Gelrite. The vessels are incubated at 25° C. under 16 h light/8 h dark conditions for 7 days to encourage germination.

After 7 days, seedlings of *Brassica napus* (whole seedlings) are transferred to a liquid medium consisting of 1× Murashige and Skoog macronutrients, 1× micronutrients and B5 organic vitamins, supplemented with 500 mg/L MES, 3% (w/v) sucrose at a pH of 5.8. Seedlings are grouped together and the roots and cotyledons removed prior to cutting the hypocotyls into 7-10 mm sections and plating on 9×1.5 cm petri dishes containing a preconditioning medium consisting of 1× Murashige and Skoog macronutrients, 1× micronutrients and B5 organic vitamins, supplemented with 500 mg/L MES, 3% (w/v) sucrose at a pH of 5.8 solidified with 6.4 g/l Bacto-Agar.

Hypocotyl sections are cultured for 24 hours prior to inoculation with an *Agrobacterium* suspension $OD_{600}$=0.2 for 30 minutes consisting of 1× Murashige and Skoog macronutrients, 1× micronutrients and B5 organic vitamins, supplemented with 500 mg/L MES, 100 µM Acetosyringone, 3% (w/v) sucrose at a pH of 5.8.

Following inoculation, hypocotyl sections are blotted on sterile paper towels and transferred to 9×1.5 cm petri dishes containing 1× Murashige and Skoog macronutrients, 1× micronutrients and B5 organic vitamins, supplemented with 500 mg/L MES, 100 µM Acetosyringone, 1 mg/L 2,4-D, 3% (w/v) sucrose at a pH of 5.8 solidified with 8 g/l Bacto-Agar.

Explants are incubated at 25° C. under 16 h light/8 h dark conditions for 72 hours for co-cultivation.

Following co-cultivation, 20-30 hypocotyl explants are transferred to 9×1.5 cm petri dishes containing a solidified selection medium consisting of 1× Murashige and Skoog macronutrients, 1× micronutrients and B5 organic vitamins, supplemented with 500 mg/L MES, 1 mg/L 2,4-D, 3% (w/v) sucrose at a pH of 5.8 solidified with 8 g/l Bacto-Agar, supplemented with 250 mg/l timentin and 10 mg/l hygromycin to select for hygromycin-resistant shoots. Plates are incubated at 25° C. under 16 h light/8 h dark conditions.

After 7 days hypocotyl explants are transferred to 9×2.0 cm petri dishes containing a solidified regeneration media consisting of 1× Murashige and Skoog macronutrients, 1× micronutrients and B5 organic vitamins, supplemented with 500 mg/L MES, 1 mg/L 2,4-D, 3% (w/v) sucrose at a pH of 5.8 solidified with 8 g/l Bacto-Agar, supplemented with 4 mg/l BAP, 2 mg/l Zeatin, 5 mg/l Silver Nitrate, 250 mg/l timentin and 10 mg/l hygromycin. Plates are incubated under direct light at 25° C. under fluorescent light conditions (16 hr light/8 hr dark photoperiod; 55 µmol m$^{-2}$ sec$^{-1}$) for 4 weeks to encourage shoot development.

Regeneration is monitored weekly and hypocotyl explants transferred to fresh 9×2.0 cm petri dishes containing solidified regeneration media, RM supplemented with 4 mg/l benzyladenine, 2 mg/l zeatin, 5 mg/l silver nitrate, 250 mg/l timentin and 10 mg/l hygromycin for 6-8 weeks to encourage shoot development.

Hygromycin-resistant (Hyg$^r$) shoots are transferred to 120 ml vessels containing solidified root induction medium, RIM1, consisting of 1× Murashige and Skoog macronutrients, 1× micronutrients and B5 organic vitamins, supplemented with 500 mg/L MES, 1 mg/L 2,4-D, 1% (w/v) sucrose at a pH of 5.8 solidified with 8 g/l Bacto-Agar supplemented with 250 mg/l timentin. Shoots are incubated under direct fluorescent light at 25° C. (16 hr light/8 hr dark photoperiod; 55 µmol m$^{-2}$ sec$^{-1}$) to encourage shoot elongation and root development over 4-5 weeks. All Hyg$^r$ shoots with developed shoot and root systems are transferred to soil and grown under glasshouse conditions.

Example 9

Biolistic Transformation of Wheat

*Triticum aestivum* L.

Transformation vectors containing chimeric ipt genes under control of Atmyb32 promoter (FIG. 1) and Atmyb32xs variant promoter sequence with deleted root-specific motifs (FIG. 2) were used for biolistic transformation of wheat (*Triticum aestivum* L. MPB Bobwhite 26). A representative vector is shown in FIG. 24. A schematic of the procedure for biolistic transformation of wheat is outlined in FIG. 27. The transformation procedure includes the following steps:

Step 1 (Donor Plant Production):

*Triticum aestivum* (Bobwhite 26) seed is used for the production of donor plant material. Wheat plants are grown in a nursery mix consisting of composted pine bark, perlite and vermiculite, with five plants per pot to a maximum pot size of 20 cm. Plants are kept under glasshouse conditions at approximately 22-24° C. for 12-16 weeks (FIG. 28A). Once the first spike emerges from the flag leaf, plants are tagged and embryos collected from the tallest heads 12-15 days post anthesis.

Step 2 (Day 1)

Spikes at the desired stage of development are harvested (FIG. 28B). Caryopsis are removed from the spikes and surface sterilised for 20 minutes in a 0.8% (v/v) NaOCl solution and rinsed at least four times in sterile distilled water.

Embryos up to 10 mm in length are aseptically excised from each caryopsis (removing the axis) using a dissecting microscope and cultured axial side down on an osmotic medium (E3maltose) consisting of 2× Murashige and Skoog (1962) macronutrients, 1× micronutrients and organic vitamins, 40 mg/L thiamine, 150 mg/L L-asparagine, supplemented with 15% (w/v) maltose, 0.8% (w/v) Sigma-agar and 2.5 mg/L 2,4-D (FIGS. 28C&D). Embryos are cultured on 60 mm×15 mm clear polypropylene petrie dishes with 15 mL of media. Culture plates are incubated at 24° C. in the dark for 4 hours prior to bombardment. Embryos are bombarded using a BioRad PDS1000 gene gun at 900 psi and at 6 cm with 1 µg of vector plasmid DNA precipitated onto 0.6 µm gold particles. Following bombardment, embryos are incubated overnight in the dark on the osmotic media.

Step 3 (Day 2):

Embryos are transferred to a callus induction medium (E3calli) consisting of 2× Murashige and Skoog (1962) macronutrients and 1× micronutrients and organic vitamins, 40 mg/L thiamine, 150 mg/L L-asparagine, supplemented with 6% (w/v) sucrose, 0.8% (w/v) Sigma-agar and 2.5 mg/L 2,4-D. Embryos are cultured for two weeks at 24° C. in the dark.

Step 4 (Day 16):

After 2 weeks of culture on E3calli, embryos have produced embryogenic callus and are subcultured onto a selection medium (E3Select) consisting of 2× Murashige and Skoog (1962) macronutrients and 1× micronutrients and organic vitamins, 40 mg/L thiamine, 150 mg/L L-asparagine, supplemented with 2% (w/v) sucrose, 0.8% (w/v) Sigma-agar, 5 mg/L of D,L phosphinothricin (PPT) and no plant growth regulators (FIG. 28E-G). Cultures are incubated for further 14 days on E3Select at 24° C. in the light and a 12-hour photoperiod.

Step 5 (Day 30):

After 14 days culture on E3Select, embryogenic callus is sub-cultured onto fresh E3Select for a further 14 days (FIG. 28E-G).

Step 6 (Day 44):

After about 4 weeks on E3Select, developing plantlets are excised from the embryonic callus mass and grown for a further three weeks in 65 mm×80 mm or 65 mm×150 mm polycarbonate tissue culture vessels containing root induction medium (RM). Root induction medium consists of 1× Murashige and Skoog (1962) macronutrients, micronutrients and organic vitamins, 40 mg/L thiamine, 150 mg/L L-asparagine, supplemented with 2% (w/v) sucrose, 0.8% (w/v) Sigma-agar, and 5 mg/L of PPT (FIG. 28H). Remaining embryogenic callus is sub-cultured onto E3Select for another 14 days.

Step 7 (Day 65+):

Regenerated plantlets surviving greater than 3 weeks on RM with healthy root formation are potted into a nursery mix consisting of peat and sand (1:1) and kept at 22-24° C. with elevated humidity under a nursery humidity chamber system (FIG. 28). After two weeks, plants are removed from the humidity chamber and hand watered and liquid fed Aquasol™ weekly until maturity. The $T_0$ plants are sampled for genomic DNA and molecular analysis. $T_1$ seed is collected and planted for high-throughput Q-PCR analysis (FIG. 28J).

Example 10

Agronomic Performance of Transgenic White Clover Plants

The agronomic performance of atmyb32::ipt transgenic white clover (*Trifolium repens*) plants, relative to that of non-transgenic control white clover plants, was evaluated under environmentally controlled growth chamber conditions and in contained field trials (FIG. 29).

Transgenic white clover plants expressing chimeric Atmyb32::ipt genes assessed under controlled growth chamber conditions revealed a significantly enhanced biomass accumulation and reductions in manifestations of senescence, when compared with non-transgenic control white clover plants (FIG. 30). The transgenic white clover plants expressing chimeric Atmyb32::ipt genes showed enhanced total leaf area, increased cumulative leaf area, higher leaf growth dynamics (i.e., number of leaves over time), higher stolon length and increased % flowering plants as well as reduced stolon senescence and death compared with non-transgenic control white clover plants (FIG. 30A-C).

The seed yield performance of 3 independent atmyb32::ipt expressing transgenic white clover plants (i.e., LXR 12, LXR 18 and LXR 11) was also comparatively assessed with non-transgenic control plants (i.e., wild type, WT) under contained field conditions. Two independent atmyb32::ipt expressing transgenic white clover plants (i.e., LXR 12 and LXR 18) with indistinguishable flowering intensity (i.e., number of ripe flowers per m$^2$) to the non-transgenic control plant (i.e., WT) were selected for field evaluation (FIG. 31).

While the seed weight (i.e., weight of thousand seeds) of transgenic white clover plants expressing chimeric Atmyb32::ipt genes (i.e., LXR 12, LXR 18 and LXR 11) was indistinguishable from non-transgenic control white clover plants (i.e., WT) (FIG. 32), the total seed yield expressed on the basis of per flower (FIG. 33), and per area sown (FIG. 34) was doubled in transgenic white clover plants expressing chimeric Atmyb32::ipt genes (i.e., LXR 12 and LXR 18) when compared with non-transgenic control white clover plants of equivalent flowering intensity (i.e., WT).

Example 11

*Agrobacterium*-Mediated Transformation of Alfalfa

*Medicago sativa*

The binary vector pBMVkATMYB32xs::ipt-nos (FIG. 18) containing chimeric ipt genes under control of Atmyb32xs variant promoter sequence with deleted root-specific motifs (FIG. 2) was used for *Agrobacterium*-mediated transformation of *Medicago sativa* petiole explants from highly-regenerable alfalfa (*M. sativa*) clones C2-3, C2-4 and 19-17 (FIG. 35).

Following co-cultivation with *Agrobacterium* tumefaciens strain LBA 4404 harbouring the binary vector pBMVkATMYB32xs::ipt-nos, the alfalfa explants were washed with medium containing cefotaxime and used for induction of embryogenic callus under selective medium containing 25 mg/l kanamycin. Transgenic embryogenic alfalfa calli were recovered and allowed to regenerate transgenic alfalfa shoots, which were transferred on rooting medium leading to the recovery of transgenic alfalfa plants expressing chimeric ipt genes under control of Atmyb32xs variant promoter (FIG. 35).

It will be understood that the invention disclosed and defined in this specification extends to all alternative combinations of two or more of the individual features mentioned or evident from the text or drawings. All of these different combinations constitute various alternative aspects of the invention.

Example 12

Production of Transgenic Canola Plants

Transgenic canola plants (*Brassica napus*) were produced by *Agrobacterium*-mediated transformation using binary vectors (FIGS. 20 and 22) carrying the chimeric atmyb32::ipt gene. The genetic modification has been characterised for the presence of the candidate gene (IP) or the selectable marker (hph) using PCR at the $T_1$ generation (FIG. 36).

FIG. 36 illustrates PCR analysis of transgenic canola plants. Genomic DNA was isolated from different transgenic canola plants of $T_1$ LXR04 lines and subjected to PCR using primers specific for the selectable marker (hph gene) or the candidate gene of interest (IPT). In FIG. 36A hph specific primers were used to amplify a product from genomic DNA and were visualised on an agarose gel. FIG. 36B demonstrates the use of IPT specific primers to amplify genomic DNA using a fluorescent PCR method. The primers are specific for the target sequence which results in detectable fluorescence that is inversely proportional to the amount of accumulated PCR product.

Example 13

IPT Gene Expression in Transgenic Canola Plants

The expression of the atmyb32::ipt transgene in transgenic canola was assessed using a fluorescent RT-PCR method specific for the target sequence (FIG. 37). The IPT mRNA was detected in tissues and relative expression levels were compared among lines and with null controls. Null controls are progeny lines that have undergone the transformation process but do not contain target sequences after crossing.

Example 14

Delayed Detached Leaf Senescence in Transgenic Canola Plants

Experiments were performed to assess detached leaf senescence of atmyb32::ipt transgenic plants. FIGS. 38 to 41 indicate detached senescence assay data associated with expression of the candidate gene in canola. Assays for detached cotyledons and leaves were conducted to induce aging and asses the senescence phenotype of transformed canola as compared to wild-type controls. At day 7 and 14 of the detached senescence assays the progress of senescence was qualitatively scored for each tissue sample as either 0—no possible signs of senescence; 1—first visible signs of senescence with a paling of the green colour: 2—further progression of senescence with yellowing in colour becoming noticeable; 3—the tissue was mostly yellow in colour, however a pale green colour remained evident; 4—progression to completely yellow in colour; 5—yellow in colour with some bleaching and patches of necrosis (FIGS. 39 and 41).

Example 15

Production of Transgenic Wheat Plants

Genetic transformation of wheat was based on biolistic transformation of zygotic embryos from *Triticum aestivum* L Bobwhite 26 wheat line as outlined in FIGS. 27 and 28.

The chimeric atmyb32::ipt gene was inserted into the wheat genome by particle bombardment using whole plasmids so vector backbone sequences may also be incorporated into the genome (FIG. 24).

The transformation vector has been fully sequenced (FIG. 25). The genetic modification has been characterised for the presence of the candidate gene by Southern analysis at the $T_1$ generation (FIG. 42).

FIG. 42 illustrates Southern hybridisation analysis of transgenic wheat plants. Genomic DNA was isolated from different $T_1$ lines of transgenic wheat plants and digested with a restriction enzyme to determine candidate gene copy number. The control is non-transformed wild-type *Triticum aestivum* 'Bobwhite 26'. Digests were electrophoresed, transferred to nylon membrane and probed with a full-length DIG labelled IPT gene, as a probe. A range of copy numbers was observed.

Example 16

IPT Gene Expression in Transgenic Wheat Plants

RNA was extracted from young leaf tissue of glasshouse grown transgenic $T_1$ wheat plants containing the IPT gene driven by the AtMYB32 promoter and first strand cDNA prepared.

Quantitative expression of the transgene was determined using a probe based qRT-PCR method for the target sequence. Representative examples of high, medium and low expressing lines for each of the constructs are presented in FIG. 43. A primer/probe set designed to the endogenous sucrose synthase gene was also used as a control. All amplification plots of the control gene began with in one cycle of each other indicating differences in the level of detection of the GMOs is due to variation in expression.

Both the PCR primers and probe are specific for the target sequence which results in detectable fluorescence that is proportional to the amount of accumulated PCR product. Serially diluted plasmid DNA containing the target sequence being detected was employed to create a standard curve for quantification.

Example 17

Plant Morphology in Transgenic Wheat Plants

Differences in growth characteristics were observed in the glasshouse within and among transgenic wheat lines. The phenotypes predominantly observed among $T_1$ wheat plants included stunted plant height, tillering intensity, leaf number, as well as vegetative biomass (FIG. 44).

Example 18

Delayed Detached Leaf Senescence in Transgenic Wheat Plants

A detached leaf assay was used to asses induced aging and the senescence phenotype of transformed wheat leaves as compared to null controls (FIG. 45). Null controls are progeny lines that have undergone the transformation process but do not contain target sequences after crossing.

Example 19

Analysis of Transgenic Canola Plants

Transgenic T2 canola plants expressing the chimeric atmyb32::ipt transgene showed a higher number of stems, inflorescences, flowers and mature siliques than control plants. FIGS. 46 and 47 show the numbers of stems, inflorescences, flowers and siliques 150 and 225 days after planting for atmyb32::ipt transgenic canola (i.e., LXR lines) compared to the wild type non-transgenic control (WT).

Molecular analysis of T2 transgenic canola lines (i.e., LXR 7.1 lines) expressing the chimeric atmyb32::ipt transgene showed a single copy of the transgene in all analysed lines (FIG. 48).

Analysis of the expression level of the chimeric atmyb32::ipt transgene in T2 transgenic canola lines revealing a range of expression levels in the 6.6-, 7.1- and 8.9-derived lines. LXR 6.6-derived lines showed highest level of expression of the atmyb32::ipt transgene. No expression observed in the wild-type, negative control line (FIG. 49).

T2 transgenic canola lines expressing the chimeric atmyb32::ipt transgene showed up to a 5 fold increase in flower number and up to a 6 fold increase in seed yield when compared to wild-type, negative, non-transgenic controls (FIG. 50).

Analysis of the seed weight (seed weight/100 seeds) showed up to a 30% increase in seed weight in the transgenic canola plants expressing the chimeric atmyb32::ipt transgene relative to the wild-type, negative, non-transgenic control (FIG. 51).

It will also be understood that the term "comprises" (or its grammatical variants) as used in this specification is equivalent to the term "includes" and should not be taken as excluding the presence of other elements or features.

Documents cited in this specification are for reference purposes only and their inclusion is not an acknowledgement that they form part of the common general knowledge in the relevant art.

Finally, it is to be understood that various alterations, modifications and/or additions may be made without departing from the spirit of the present invention as outlined herein.

The invention claimed is:

1. A method of manipulating senescence in a plant or for enhancing plant biomass, said method comprising introducing into said plant a genetic construct comprising a modified myb gene promoter, said modified myb promoter comprising a nucleotide sequence selected from the group consisting of:
   (a) Sequence ID No. 2;
   (b) Sequence ID No. 3;
   (c) Sequence ID No. 4; and
   (d) a functionally active variant of one of the sequences recited in (a), (b) or (c), said functionally active variant having at least approximately 95% identity to Sequence ID No. 2, Sequence ID No. 3 or Sequence ID No. 4;
   said modified myb gene promoter being operatively linked to a cytokinin biosynthesis gene.

2. The method according to claim 1, wherein said myb gene promoter is from *Arabidopsis*.

3. The method according to claim 1, wherein said cytokinin biosynthesis gene is selected from the group consisting of an isopentenyl transferase (ipt) gene and a sho gene.

4. The method according to claim 3, wherein said cytokinin biosynthesis gene is from a genus selected from the group consisting of *Agrobacterium, Lotus* and *Petunia*.

5. The method according to claim 4, wherein said cytokinin biosynthesis gene comprises a nucleotide sequence selected from the group consisting of Sequence ID Nos: 5, 7 and 9, sequences encoding the polypeptides having a sequence of Sequence ID Nos: 6, 8 and 10, and a functionally active variant of the Sequence ID Nos: 5, 7 or 9, said functionally active variant having at least approximately 95% identity to Sequence ID No: 5, Sequence ID No. 7 or Sequence ID No. 9.

6. The method according to claim 1, wherein said genetic construct is introduced into said plant by *Agrobacterium*-mediated or biolistic transformation of plant cells.

7. The method according to claim 6, wherein plant cells incorporating the genetic construct are selected and then cultured to regenerate transformed plants.

8. A method of manipulating senescence in a plant or for enhancing plant biomass, said method comprising introducing into said plant a genetic construct comprising a modified myb gene promoter, said modified myb promoter comprising a nucleotide sequence selected from the group consisting of:
   (a) Sequence ID No. 2;
   (b) Sequence ID No. 3; and
   (c) Sequence ID No. 4;
   said modified myb gene promoter being operatively linked to a cytokinin biosynthesis gene.

9. A vector comprising a modified myb gene promoter, said modified myb gene promoter comprising a nucleotide sequence selected from the group consisting of:
   (a) Sequence ID No. 2;
   (b) Sequence ID No. 3;
   (c) Sequence ID No. 4; and
   (d) a functionally active variant of a sequence recited in (a), (b) or (c), said functionally active variant having at least approximately 95% identity to Sequence ID No. 2, Sequence ID No. 3 or Sequence ID No. 4;
   said modified myb gene promoter being operatively linked to a heterologous cytokinin biosynthesis gene.

10. The vector according to claim 9, further comprising a terminator; said promoter, gene and terminator being operatively linked.

11. The vector according to claim 9, wherein said myb gene promoter is from *Arabidopsis*.

12. The vector according to claim 9, wherein said cytokinin biosynthesis gene is selected from the group consisting of an isopentenyltransferase (ipt) gene and a sho gene.

13. The vector according to claim 12, wherein said cytokinin biosynthesis gene is from a genus selected from the group consisting of *Agrobacterium, Lotus* and *Petunia*.

14. The vector according to claim 9, wherein said cytokinin biosynthesis gene comprises a nucleotide sequence selected from the group consisting of Sequence ID Nos: 5, 7 and 9, sequences encoding the polypeptides having a sequence of Sequence ID Nos: 6, 8 and 10, and a functionally active variant of Sequence ID Nos: 5, 7 or 9, said functionally active variant having at least approximately 95% identity to Sequence ID No: 5, Sequence ID No. 7 or Sequence ID No. 9.

15. A vector comprising a modified myb gene promoter, said modified myb promoter comprising a nucleotide sequence selected from the group consisting of:
   (a) Sequence ID No. 2;
   (b) Sequence ID No. 3; and
   (c) Sequence ID No. 4;
   said modified myb gene promoter being operatively linked to a heterologous cytokinin biosynthesis gene.

16. A transgenic plant cell, plant, plant seed or other plant part, with modified senescence characteristics, said plant cell, plant, plant seed or other plant part comprising a genetic construct comprising a modified myb gene promoter, said modified myb gene promoter comprising a nucleotide sequence selected from the group consisting of:
   (a) Sequence ID No. 2;
   (b) Sequence ID No. 3;
   (c) Sequence ID No. 4; and
   (d) a functionally active variant of a sequence recited in (a), (b) or (c), said functionally active variant having at least approximately 95% identity to Sequence ID No. 2, Sequence ID No. 3 or Sequence ID No. 4;
   said modified myb gene promoter being operatively linked to a cytokinin biosynthesis gene.

17. A transgenic plant cell, plant, plant seed or other plant part derived from the transgenic plant cell according to claim 16.

* * * * *

SEQUENCE LISTING

```
<160> NUMBER OF SEQ ID NOS: 15

<210> SEQ ID NO 1
<211> LENGTH: 941
<212> TYPE: DNA
<213> ORGANISM: Arabidopsis thaliana

<400> SEQUENCE: 1
gtttgtgtct tctagattaa tcctccaaac ttttgattaa ccaaaaaaat tatcaaacta      60
acatgttctc cttttttctt tagaaattct aacgaattta tctttatact gatttgaata     120
tacttaattt ggtcatttgg atgcccttta caacctcctt accaaactca ctatggcaaa     180
tatatactat tttccattgt aacataaatg tccataattt gaattaaatt cgttgcagta     240
cgaaaccatc caactttgtc caaaaacaaa atccttataa ctatttactt taatgtaaat     300
atatcctcta cttttgtttt tacaaccota gctcaaacaa atttattatt tgcgataaaa     360
aatcatatcg aacaaactcg atgattttt ttttcttacg ttattaatga aactaaaata     420
tagaaaaaaa caagatgaac caaattttca cctatctaac tacttaaata taatatgatt     480
aaatttggta aagtttgaaa agtttcttta gaaatgtgaa atattgatca cagtttctat     540
tgctaaaatc accaacaaaa cgcatgtcgc cattcataat tatggtttca cacctacaac     600
taggctaata agtaaataag tagacaacta gactcaggtt tgaaaaaacc ataaaagcca     660
tatgcgtttt tctcattgaa actgcgaaca cgatcgtgtg aatgttgcag tttctagttt     720
tgatacaaac aaacaaaaac acaatttaat cttagattaa aaagaaaaaa gagaacggag     780
cccactagcc actccttcaa acgtgtctta ccaactctct tctagaaaca aattaggctt     840
caccttcctc ttccaacctc tctctctctc tctctctctt tttctcaaac catctctcca     900
taaagcccta atttcttcat cacaagaatc agaagaagaa a                         941

<210> SEQ ID NO 2
<211> LENGTH: 588
<212> TYPE: DNA
<213> ORGANISM: Arabidopsis thaliana

<400> SEQUENCE: 2
```

```
gtttgtgtct tctagattaa tcctccaaac ttttgattaa ccaaaaaaat tatcaaacta      60
acatgttctc cttttttctt tagaaattct aacgaattta tctttatact gatttgaata     120
tacttaattt ggtcatttgg atgccctttta caacctcctt accaaactca ttgatcacag    180
tttctattgc taaaatcacc aacaaaacgc atgtcgccat tcataattat ggtttcacac    240
ctacaactag gctaataagt aaataagtag acaactagac tcaggtttga aaaaccata     300 aaagccatat agcgttttct cattgaaact gcgaacacga tcgtgtgaat gttgcagttt    360
ctagttttga tacaaacaaa caaaaacaca atttaatctt agattaaaaa gaaaaaagag    420
aacggagccc actagccact ccttcaaacg tgtcttacca actctcttct agaaacaaat    480
taggcttcac cttcctcttc caacctctct ctctctctct ctctcttttt ctcaaaccat    540
ctctccataa agccctaatt tcttcatcac aagaatcaga agaagaaa                  588
```

<210> SEQ ID NO 3
<211> LENGTH: 468
<212> TYPE: DNA
<213> ORGANISM: Arabidopsis thaliana

<400> SEQUENCE: 3

```
tacttaattt ggtcatttgg atgccctttta caacctcctt accaaactca ttgatcacag     60
tttctattgc taaaatcacc aacaaaacgc atgtcgccat tcataattat ggtttcacac    120
ctacaactag gctaataagt aaataagtag acaactagac tcaggtttga aaaaccata     180 aaagccatat agcgttttct cattgaaact gcgaacacga tcgtgtgaat gttgcagttt    240
ctagttttga tacaaacaaa caaaaacaca atttaatctt agattaaaaa gaaaaaagag    300
aacggagccc actagccact ccttcaaacg tgtcttacca actctcttct agaaacaaat    360
taggcttcac cttcctcttc caacctctct ctctctctct ctctcttttt ctcaaaccat    420
ctctccataa agccctaatt tcttcatcac aagaatcaga agaagaaa                  468
```

<210> SEQ ID NO 4
<211> LENGTH: 419
<212> TYPE: DNA
<213> ORGANISM: Arabidopsis thaliana

<400> SEQUENCE: 4

```
attgatcaca gtttctattg ctaaaatcac caacaaaacg catgtcgcca ttcataatta     60
tggtttcaca cctacaacta ggctaataag taaataagta gacaactaga ctcaggtttg    120
aaaaaaccat aaaagccata tagcgttttc tcattgaaac tgcgaacacg atcgtgtgaa    180
tgttgcagtt tctagttttg atacaaacaa acaaaaacac aatttaatct tagattaaaa    240
agaaaaaaga gaacggagcc cactagccac tccttcaaac gtgtcttacc aactctcttc    300
tagaaacaaa ttaggcttca ccttcctctt ccaacctctc tctctctctc tctctctttt    360
tctcaaacca tctctccata aagccctaat tcttcatca caagaatcag aagaagaaa     419
```

<210> SEQ ID NO 5
<211> LENGTH: 723
<212> TYPE: DNA
<213> ORGANISM: Agrobacterium tumefaciens

<400> SEQUENCE: 5

```
atggacctgc atctaatttt cggtccaact tgcacaggaa agacgacgac cgcgatagct     60
cttgcccagc agacagggct tccagtcctt tcgcttgatc gggtccaatg ctgtcctcaa    120
ctatcaaccg gaagcggacg accaacagtg gaagaactga aaggaacgac gcgtctctac    180
```

```
cttgatgatc ggcctctggt ggagggtatc atcgcagcca agcaagctca tcataggctg    240
atcgaggagg tgtataatca tgaggccaac ggcgggctta ttcttgaggg aggatccacc    300
tcgttgctca actgcatggc gcgaaacagc tattggagtg cagattttcg ttggcatatt    360
attcgccaca agttacccga ccaagagacc ttcatgaaag cggccaaggc cagagttaag    420
cagatgttgc accccgctgc aggccattct attattcaag agttggttta tctttggaat    480
gaacctcggc tgaggcccat tctgaaagag atcgatggat atcgatatgc catgttgttt    540
gctagccaga accagatcac ggcagatatg ctattgcagc ttgacgcaaa tatggaaggt    600
aagttgatta atgggatcgc tcaggagtat ttcatccatg cgcgccaaca ggaacagaaa    660
ttcccccaag ttaacgcagc cgctttcgac ggattcgaag tcatccgtt cggaatgtat    720 tag                                                                  723
```

<210> SEQ ID NO 6
<211> LENGTH: 240
<212> TYPE: PRT
<213> ORGANISM: Agrobacterium tumefaciens

<400> SEQUENCE: 6

```
Met Asp Leu His Leu Ile Phe Gly Pro Thr Cys Thr Gly Lys Thr Thr
1               5                   10                  15

Thr Ala Ile Ala Leu Ala Gln Gln Thr Gly Leu Pro Val Leu Ser Leu
            20                  25                  30

Asp Arg Val Gln Cys Cys Pro Gln Leu Ser Thr Gly Ser Gly Arg Pro
        35                  40                  45

Thr Val Glu Glu Leu Lys Gly Thr Thr Arg Leu Tyr Leu Asp Asp Arg
    50                  55                  60

Pro Leu Val Glu Gly Ile Ile Ala Ala Lys Gln Ala His His Arg Leu
65                  70                  75                  80

Ile Glu Glu Val Tyr Asn His Glu Ala Asn Gly Gly Leu Ile Leu Glu
                85                  90                  95

Gly Gly Ser Thr Ser Leu Leu Asn Cys Met Ala Arg Asn Ser Tyr Trp
            100                 105                 110

Ser Ala Asp Phe Arg Trp His Ile Ile Arg His Lys Leu Pro Asp Gln
        115                 120                 125

Glu Thr Phe Met Lys Ala Ala Lys Ala Arg Val Lys Gln Met Leu His
    130                 135                 140

Pro Ala Ala Gly His Ser Ile Ile Gln Glu Leu Val Tyr Leu Trp Asn
145                 150                 155                 160

Glu Pro Arg Leu Arg Pro Ile Leu Lys Glu Ile Asp Gly Tyr Arg Tyr
                165                 170                 175

Ala Met Leu Phe Ala Ser Gln Asn Gln Ile Thr Ala Asp Met Leu Leu
            180                 185                 190

Gln Leu Asp Ala Asn Met Glu Gly Lys Leu Ile Asn Gly Ile Ala Gln
        195                 200                 205

Glu Tyr Phe Ile His Ala Arg Gln Gln Glu Gln Lys Phe Pro Gln Val
    210                 215                 220

Asn Ala Ala Ala Phe Asp Gly Phe Glu Gly His Pro Phe Gly Met Tyr
225                 230                 235                 240
```

<210> SEQ ID NO 7
<211> LENGTH: 975
<212> TYPE: DNA
<213> ORGANISM: Lotus japonicus

<400> SEQUENCE: 7

```
atgtccatct caatgctaat gtgcagacta agacaaccct taataaacgt tccctgcagt    60
ggcaaaaaac tgagcatgag gcagattcaa aaggagaagg tagtgttggt gatgggagct   120
acagggacag gaaagtcaaa gctctccatt gacctcgcca cctgtttccc ctcagaaatc   180
atcaactccg acaagattca aatctacgac ggcctcgaca tcgtcaccaa caaaatctcc   240
aaggaagaac aacgtggaat ccccaccac ctcctcggaa ctcaaaaccc taacacagac    300
ttcaccgccg gcgatttcag tgactgttcc accgccgcca ttgacgcaat cacaagccgc   360
gaccaccttc cgatcatcgc cggaggttcg aactcctacc tggaggcgtt aatcgacgac   420
gacgactaca aattccgatc gaggtacgac ttctgctgcc tctgggtcga cgtggcaatg   480
ccggtgctgg actcatacgt ggcggcgcgt gtggatcaga tgctccggag cggaatggtg   540
gaggagctga accgtttttt caacgcgaac ggcgactact cgagaggaat cagaagagcg   600
attggggttc ctgaattcga cgagtatttc cggcgggaag ggttcgccga tgaggaaacg   660
aggaaattgt tactggagcg agcggtgagg gagatgaagg tgaacacgtg caagctcgcg   720
aggaggcaat tggggaagat tcagaggctg aggaatgtga agaggtggga gattcaccgt   780
gttgatgcga cgccggtgtt ttggaagcgt ggggaggagg ctgatgaggc gtggcggaag   840
gtggtggcag agcctagtgc tatgatcgta gcgcagtttc tgtataaggc aaagagtgat   900
gtgaatgttg tttctggcgg tttcagagtg ccggcgggtt caacggagag tgttatggcg   960
gcggcgacgt gttag                                                    975
```

<210> SEQ ID NO 8
<211> LENGTH: 324
<212> TYPE: PRT
<213> ORGANISM: Lotus japonicus

<400> SEQUENCE: 8

```
Met Ser Ile Ser Met Leu Met Cys Arg Leu Arg Gln Pro Leu Ile Asn
  1               5                  10                  15

Val Pro Cys Ser Gly Lys Lys Leu Ser Met Arg Gln Ile Gln Lys Glu
             20                  25                  30

Lys Val Val Leu Val Met Gly Ala Thr Gly Thr Gly Lys Ser Lys Leu
         35                  40                  45

Ser Ile Asp Leu Ala Thr Cys Phe Pro Ser Glu Ile Ile Asn Ser Asp
     50                  55                  60

Lys Ile Gln Ile Tyr Asp Gly Leu Asp Ile Val Thr Asn Lys Ile Ser
 65                  70                  75                  80

Lys Glu Glu Gln Arg Gly Ile Pro His His Leu Leu Gly Thr Gln Asn
                 85                  90                  95

Pro Asn Thr Asp Phe Thr Ala Gly Asp Phe Ser Asp Cys Ser Thr Ala
            100                 105                 110

Ala Ile Asp Ala Ile Thr Ser Arg Asp His Leu Pro Ile Ile Ala Gly
        115                 120                 125

Gly Ser Asn Ser Tyr Leu Glu Ala Leu Ile Asp Asp Asp Tyr Lys
    130                 135                 140

Phe Arg Ser Arg Tyr Asp Phe Cys Cys Leu Trp Val Asp Val Ala Met
145                 150                 155                 160

Pro Val Leu Asp Ser Tyr Val Ala Ala Arg Val Asp Gln Met Leu Arg
                165                 170                 175

Ser Gly Met Val Glu Glu Leu Arg Pro Phe Phe Asn Ala Asn Gly Asp
```

Tyr Ser Arg Gly Ile Arg Arg Ala Ile Gly Val Pro Glu Phe Asp Glu
            180                 185                 190

Tyr Phe Arg Arg Glu Gly Phe Ala Asp Glu Glu Thr Arg Lys Leu Leu
    195                 200                 205

Leu Glu Arg Ala Val Arg Glu Met Lys Val Asn Thr Cys Lys Leu Ala
225                 230                 235                 240

Arg Arg Gln Leu Gly Lys Ile Gln Arg Leu Arg Asn Val Lys Arg Trp
                245                 250                 255

Glu Ile His Arg Val Asp Ala Thr Pro Val Phe Trp Lys Arg Gly Glu
            260                 265                 270

Glu Ala Asp Glu Ala Trp Arg Lys Val Val Ala Glu Pro Ser Ala Met
        275                 280                 285

Ile Val Ala Gln Phe Leu Tyr Lys Ala Lys Ser Asp Val Asn Val Val
            290                 295                 300

Ser Gly Gly Phe Arg Val Pro Ala Gly Ser Thr Glu Ser Val Met Ala
305                 310                 315                 320

Ala Ala Thr Cys

<210> SEQ ID NO 9
<211> LENGTH: 1053
<212> TYPE: DNA
<213> ORGANISM: Petunia x hybrida

<400> SEQUENCE: 9

```
atgttaattg tagtacatat tattagcatc acacgcatca tattcatcac cttaacccat    60
aatcatctcc atttccttat gtttagatca ttatcataca atcacaagca cctcaaattc   120
cttacaaacc cgaccacacg ggtactccga agaaacatgt cgtcatccac tgtagtaaca   180
ataccccggcc ccacacaaaa aaacaaaaac aaaatcatag taataatggg tgcaacaggt   240
tcaggaaaat caaactctc aatagacctc gtcacacgtc actatccttt ttccgaaatc   300
attaactccg acaaaatcca aattaccaaa ggtttaaaca taaccacaaa caaaatcact   360
gtacccgacc gacgtggcgt agttcatcat ttactcggcg agattgaccc cgactttaac   420
ttttctcctt ctcatttccg gtcaattgct ggtcaacgca ttaactccat tattaatcgc   480
cataaactcc cattcctcgt tggtgggtcc aactcatata tctacgcttt attaacaaac   540
cggttcgacc cggatttta ccctgattca aacccggttc attttatatc caacgagtta   600
cgctacaact gttgttttat ttgggtcgat gtattaaacc cggttttgaa tgagtatttg   660
gataaacggg tcgatgagat gatgaactcg ggtatgtatg aagaactgga acagttttt   720
aaagaaaaca ggttttcgga tccgggtttg gaacccggtc gggccaccgg gttgaggaaa   780
gcgatagggg taccggaaat ggagaggtat tttaagaaga gctgtacgta tgaggaagca   840
gtgagggaaa taaagaaaaa cacgtggcgg ttagcgaaga agcagatgtg gaagatccaa   900
cggttgagag aagcagggtg ggacctacaa agagtagatg ccacggaggc atttgtggag   960
gcgatgagta ataagaagga aaagggaatt atttgggaaa acaagtagt ggaaccaagt  1020
gtcaagattg tgaaccgttt tttgttggac tga                              1053
```

<210> SEQ ID NO 10
<211> LENGTH: 350
<212> TYPE: PRT
<213> ORGANISM: Petunia x hybrida

<400> SEQUENCE: 10

```
Met Leu Ile Val Val His Ile Ser Ile Thr Arg Ile Phe Ile
1               5                   10                  15

Thr Leu Thr His Asn His Leu His Phe Leu Met Phe Arg Ser Leu Ser
            20                  25                  30

Tyr Asn His Lys His Leu Lys Phe Leu Thr Asn Pro Thr Thr Arg Val
        35                  40                  45

Leu Arg Arg Asn Met Ser Ser Ser Thr Val Val Thr Ile Pro Gly Pro
    50                  55                  60

Thr Gln Lys Asn Lys Asn Lys Ile Ile Val Ile Met Gly Ala Thr Gly
65                  70                  75                  80

Ser Gly Lys Ser Lys Leu Ser Ile Asp Leu Val Thr Arg His Tyr Pro
                85                  90                  95

Phe Ser Glu Ile Ile Asn Ser Asp Lys Ile Gln Ile Thr Lys Gly Leu
                100                 105                 110

Asn Ile Thr Thr Asn Lys Ile Thr Val Pro Asp Arg Arg Gly Val Val
            115                 120                 125

His His Leu Leu Gly Glu Ile Asp Pro Asp Phe Asn Phe Ser Pro Ser
    130                 135                 140

His Phe Arg Ser Ile Ala Gly Gln Arg Ile Asn Ser Ile Ile Asn Arg
145                 150                 155                 160

His Lys Leu Pro Phe Leu Val Gly Gly Ser Asn Ser Tyr Ile Tyr Ala
                165                 170                 175

Leu Leu Thr Asn Arg Phe Asp Pro Asp Phe Asn Pro Asp Ser Asn Pro
            180                 185                 190

Val His Phe Ile Ser Asn Glu Leu Arg Tyr Asn Cys Cys Phe Ile Trp
    195                 200                 205

Val Asp Val Leu Asn Pro Val Leu Asn Glu Tyr Leu Asp Lys Arg Val
210                 215                 220

Asp Glu Met Met Asn Ser Gly Met Tyr Glu Glu Leu Glu Gln Phe Phe
225                 230                 235                 240

Lys Glu Asn Arg Phe Ser Asp Pro Gly Leu Glu Pro Gly Arg Ala Thr
                245                 250                 255

Gly Leu Arg Lys Ala Ile Gly Val Pro Glu Met Glu Arg Tyr Phe Lys
            260                 265                 270

Lys Ser Cys Thr Tyr Glu Glu Ala Val Arg Gly Ile Lys Glu Asn Thr
        275                 280                 285

Trp Arg Leu Ala Lys Lys Gln Met Trp Lys Ile Gln Arg Leu Arg Glu
    290                 295                 300

Ala Gly Trp Asp Leu Gln Arg Val Asp Ala Thr Glu Ala Phe Val Glu
305                 310                 315                 320

Ala Met Ser Asn Lys Lys Glu Lys Gly Ile Ile Trp Glu Lys Gln Val
                325                 330                 335

Val Glu Pro Ser Val Lys Ile Val Asn Arg Phe Leu Leu Asp
            340                 345                 350

<210> SEQ ID NO 11
<211> LENGTH: 10786
<212> TYPE: DNA
<213> ORGANISM: Artificial
<220> FEATURE:
<223> OTHER INFORMATION: Synthetic construct

<400> SEQUENCE: 11
gtcccgtatc acgcagcgcg tgagctaccc aggcactgcc gccgccggca caaccgttct    60
```

```
tgaatcagaa cccgagggcg acgctgcccg cgaggtccag gcgctggccg ctgaaattaa    120
atcaaaactc atttgagtta atgaggtaaa gagaaaatga gcaaaagcac aaacacgcta    180
agtgccggcc gtccgagcgc acgcagcagc aaggctgcaa cgttggccag cctggcagac    240
acgccagcca tgaagcgggt caactttcag ttgccggcgg aggatcacac caagctgaag    300
atgtacgcgg tacgccaagg caagaccatt accgagctgc tatctgaata catcgcgcag    360
ctaccagagt aaatgagcaa atgaataaat gagtagatga attttagcgg ctaaaggagg    420
cggcatggaa aatcaagaac aaccaggcac cgacgccgtg gaatgcccca tgtgtggagg    480
aacgggcggt tggccaggcg taagcggctg ggttgtctgc cggccctgca atggcactgg    540
aaccccccaag cccgaggaat cggcgtgacg gtcgcaaacc atccggcccg gtacaaatcg    600
gcgcggcgct gggtgatgac ctggtggaga agttgaaggc cgcgcaggcc gcccagcggc    660
aacgcatcga ggcagaagca cgccccggtg aatcgtggca agcggccgct gatcgaatcc    720
gcaaagaatc ccggcaaccg ccggcagccg gtgcgccgtc gattaggaag ccgcccaagg    780
gcgacgagca accagatttt ttcgttccga tgctctatga cgtgggcacc cgcgatagtc    840
gcagcatcat ggacgtggcc gttttccgtc tgtcgaagcg tgaccgacga gctggcgagg    900
tgatccgcta cgagcttcca gacgggcacg tagaggtttc gcagggccg gccggcatgg     960
ccagtgtgtg ggattacgac ctggtactga tggcggtttc ccatctaacc gaatccatga   1020
accgataccg ggaagggaag ggagacaagc ccggccgcgt gttccgtcca cacgttgcgg   1080
acgtactcaa gttctgccgg cgagccgatg gcggaaagca gaaagacgac ctggtagaaa   1140
cctgcattcg gttaaacacc acgcacgttg ccatgcagcg tacgaagaag gccaagaacg   1200
gccgcctggt gacggtatcc gagggtgaag ccttgattag ccgctacaag atcgtaaaga   1260
gcgaaaccgg gcgccggag tacatcgaga tcgagctagc tgattggatg taccgcgaga   1320
tcacagaagg caagaacccg gacgtgctga cggttcaccc cgattacttt ttgatcgatc   1380
ccggcatcgg ccgttttctc taccgcctgg cacgccgcgc gcaggcaag gcagaagcca    1440
gatggttgtt caagacgatc tacgaacgca gtggcagcgc cggagagttc aagaagttct   1500
gtttcaccgt gcgcaagctg atcgggtcaa atgacctgcc ggagtacgat ttgaaggagg   1560
aggcggggca ggctggcccg atcctagtca tgcgctaccg caacctgatc gagggcgaag   1620
catccgccgg ttcctaatgt acggagcaga tgctagggca aattgcccta gcaggggaaa   1680
aaggtcgaaa aggtctcttt cctgtggata gcacgtacat tgggaaccca aagccgtaca   1740
ttgggaaccg gaacccgtac attgggaacc caaagccgta cattgggaac cggtcacaca   1800
tgtaagtgac tgatataaaa gagaaaaaag gcgatttttc cgcctaaaac tctttaaaac   1860
ttattaaaac tcttaaaacc cgcctggcct gtgcataact gtctggccag cgcacagccg   1920
aagagctgca aaaagcgcct acccttcggt cgctgcgctc cctacgcccc gccgcttcgc   1980
gtcggcctat cgcggccgct ggccgctcaa aaatggctgg cctacggcca ggcaatctac   2040
cagggcgcgg acaagccgcg ccgtcgccac tcgaccgccg gcgcccacat caaggcaccc   2100
tgcctcgcgc gtttcggtga tgacggtgaa aacctctgac acatgcagct cccggagacg   2160
gtcacagctt gtctgtaagc ggatgccggg agcagacaag cccgtcaggg cgcgtcagcg   2220
ggtgttggcg ggtgtcgggg cgcagccatg acccagtcac gtagcgatag cggagtgtat   2280
actggcttaa ctatgcggca tcagagcaga ttgtactgag agtgcaccat atgcggtgtg   2340
aaataccgca cagatgcgta aggagaaaat accgcatcag cgctcttccg cttcctcgc    2400
tcactgactc gctgcgctcg gtcgttcggc tgcggcgagc ggtatcagct cactcaaagg   2460
```

```
cggtaatacg gttatccaca gaatcagggg ataacgcagg aaagaacatg tgagcaaaag   2520
gccagcaaaa ggccaggaac cgtaaaaagg ccgcgttgct ggcgtttttc cataggctcc   2580
gcccccctga cgagcatcac aaaaatcgac gctcaagtca gaggtggcga acccgacag    2640 gactataaag ataccaggcg tttccccctg gaagctccct cgtgcgctct cctgttccga   2700
ccctgccgct taccggatac ctgtccgcct ttctcccttc gggaagcgtg gcgctttctc   2760
atagctcacg ctgtaggtat ctcagttcgg tgtaggtcgt tcgctccaag ctgggctgtg   2820
tgcacgaacc ccccgttcag cccgaccgct gcgccttatc cggtaactat cgtcttgagt   2880
ccaacccggt aagacacgac ttatcgccac tggcagcagc cactggtaac aggattagca   2940
gagcgaggta tgtaggcggt gctacagagt tcttgaagtg gtggcctaac tacggctaca   3000
ctagaaggac agtatttggt atctgcgctc tgctgaagcc agttaccttc ggaaaaagag   3060
ttggtagctc ttgatccggc aaacaaacca ccgctggtag cggtggtttt tttgtttgca   3120
agcagcagat tacgcgcaga aaaaaggat ctcaagaaga tcctttgatc ttttctacgg    3180
ggtctgacgc tcagtggaac gaaaactcac gttaagggat tttggtcatg catgatatat   3240
ctcccaattt gtgtagggct tattatgcac gcttaaaaat aataaaagca gacttgacct   3300
gatagtttgg ctgtgagcaa ttatgtgctt agtgcatcta atcgcttgag ttaacgccgg   3360
cgaagcggcg tcggcttgaa cgaatttcta gctagacatt atttgccgac taccttggtg   3420
atctcgcctt tcacgtagtg gacaaattct tccaactgat ctgcgcgcga ggccaagcga   3480
tcttcttctt gtccaagata agcctgtcta gcttcaagta tgacgggctg atactgggcc   3540
ggcaggcgct ccattgccca gtcggcagcg acatccttcg gcgcgatttt gccggttact   3600
gcgctgtacc aaatgcggga caacgtaagc actacatttc gctcatcgcc agcccagtcg   3660
ggcggcgagt tccatagcgt taaggtttca tttagcgcct caaatagatc ctgttcagga   3720
accggatcaa agagttcctc cgccgctgga cctaccaagg caacgctatg ttctcttgct   3780
tttgtcagca agatagccag atcaatgtcg atcgtggctg gctcgaagat acctgcaaga   3840
atgtcattgc gctgccattc tccaaattgc agttcgcgct tagctggata acgccacgga   3900
atgatgtcgt cgtgcacaac aatggtgact tctacagcgc ggagaatctc gctctctcca   3960
ggggaagccg aagtttccaa aaggtcgttg atcaaagctc gccgcgttgt ttcatcaagc   4020
cttacggtca ccgtaaccag caaatcaata tcactgtgtg gcttcaggcc gccatccact   4080
gcggagccgt acaaatgtac ggccagcaac gtcggttcga gatggcgctc gatgacgcca   4140
actacctctg atagttgagt cgatacttcg gcgatcaccg cttcccccat gatgtttaac   4200
tttgttttag ggcgactgcc ctgctgcgta acatcgttgc tgctccataa catcaaacat   4260
cgacccacgg cgtaacgcgc ttgctgcttg gatgcccgag gcatagactg taccccaaaa   4320
aaacatgtca taacaagaag ccatgaaaac cgccactgcg ccgttaccac cgctgcgttc   4380
ggtcaaggtt ctggaccagt tgcgtgacgg cagttacgct acttgcatta cagcttacga   4440
accgaacgag gcttatgtcc actgggttcg tgcccgaatt gatcacaggc agcaacgctc   4500
tgtcatcgtt acaatcaaca tgctaccctc cgcgagatca tccgtgtttc aaacccggca   4560
gcttagttgc cgttcttccg aatagcatcg gtaacatgag caaagtctgc cgccttacaa   4620
cggctctccc gctgacgccg tcccggactg atgggctgcc tgtatcgagt ggtgattttg   4680
tgccgagctg ccggtcgggg agctgttggc tggctggtgg caggatatat tgtggtgtaa   4740
acaaattgac gcttagacaa cttaataaca cattgcggac gtttttaatg tactgaatta   4800
```

```
acgccgaatt gaattcctcg agtacgtagg atccatttaa attctagagg cgcgccgata    4860
tcctctctta aggtagcgag ctcttaatta atagggataa cagggtaatg cggccgcaag    4920
ctaaaacgac ggccagtgaa ttatcaactt tgtatagaaa agttgctctg ccgacagtgg    4980
tcccaaagat ggaccccccac ccacgaggag catcgtggaa aaagaagacg ttccaaccac   5040
gtcttcaaag caagtggatt gatgtgataa catggtggag cacgacactc tcgtctactc    5100
caagaatatc aaagatacag tctcagaaga ccaaagggct attgagactt ttcaacaaag    5160
ggtaatatcg ggaaacctcc tcggattcca ttgcccagct atctgtcact tcatcaaaag    5220
gacagtagaa aaggaaggtg gcacctacaa atgccatcat tgcgataaag gaaaggctat    5280
cgttcaagat gcctctgccg acagtggtcc caaagatgga cccccaccca cgaggagcat    5340
cgtggaaaaa gaagacgttc caaccacgtc ttcaaagcaa gtggattgat gtgatatctc    5400
cactgacgta agggatgacg cacaatccca ctatccttcg caagacccctt cctctatata   5460 aggaagttca tttcatttgg agaggacacg ctgcaagttt gtacaaaaaa gcaggctatg    5520
gcaattacct tatccgcaac ttctttacct atttccgccc ggatccgggc aggttctccg    5580
gccgcttggg tggagaggct attcggctat gactgggcac aacagacaat cggctgctct    5640
gatgccgccg tgttccggct gtcagcgcag gggcgcccgg ttcttttttgt caagaccgac   5700 ctgtccggtg ccctgaatga actgcaggac gaggcagcgc ggctatcgtg gctggccacg    5760
acgggcgttc cttgcgcagc tgtgctcgac gttgtcactg aagcgggaag gactggctg     5820 ctattgggcg aagtgccggg gcaggatctc ctgtcatctc accttgctcc tgccgagaaa    5880
gtatccatca tggctgatgc aatgcggcgg ctgcatacgc ttgatccggc tacctgccca    5940
ttcgaccacc aagcgaaaca tcgcatcgag cgagcacgta ctcggatgga agccggtctt    6000
gtcgatcagg atgatctgga cgaagagcat caggggctcg cgccagccga actgttcgcc    6060
aggctcaagg cgcgcatgcc cgacggcgag gatctcgtcg tgacccatgg cgatgcctgc    6120
ttgccgaata tcatggtgga aaatggccgc ttttctggat tcatcgactg tggccggctg    6180
ggtgtggcgg accgctatca ggacatagcg ttggctaccc gtgatattgc tgaagagctt    6240
ggcggcgaat gggctgaccg cttcctcgtg ctttacggta tcgccgctcc cgattcgcag    6300
cgcatcgcct tctatcgcct tcttgacgag ttcttctgaa cccagctttc ttgtacaaag    6360
tggagtccgc aaaaatcacc agtctctctc tacaaatcta tctctctcta ttttctcca    6420 gaataatgtg tgagtagttc ccagataagg gaattagggt tcttataggg tttcgctcat    6480
gtgttgagca tataagaaac ccttagtatg tatttgtatt tgtaaaatac ttctatcaat    6540
aaaatttcta attcctaaaa ccaaaatcca gtgacctcaa ctttattata catagttgat    6600
aattcactgg ccgtgcttat tccatggctg caggtcgacg aattcaccgg ttagggataa    6660
cagggtaatc gctaccttag gaccgttata gttacggcca gtgccattac cctgttatcc    6720
ctaaccggtg acaactttgt atagaaaagt tggtttgtgt cttctagatt aatcctccaa    6780
acttttgatt aaccaaaaaa attatcaaac taacatgttc tccttttttc tttagaaatt    6840
ctaacgaatt tatctttata ctgatttgaa tatacttaat ttggtcattt ggatgccctt    6900
tacaacctcc ttaccaaact cactatggca aatatatact attttccatt gtaacataaa    6960
tgtccataat ttgaattaaa ttcgttgcag tacgaaacca tccaactttg tccaaaaaca    7020
aaatccttat aactatttac tttaatgtaa atatatcctc tacttttgtt tttacaaccc    7080
tagctcaaac aaatttatta tttgcgataa aaaatcatat cgaacaaact cgatgatttt    7140 tttttttctta cgttattaat gaaactaaaa tatagaaaaa aacaagatga accaaatttt    7200
```

```
cacctatcta actacttaaa tataatatga ttaaatttgg taaagtttga aaagtttctt    7260
tagaaatgtg aaatattgat cacagtttct attgctaaaa tcaccaacaa aacgcatgtc    7320
gccattcata attatggttt cacacctaca actaggctaa taagtaaata agtagacaac    7380
tagactcagg tttgaaaaaa ccataaaagc catatagcgt tttctcattg aaactgcgaa    7440
cacgatcgtg tgaatgttgc agtttctagt tttgatacaa acaaacaaaa acacaattta    7500
atcttagatt aaaaagaaaa aagagaacgg agcccactag ccactccttc aaacgtgtct    7560
taccaactct cttctagaaa caaattaggc ttcaccttcc tcttccaacc tctctctctc    7620
tctctctctc tttttctcaa accatctctc cataaagccc taatttcttc atcacaagaa    7680
tcagaagaag aaacaagttt gtacaaaaaa gcaggcttac tgcaaaaaac ttatggacct    7740
gcatctaatt ttcggtccaa cttgcacagg aaagacgacg accgcgatag ctcttgccca    7800
gcagacaggg cttccagtcc tttcgcttga tcgggtccaa tgctgtcctc aactatcaac    7860
cggaagcgga cgaccaacag tggaagaact gaaaggaacg acgcgtctct accttgatga    7920
tcggcctctg gtgagggta tcatcgcagc caagcaagct catcataggc tgatcgagga    7980
ggtgtataat catgaggcca acggcgggct tattcttgag ggaggatcca cctcgttgct    8040
caactgcatg gcgcgaaaca gctattggag tgcagatttt cgttggcata ttattcgcca    8100
caagttaccc gaccaagaga ccttcatgaa agcggccaag gccagagtta agcagatgtt    8160
gcaccccgct gcaggccatt ctattattca agagttggtt tatctttgga atgaacctcg    8220
gctgaggccc attctgaaag agatcgatgg atatcgatat gccatgttgt ttgctagcca    8280
gaaccagatc acggcagata tgctattgca gcttgacgca aatatggaag gtaagttgat    8340
taatgggatc gctcaggagt atttcatcca tgcgcgccaa caggaacaga aattccccca    8400
agttaacgca gccgctttcg acggattcga aggtcatccg ttcggaatgt attaggtacc    8460
cagctttctt gtacaaagtg ggatcgttca aacatttggc aataaagttt cttaagattg    8520
aatcctgttg ccggtcttgc gatgattatc atataatttc tgttgaatta cgttaagcat    8580
gtaataatta acatgtaatg catgacgtta tttatgagat gggttttat gattagagtc    8640 ccgcaattat acatttaata cgcgatagaa acaaaatat agcgcgcaaa ctaggataaa    8700
ttatcgcgcg cggtgtcatc tatgttacta gatccaactt tattatacat agttgattcg    8760
tcgacctgca gtcgctacct taggaccgtt atagttatgg caaacagcta ttatgggtat    8820
tatgggtggt tctttatgcg gacactgacg gctttatgcc tgcaggtcgc gagcgatcgc    8880
ggtaccgccc gggcgtcgac aggcctaagc ttagcttgag cttggatcag attgtcgttt    8940
cccgccttca gtttaaacta tcagtgtttg acaggatata ttggcgggta aacctaagag    9000
aaaagagcgt ttattagaat aacgatatt taaaagggcg tgaaaaggtt tatccgttcg    9060
tccatttgta tgtgcatgcc aaccacaggg ttcccctcgg gatcaaagta ctttgatcca    9120 accccctccgc tgctatagtg cagtcggctt ctgacgttca gtgcagccgt cttctgaaaa    9180
cgacatgtcg cacaagtcct aagttacgcg acaggctgcc gccctgccct tttcctggcg    9240
ttttcttgtc gcgtgtttta gtcgcataaa gtagaatact tgcgactaga accggagaca    9300
ttacgccatg aacaagagcg ccgccgctgg cctgctgggc tatgcccgcg tcagcaccga    9360
cgaccaggac ttgaccaacc aacgggccga actgcacgcg gccggctgca ccaagctgtt    9420
ttccgagaag atcaccggca ccaggcgcga accgcccgga ctggccagga tgcttgacca    9480
cctacgccct ggcgacgttg tgacagtgac caggctagac cgcctggccc gcagcacccg    9540
```

```
cgacctactg gacattgccg agcgcatcca ggaggccggc gcgggcctgc gtagcctggc    9600
agagccgtgg gccgcacacc accacgccgg cggccgcatg gtgttgaccg tgttcgccgg    9660
cattgccgag ttcgagcgtt ccctaatcat cgaccgcacc cggagcgggc gcgaggccgc    9720
caaggcccga ggcgtgaagt ttggcccccg ccctaccctc accccggcac agatcgcgca    9780
cgcccgcgag ctgatcgacc aggaaggccg caccgtgaaa gaggcggctg cactgcttgg    9840
cgtgcatcgc tcgaccctgt accgcgcact tgagcgcagc gaggaagtga cgcccaccga    9900
ggccaggcgg cgcggtgcct tccgtgagga cgcattgacc gaggccgacg ccctggcggc    9960
cgccgagaat gaacgccaag aggaacaagc atgaaaccgc accaggacgg ccaggacgaa   10020 ccgttttca ttaccgaaga gatcgaggcg gagatgatcg cggccgggta cgtgttcgag    10080
ccgcccgcgc acgtctcaac cgtgcggctg catgaaatcc tggccggttt gtctgatgcc   10140
aagctggcgg cctggccggc cagcttggcc gctgaagaaa ccgagcgccg ccgtctaaaa   10200
aggtgatgtg tatttgagta aaacagcttg cgtcatgcgg tcgctgcgta tatgatgcga   10260
tgagtaaata aacaaatacg caaggggaac gcatgaaggt tatcgctgta cttaaccaga   10320
aaggcgggtc aggcaagacg accatcgcaa cccatctagc ccgcgccctg caactcgccg   10380
gggccgatgt tctgttagtc gattccgatc ccagggcag tgcccgcgat tgggcggccg    10440
tgcgggaaga tcaaccgcta accgttgtcg gcatcgaccg cccgacgatt gaccgcgacg   10500
tgaaggccat cggccggcgc gacttcgtag tgatcgacgg agcgcccag gcggcggact    10560 tggctgtgtc cgcgatcaag gcagccgact tcgtgctgat tccggtgcag ccaagccctt   10620
acgacatatg ggccaccgcc gacctggtgg agctggttaa gcagcgcatt gaggtcacgg   10680
atggaaggct acaagcggcc tttgtcgtgt cgcgggcgat caaaggcacg cgcatcggcg   10740
gtgaggttgc cgaggcgctg ccgggtacg agctgcccat tcttga               10786
```

<210> SEQ ID NO 12
<211> LENGTH: 10468
<212> TYPE: DNA
<213> ORGANISM: Artificial
<220> FEATURE:
<223> OTHER INFORMATION: Synthetic construct

<400> SEQUENCE: 12

```
gtcccgtatc acgcagcgcg tgagctaccc aggcactgcc gccgccggca caaccgttct      60
tgaatcagaa cccgagggcg acgctgcccg cgaggtccag gcgctggccg ctgaaattaa     120
atcaaaactc atttgagtta atgaggtaaa gagaaaatga gcaaaagcac aaacacgcta     180
agtgccggcc gtccgagcgc acgcagcagc aaggctgcaa cgttggccag cctggcagac     240
acgccagcca tgaagcgggt caactttcag ttgccggcgg aggatcacac caagctgaag     300
atgtacgcgg tacgccaagg caagaccatt accgagctgc tatctgaata catcgcgcag     360
ctaccagagt aaatgagcaa atgaataaat gagtagatga attttagcgg ctaaaggagg     420
cggcatggaa aatcaagaac aaccaggcac cgacgccgtg gaatgcccca tgtgtggagg     480
aacgggcggt tggccaggcg taagcggctg ggttgtctgc cggccctgca atggcactgg     540
aacccccaag cccgaggaat cggcgtgacg gtcgcaaacc atccggcccg gtacaaatcg     600
gcgcggcgct gggtgatgac ctggtggaga agttgaaggc cgcgcaggcc gcccagcggc     660
aacgcatcga ggcagaagca cgccccggtg aatcgtggca agcggccgct gatcgaatcc     720
gcaaagaatc ccggcaaccg ccggcagccg gtgcgccgtc gattaggaag ccgcccaagg     780
gcgacgagca accagatttt tcgttccga tgctctatga cgtgggcacc cgcgatagtc     840
```

```
gcagcatcat ggacgtggcc gttttccgtc tgtcgaagcg tgaccgacga gctggcgagg      900
tgatccgcta cgagcttcca gacgggcacg tagaggtttc cgcagggccg gccggcatgg      960
ccagtgtgtg ggattacgac ctggtactga tggcggtttc ccatctaacc gaatccatga     1020
accgataccg ggaagggaag ggagacaagc ccggccgcgt gttccgtcca cacgttgcgg     1080
acgtactcaa gttctgccgg cgagccgatg gcggaaagca gaaagacgac ctggtagaaa     1140
cctgcattcg gttaaacacc acgcacgttg ccatgcagcg tacgaagaag gccaagaacg     1200
gccgcctggt gacggtatcc gagggtgaag ccttgattag ccgctacaag atcgtaaaga     1260
gcgaaaccgg gcgccggag tacatcgaga tcgagctagc tgattggatg taccgcgaga     1320
tcacagaagg caagaacccg gacgtgctga cggttcaccc cgattacttt ttgatcgatc     1380
ccggcatcgg ccgttttctc taccgcctgg cacgccgcgc cgcaggcaag cagaagccca     1440
gatggttgtt caagacgatc tacgaacgca gtggcagcgc cggagagttc aagaagttct     1500
gtttcaccgt gcgcaagctg atcgggtcaa atgacctgcc ggagtacgat ttgaaggagg     1560
aggcggggca ggctggcccg atcctagtca tgcgctaccg caacctgatc gagggcgaag     1620
catccgccgg ttcctaatgt acggagcaga tgctagggca aattgcccta gcaggggaaa     1680
aaggtcgaaa aggtctcttt cctgtggata gcacgtacat tgggaaccca agccgtaca     1740 ttgggaaccg gaacccgtac attgggaacc caaagccgta cattgggaac cggtcacaca     1800
tgtaagtgac tgatataaaa gagaaaaaag gcgattttc cgcctaaaac tctttaaaac     1860
ttattaaaac tcttaaaacc cgcctggcct gtgcataact gtctggccag cgcacagccg     1920
aagagctgca aaaagcgcct acccttcggt cgctgcgctc cctacgcccc gccgcttcgc     1980
gtcggcctat cgcggccgct ggccgctcaa aaatggctgg cctacggcca ggcaatctac     2040
cagggcgcgg acaagccgcg ccgtcgccac tcgaccgccg gcgcccacat caaggcaccc     2100
tgcctcgcgc gtttcggtga tgacggtgaa aacctctgac acatgcagct cccggagacg     2160
gtcacagctt gtctgtaagc ggatgccggg agcagacaag cccgtcaggg cgcgtcagcg     2220
ggtgttggcg ggtgtcgggg cgcagccatg acccagtcac gtagcgatag cggagtgtat     2280
actggcttaa ctatgcggca tcagagcaga ttgtactgag agtgcaccat atgcggtgtg     2340
aaataccgca cagatgcgta aggagaaaat accgcatcag gcgctcttcc gcttcctcgc     2400
tcactgactc gctgcgctcg tcgttcggc tgcggcgagc ggtatcagct cactcaaagg     2460
cggtaatacg gttatccaca gaatcagggg ataacgcagg aaagaacatg tgagcaaaag     2520
gccagcaaaa ggccaggaac cgtaaaaagg ccgcgttgct ggcgtttttc cataggctcc     2580
gcccccctga cgagcatcac aaaaatcgac gctcaagtca gaggtggcga aacccgacag     2640
gactataaag ataccaggcg tttccccctg gaagctccct cgtgcgctct cctgttccga     2700
ccctgccgct taccggatac ctgtccgcct ttctccctte gggaagcgtg cgctttctc      2760 atagctcacg ctgtaggtat ctcagttcgg tgtaggtcgt tcgctccaag ctgggctgtg     2820
tgcacgaacc ccccgttcag cccgaccgct gcgccttatc cggtaactat cgtcttgagt     2880
ccaacccggt aagacacgac ttatcgccac tggcagcagc cactggtaac aggattagca     2940
gagcgaggta tgtaggcggt gctacagagt tcttgaagtg gtggcctaac tacggctaca     3000
ctagaaggac agtatttggt atctgcgctc tgctgaagcc agttaccttc ggaaaaagag     3060
ttggtagctc ttgatccggc aaacaaacca ccgctggtag cggtggtttt tttgtttgca     3120
agcagcagat tacgcgcaga aaaaaaggat ctcaagaaga tcctttgatc ttttctacgg     3180
```

```
ggtctgacgc tcagtggaac gaaaactcac gttaagggat tttggtcatg catgatatat    3240
ctcccaattt gtgtagggct tattatgcac gcttaaaaat aataaaagca gacttgacct    3300
gatagtttgg ctgtgagcaa ttatgtgctt agtgcatcta atcgcttgag ttaacgccgg    3360
cgaagcggcg tcggcttgaa cgaatttcta gctagacatt attttgccgac taccttggtg   3420
atctcgcctt tcacgtagtg gacaaattct tccaactgat ctgcgcgcga ggccaagcga    3480
tcttcttctt gtccaagata agcctgtcta gcttcaagta tgacgggctg atactgggcc    3540
ggcaggcgct ccattgccca gtcggcagcg acatccttcg gcgcgatttt gccggttact    3600
gcgctgtacc aaatgcggga caacgtaagc actacatttc gctcatcgcc agcccagtcg    3660
ggcggcgagt tccatagcgt taaggtttca tttagcgcct caaatagatc ctgttcagga    3720
accggatcaa agagttcctc cgccgctgga cctaccaagg caacgctatg ttctcttgct    3780
tttgtcagca agatagccag atcaatgtcg atcgtggctg gctcgaagat acctgcaaga    3840
atgtcattgc gctgccattc tccaaattgc agttcgcgct tagctggata acgccacgga    3900
atgatgtcgt cgtgcacaac aatggtgact tctacagcgc ggagaatctc gctctctcca    3960
ggggaagccg aagtttccaa aaggtcgttg atcaaagctc gccgcgttgt ttcatcaagc    4020
cttacggtca ccgtaaccag caaatcaata tcactgtgtg gcttcaggcc gccatccact    4080
gcggagccgt acaaatgtac ggccagcaac gtcggttcga gatggcgctc gatgacgcca    4140
actacctctg atagttgagt cgatacttcg gcgatcaccg cttccccat gatgtttaac     4200
tttgttttag ggcgactgcc ctgctgcgta acatcgttgc tgctccataa catcaaacat    4260
cgacccacgg cgtaacgcgc ttgctgcttg gatgcccgag gcatagactg tacccccaaa    4320
aaacatgtca taacaagaag ccatgaaaac cgccactgcg ccgttaccac cgctgcgttc    4380
ggtcaaggtt ctggaccagt tgcgtgacgg cagttacgct acttgcatta cagcttacga    4440
accgaacgag gcttatgtcc actgggttcg tgcccgaatt gatcacaggc agcaacgctc    4500
tgtcatcgtt acaatcaaca tgctaccctc cgcgagatca tccgtgtttc aaacccggca    4560
gcttagttgc cgttcttccg aatagcatcg gtaacatgag caaagtctgc cgccttacaa    4620
cggctctccc gctgacgccg tcccggactg atgggctgcc tgtatcgagt ggtgattttg    4680
tgccgagctg ccggtcgggg agctgttggc tggctggtgg caggatatat tgtggtgtaa    4740
acaaattgac gcttagacaa cttaataaca cattgcggac gttttttaatg tactgaatta   4800
acgccgaatt gaattcctcg agtacgtagg atccatttaa attctagagg cgcgccgata    4860
tcctctctta aggtagcgag ctcttaatta ataggggataa cagggtaatg cggccgcaag    4920
ctaaaacgac ggccagtgaa ttatcaactt tgtatagaaa agttgctctg ccgacagtgg    4980
tcccaaagat ggacccccac ccacgaggag catcgtggaa aaagaagacg ttccaaccac    5040
gtcttcaaag caagtggatt gatgtgataa catggtggag cacgacactc tcgtctactc    5100
caagaatatc aaagatacag tctcagaaga ccaaagggct attgagactt ttcaacaaag    5160
ggtaatatcg ggaaacctcc tcggattcca ttgcccagct atctgtcact tcatcaaaag    5220
gacagtagaa aaggaaggtg gcacctacaa atgccatcat tgcgataaag gaaaggctat    5280
cgttcaagat gcctctgccg acagtggtcc caaagatgga cccccaccca cgaggagcat    5340
cgtggaaaaa gaagacgttc caaccacgtc ttcaaagcaa gtggattgat gtgatatctc    5400
cactgacgta agggatgacg cacaatccca ctatccttcg caagaccctt cctctatata    5460
aggaagttca tttcatttgg agaggacacg ctgcaagttt gtacaaaaaa gcaggctatg    5520
gcaattacct tatccgcaac ttctttacct atttccgccc ggatccgggc aggttctccg    5580
```

```
gccgcttggg tggagaggct attcggctat gactgggcac aacagacaat cggctgctct    5640
gatgccgccg tgttccggct gtcagcgcag gggcgcccgg ttcttttttgt caagaccgac    5700
ctgtccggtg ccctgaatga actgcaggac gaggcagcgc ggctatcgtg gctggccacg    5760
acgggcgttc cttgcgcagc tgtgctcgac gttgtcactg aagcgggaag ggactggctg    5820
ctattgggcg aagtgccggg gcaggatctc ctgtcatctc accttgctcc tgccgagaaa    5880
gtatccatca tggctgatgc aatgcggcgg ctgcatacgc ttgatccggc tacctgccca    5940
ttcgaccacc aagcgaaaca tcgcatcgag cgagcacgta ctcggatgga agccggtctt    6000
gtcgatcagg atgatctgga cgaagagcat caggggctcg cgccagccga actgttcgcc    6060
aggctcaagg cgcgcatgcc cgacggcgag gatctcgtcg tgacccatgg cgatgcctgc    6120
ttgccgaata tcatggtgga aaatggccgc ttttctggat tcatcgactg tggccggctg    6180
ggtgtggcgg accgctatca ggacatagcg ttggctaccc gtgatattgc tgaagagctt    6240
ggcggcgaat gggctgaccg cttcctcgtg ctttacggta tcgccgctcc cgattcgcag    6300
cgcatcgcct tctatcgcct tcttgacgag ttcttctgaa cccagctttc ttgtacaaag    6360
tggagtccgc aaaaatcacc agtctctctc tacaaatcta tctctctcta tttttctcca    6420
gaataatgtg tgagtagttc ccagataagg gaattagggt tcttataggg tttcgctcat    6480
gtgttgagca tataagaaac ccttagtatg tatttgtatt tgtaaaatac ttctatcaat    6540
aaaatttcta attcctaaaa ccaaaatcca gtgacctcaa ctttattata catagttgat    6600
aattcactgg ccgtgcttat tccatggctg caggtcgacg aattcaccgg ttagggataa    6660
cagggtaata actataacgg tcctaaggta gcgagcggcc gcaagctaaa acgacggcca    6720
gtgaattatc aactttgtat agaaaagttg gtttgtgtct tctagattaa tcctccaaac    6780
ttttgattaa ccaaaaaaat tatcaaacta acatgttctc cttttttctt tagaaattct    6840
aacgaattta tctttatact gatttgaata tacttaattt ggtcatttgg atgcccttta    6900
caacctcctt accaaaatat tgatcacagt ttctattgct aaaatcacca acaaaacgca    6960
tgtcgccatt cataattatg gtttcacacc tacaactagg ctaataagta aataagtaga    7020
caactagact caggtttgaa aaaaccataa aagccatata gcgttttctc attgaaactg    7080
cgaacacgat cgtgtgaatg ttgcagtttc tagttttgat acaaacaaac aaaaacacaa    7140
tttaatctta gattaaaaag aaaaaagaga acggagccca ctagccactc cttcaaacgt    7200
gtcttaccaa ctctcttcta gaaacaaatt aggcttcacc ttcctcttcc aacctctctc    7260
tctctctctc tctctctttc tcaaaccatc tctccataaa gccctaattt cttcatcaca    7320
agaatcagaa gaagaaacaa gtttgtacaa aaaagcaggc ttactgcaaa aaacttatgg    7380
acctgcatct aattttcggt ccaacttgca caggaaagac gacgaccgcg atagctcttg    7440
cccagcagac agggcttcca gtcctttcgc ttgatcgggt ccaatgctgt cctcaactat    7500
caaccggaag cggacgacca acagtggaag aactgaaagg aacgacgcgt ctctaccttg    7560
atgatcggcc tctggtggag ggtatcatcg cagccaagca agctcatcat aggctgatcg    7620
aggaggtgta taatcatgag gccaacggcg ggcttattct tgagggagga tccacctcgt    7680
tgctcaactg catggcgcga aacagctatt ggagtgcaga ttttcgttgg catattattc    7740
gccacaagtt acccgaccaa gagaccttca tgaaagcggc caaggccaga gttaagcaga    7800
tgttgcaccc cgctgcaggc cattctatta ttcaagagtt ggtttatctt tggaatgaac    7860
ctcggctgag gcccattctg aaagagatcg atggatatcg atatgccatg ttgtttgcta    7920
```

```
gccagaacca gatcacggca gatatgctat tgcagcttga cgcaaatatg gaaggtaagt    7980
tgattaatgg gatcgctcag gagtatttca tccatgcgcg ccaacaggaa cagaaattcc    8040
cccaagttaa cgcagccgct ttcgacggat tcgaaggtca tccgttcgga atgtattagg    8100
tacccagctt tcttgtacaa agtgggatcg ttcaaacatt tggcaataaa gtttcttaag    8160
attgaatcct gttgccggtc ttgcgatgat tatcatataa tttctgttga attacgttaa    8220
gcatgtaata attaacatgt aatgcatgac gttatttatg agatgggttt ttatgattag    8280
agtcccgcaa ttatacattt aatacgcgat agaaaacaaa atatagcgcg caaactagga    8340
taaattatcg cgcgcggtgt catctatgtt actagatcca actttattat acatagttga    8400
taattcactg gccgtcgctt attccatggc tgcaggtcga cgaattcacc ggttaactat    8460
aacggtccta aggtagcgat ggcaaacagc tattatgggt attatgggtg gttctttatg    8520
cggacactga cggctttatg cctgcaggtc gcgagcgatc gcggtaccgc ccgggcgtcg    8580
acaggcctaa gcttagcttg agcttggatc agattgtcgt ttcccgcctt cagtttaaac    8640
tatcagtgtt tgacaggata tattggcggg taaacctaag agaaagagc gtttattaga    8700 ataacggata tttaaagggg cgtgaaaagg tttatccgtt cgtccatttg tatgtgcatg    8760
ccaaccacag ggttcccctc gggatcaaag tactttgatc caacccctcc gctgctatag    8820
tgcagtcggc ttctgacgtt cagtgcagcc gtcttctgaa aacgacatgt cgcacaagtc    8880
ctaagttacg cgacaggctg ccgccctgcc cttttcctgg cgtttttcttg tcgcgtgttt    8940 tagtcgcata aagtagaata cttgcgacta gaaccggaga cattacgcca tgaacaagag    9000
cgccgccgct ggcctgctgg gctatgcccg cgtcagcacc gacgaccagg acttgaccaa    9060
ccaacgggcc gaactgcacg cggccggctg caccaagctg ttttccgaga agatcaccgg    9120
caccaggcgc gaccgcccgg agctggccag gatgcttgac cacctacgcc ctggcgacgt    9180
tgtgacagtg accaggctag accgcctggc ccgcagcacc cgcgacctac tggacattgc    9240
cgagcgcatc caggaggccg gcgcgggcct gcgtagcctg gcagagccgt gggccgacac    9300
caccacgccg gccggccgca tggtgttgac cgtgttcgcc ggcattgccg agttcgagcg    9360
ttccctaatc atcgaccgca cccggagcgg gcgcgaggcc gccaaggccc gaggcgtgaa    9420
gtttggcccc cgccctaccc tcaccccggc acagatcgcg cacgcccgcg agctgatcga    9480
ccaggaaggc cgcaccgtga agaggcggc tgcactgctt ggcgtgcatc gctcgaccct    9540
gtaccgcgca cttgagcgca gcgaggaagt gacgcccacc gaggccaggc ggcgcggtgc    9600
cttccgtgag gacgcattga ccgaggccga cgccctggcg gccgccgaga atgaacgcca    9660
agaggaacaa gcatgaaacc gcaccaggac ggccaggacg aaccgttttt cattaccgaa    9720
gagatcgagg cggagatgat cgcggccggg tacgtgttcg agccgcccgc gcacgtctca    9780
accgtgcggc tgcatgaaat cctggccggt ttgtctgatg ccaagctggc ggcctggccg    9840
gccagcttgg ccgctgaaga aaccgagcgc cgccgtctaa aaggtgatg tgtatttgag    9900 taaaacagct tgcgtcatgc ggtcgctgcg tatatgatgc gatgagtaaa taaacaaata    9960
cgcaagggga acgcatgaag gttatcgctg tacttaacca gaaaggcggg tcaggcaaga    10020
cgaccatcgc aacccatcta gcccgcgccc tgcaactcgc cggggccgat gttctgttag    10080
tcgattccga tcccaggc agtgcccgcg attgggcggc cgtgcgggaa gatcaaccgc    10140
taaccgttgt cggcatcgac cgcccgacga ttgaccgcga cgtgaaggcc atcggccggc    10200
gcgacttcgt agtgatcgac ggagcgcccc aggcggcgga cttggctgtg tccgcgatca    10260
aggcagccga cttcgtgctg attccggtgc agccaagccc ttacgacata tgggccaccg    10320
```

-continued

```
ccgacctggt ggagctggtt aagcagcgca ttgaggtcac ggatggaagg ctacaagcgg    10380
cctttgtcgt gtcgcgggcg atcaaaggca cgcgcatcgg cggtgaggtt gccgaggcgc    10440
tggccgggta cgagctgccc attcttga                                      10468
```

<210> SEQ ID NO 13
<211> LENGTH: 11000
<212> TYPE: DNA
<213> ORGANISM: Artificial
<220> FEATURE:
<223> OTHER INFORMATION: Synthetic construct

<400> SEQUENCE: 13

```
gtcccgtatc acgcagcgcg tgagctaccc aggcactgcc gccgccggca caccgttct      60 tgaatcagaa cccgagggcg acgctgcccg cgaggtccag cgcgtggccg ctgaaattaa    120
atcaaaactc atttgagtta atgaggtaaa gagaaaatga gcaaaagcac aaacacgcta    180
agtgccggcc gtccgagcgc acgcagcagc aaggctgcaa cgttggccag cctggcagac    240
acgccagcca tgaagcgggt caactttcag ttgccggcgg aggatcacac caagctgaag    300
atgtacgcgg tacgccaagg caagaccatt accgagctgc tatctgaata catcgcgcag    360
ctaccagagt aaatgagcaa atgaataaat gagtagatga tttttagcgg ctaaaggagg    420
cggcatggaa aatcaagaac aaccaggcac cgacgccgtg gaatgcccca tgtgtggagg    480
aacgggcggt tggccaggcg taagcggctg ggttgtctgc cggccctgca atggcactgg    540 aaccccaag cccgaggaat cggcgtgacg gtcgcaaacc atccggcccg gtacaaatcg    600
gcgcggcgct gggtgatgac ctggtggaga agttgaaggc cgcgcaggcc gcccagcggc    660
aacgcatcga ggcagaagca cgccccggtg aatcgtggca agcggccgct gatcgaatcc    720
gcaaagaatc ccggcaaccg ccggcagccg gtgcgccgtc gattaggaag ccgcccaagg    780
gcgacgagca accagatttt tcgttccga tgctctatga cgtgggcacc cgcgatagtc    840
gcagcatcat ggacgtggcc gttttccgtc tgtcgaagcg tgaccgacga gctggcgagg    900
tgatccgcta cgagcttcca gacgggcacg tagaggtttc cgcagggccg gccggcatgg    960
ccagtgtgtg ggattacgac ctggtactga tggcggtttc ccatctaacc gaatccatga    1020
accgataccg ggaagggaag ggagacaagc ccggccgcgt gttccgtcca cacgttgcgg    1080
acgtactcaa gttctgccgg cgagccgatg gcggaaagca gaaagacgac ctggtagaaa    1140
cctgcattcg gttaaacacc acgcacgttg ccatgcagcg tacgaagaag gccaagaacg    1200
gccgcctggt gacggtatcc gagggtgaag ccttgattag ccgctacaag atcgtaaaga    1260
gcgaaaccgg cggccggag tacatcgaga tcgagctagc tgattggatg taccgcgaga    1320
tcacagaagg caagaacccg gacgtgctga cggttcaccc cgattacttt ttgatcgatc    1380
ccggcatcgg ccgttttctc taccgcctgg cacgccgcgc cgcaggcaag gcagaagcca    1440
gatggttgtt caagacgatc tacgaacgca gtggcagcgc cggagagttc aagaagttct    1500
gtttcaccgt gcgcaagctg atcgggtcaa atgacctgcc ggagtacgat ttgaaggagg    1560
aggcggggca ggctggcccg atcctagtca tgcgctaccg caacctgatc gagggcgaag    1620
catccgccgg ttcctaatgt acggagcaga tgctagggca aattgcccta gcaggggaaa    1680
aaggtcgaaa aggtctcttt cctgtggata gcacgtacat tgggaaccca agccgtaca    1740 ttgggaaccg gaacccgtac attgggaacc caaagccgta cattgggaac cggtcacaca    1800
tgtaagtgac tgatataaaa gagaaaaaag gcgatttttc cgcctaaaac tctttaaaac    1860
```

-continued

```
ttattaaaac tcttaaaacc cgcctggcct gtgcataact gtctggccag cgcacagccg    1920
aagagctgca aaaagcgcct acccttcggt cgctgcgctc cctacgcccc gccgcttcgc    1980
gtcggcctat cgcggccgct ggccgctcaa aaatggctgg cctacggcca ggcaatctac    2040
cagggcgcgg acaagccgcg ccgtcgccac tcgaccgccg gcgcccacat caaggcaccc    2100
tgcctcgcgc gtttcggtga tgacggtgaa aacctctgac acatgcagct cccggagacg    2160
gtcacagctt gtctgtaagc ggatgccggg agcagacaag cccgtcaggg cgcgtcagcg    2220
ggtgttggcg ggtgtcgggg cgcagccatg acccagtcac gtagcgatag cggagtgtat    2280
actggcttaa ctatgcggca tcagagcaga ttgtactgag agtgcaccat atgcggtgtg    2340
aaataccgca cagatgcgta aggagaaaat accgcatcag gcgctcttcc gcttcctcgc    2400
tcactgactc gctgcgctcg gtcgttcggc tgcggcgagc ggtatcagct cactcaaagg    2460
cggtaatacg gttatccaca gaatcagggg ataacgcagg aaagaacatg tgagcaaaag    2520
gccagcaaaa ggccaggaac cgtaaaaagg ccgcgttgct ggcgtttttc cataggctcc    2580
gcccccctga cgagcatcac aaaaatcgac gctcaagtca gaggtggcga aacccgacag    2640
gactataaag ataccaggcg tttccccctg gaagctccct cgtgcgctct cctgttccga    2700
ccctgccgct taccggatac ctgtccgcct ttctcccttc gggaagcgtg gcgctttctc    2760
atagctcacg ctgtaggtat ctcagttcgg tgtaggtcgt tcgctccaag ctgggctgtg    2820
tgcacgaacc ccccgttcag cccgaccgct gcgccttatc cggtaactat cgtcttgagt    2880
ccaacccggt aagacacgac ttatcgccac tggcagcagc cactggtaac aggattagca    2940
gagcgaggta tgtaggcggt gctacagagt tcttgaagtg gtggcctaac tacggctaca    3000
ctagaaggac agtatttggt atctgcgctc tgctgaagcc agttaccttc ggaaaaagag    3060
ttggtagctc ttgatccggc aaacaaacca ccgctggtag cggtggtttt tttgtttgca    3120
agcagcagat tacgcgcaga aaaaaggat ctcaagaaga tcctttgatc ttttctacgg    3180
ggtctgacgc tcagtggaac gaaaactcac gttaagggat tttggtcatg catgatatat    3240
ctcccaattt gtgtagggct tattatgcac gcttaaaaat aataaaagca gacttgacct    3300
gatagtttgg ctgtgagcaa ttatgtgctt agtgcatcta atcgcttgag ttaacgccgg    3360
cgaagcggcg tcggcttgaa cgaatttcta gctagacatt atttgccgac taccttggtg    3420
atctcgcctt tcacgtagtg gacaaattct ccaactgat ctgcgcgcga ggccaagcga    3480
tcttcttctt gtccaagata agcctgtcta gcttcaagta tgacgggctg atactgggcc    3540
ggcaggcgct ccattgccca gtcggcagcg acatccttcg gcgcgatttt gccggttact    3600
gcgctgtacc aaatgcggga caacgtaagc actacatttc gctcatcgcc agcccagtcg    3660
ggcggcgagt tccatagcgt taaggtttca tttagcgcct caaatagatc ctgttcagga    3720
accggatcaa agagttcctc cgccgctgga cctaccaagg caacgctatg ttctcttgct    3780
tttgtcagca agatagccag atcaatgtcg atcgtggctg gctcgaagat acctgcaaga    3840
atgtcattgc gctgccattc tccaaattgc agttcgcgct tagctggata acgccacgga    3900
atgatgtcgt cgtgcacaac aatggtgact tctacagcgc ggagaatctc gctctctcca    3960
ggggaagccg aagtttccaa aaggtcgttg atcaaagctc gccgcgttgt ttcatcaagc    4020
cttacggtca ccgtaaccag caaatcaata tcactgtgtg gcttcaggcc gccatccact    4080
gcggagccgt acaaatgtac ggccagcaac gtcggttcga gatggcgctc gatgacgcca    4140
actacctctg atagttgagt cgatacttcg gcgatcaccg cttcccccat gatgtttaac    4200
tttgttttag ggcgactgcc ctgctgcgta acatcgttgc tgctccataa catcaaacat    4260
```

```
cgacccacgg cgtaacgcgc ttgctgcttg gatgcccgag gcatagactg tacccccaaaa    4320 aaacatgtca taacaagaag ccatgaaaac cgccactgcg ccgttaccac cgctgcgttc    4380
ggtcaaggtt ctggaccagt tgcgtgacgg cagttacgct acttgcatta cagcttacga    4440
accgaacgag gcttatgtcc actgggttcg tgcccgaatt gatcacaggc agcaacgctc    4500
tgtcatcgtt acaatcaaca tgctaccctc cgcgagatca tccgtgtttc aaacccggca    4560
gcttagttgc cgttcttccg aatagcatcg gtaacatgac caaagtctgc cgccttacaa    4620
cggctctccc gctgacgccg tcccggactg atgggctgcc tgtatcgagt ggtgattttg    4680
tgccgagctg ccggtcgggg agctgttggc tggctggtgg caggatatat tgtggtgtaa    4740
acaaattgac gcttagacaa cttaataaca cattgcggac gtttttaatg tactgaatta    4800
acgccgaatt gaattcctcg agtacgtagg atccatttaa attctagagg cgcgccgata    4860
tcctctctta aggtagcgag ctcttaatta atagggataa cagggtaatg cggccgcaag    4920
ctaaaacgac ggccagtgaa ttatcaactt tgtatagaaa agttgctctg ccgacagtgg    4980
tcccaaagat ggaccccccac ccacgaggag catcgtggaa aagaagacg ttccaaccac    5040 gtcttcaaag caagtggatt gatgtgataa catggtggag cacgcactc tcgtctactc    5100 caagaatatc aaagatacag tctcagaaga ccaaagggct attgagactt ttcaacaaag    5160
ggtaatatcg ggaacctcc tcggattcca ttgcccagct atctgtcact tcatcaaaag    5220
gacagtagaa aaggaaggtg gcacctacaa atgccatcat tgcgataaag gaaaggctat    5280
cgttcaagat gcctctgccg acagtggtcc caaagatgga ccccaccca cgaggagcat    5340 cgtggaaaaa gaagacgttc caaccacgtc ttcaaagcaa gtggattgat gtgatatctc    5400
cactgacgta agggatgacg cacaatccca ctatccttcg caagacccctt cctctatata    5460 aggaagttca tttcatttgg agaggacacg ctgcaagttt gtacaaaaaa gcaggctaga    5520 ccgggggca atgagatatg aaaaagcctg aactcaccgc gacgtctgtc gagaagtttc    5580
tgatcgaaaa gttcgacagc gtctccgacc tgatgcagct ctcggagggc gaagaatctc    5640
gtgctttcag cttcgatgta ggagggcgtg gatatgtcct gcgggtaaat agctgcgccg    5700
atggtttcta caaagatcgt tatgtttatc ggcactttgc atcggccgcg ctcccgattc    5760
cggaagtgct tgacattggg gaattcagcg agagcctgac ctattgcatc tccccgccgtg    5820 cacagggtgt cacgttgcaa gacctgcctg aaaccgaact gcccgctgtt ctgcagccgg    5880
tcgcggaggc catggatgcg atcgctgcgg ccgatcttag ccagacgagc gggttcggcc    5940
cattcggacc gcaaggaatc ggtcaataca ctacatggcg tgatttcata tgcgcgattg    6000
ctgatcccca tgtgtatcac tggcaaactg tgatggacga caccgtcagt gcgtccgtcg    6060
cgcaggctct cgatgagctg atgctttggg ccgaggactg ccccgaagtc cggcacctcg    6120
tgcacgcgga tttcggctcc aacaatgtcc tgacggacaa tggccgcata acagcggtca    6180
ttgactggag cgaggcgatg ttcgggatt cccaatacga ggtcgccaac atcttcttct    6240
ggaggccgtg gttggcttgt atggagcagc agacgcgcta cttcgagcgg aggcatccgg    6300
agcttgcagg atcgccgcgg ctccgggcgt atatgctccg cattggtctt gaccaactct    6360
atcagagctt ggttgacggc aatttcgatg atgcagcttg ggcgcagggt cgatgcgacg    6420
caatcgtccg atccggagcc gggactgtcg gcgtacaca aatcgcccgc agaagcgcgg    6480
ccggccgtct ggaccgatgg ctgtgtagaa gtactcgccg atagtggaaa ccgacgcccc    6540
agcactcgtc cggacccagc tttcttgtac aaagtggagt ccgcaaaaat caccagtctc    6600
```

```
tctctacaaa tctatctctc tctatttttc tccagaataa tgtgtgagta gttcccagat    6660
aagggaatta gggttcttat agggtttcgc tcatgtgttg agcatataag aaacccttag    6720
tatgtatttg tatttgtaaa atacttctat caataaaatt tctaattcct aaaaccaaaa    6780
tccagtgacc tcaactttat tatacatagt tgataattca ctggccgtgc ttattccatg    6840
gctgcaggtc gacgaattca ccggttaggg ataacagggt aatcgctacc ttaggaccgt    6900
tatagttacg gccagtgcca ttaccctgtt atccctaacc ggtgacaact ttgtatagaa    6960
aagttggttt gtgtcttcta gattaatcct ccaaactttt gattaaccaa aaaaattatc    7020
aaactaacat gttctccttt tttctttaga aattctaacg aatttatctt tatactgatt    7080
tgaatatact taatttggtc atttggatgc cctttacaac ctccttacca aactcactat    7140
ggcaaatata tactattttc cattgtaaca taaatgtcca taatttgaat taaattcgtt    7200
gcagtacgaa accatccaac tttgtccaaa acaaaatcc ttataactat ttactttaat    7260
gtaaatatat cctctacttt tgtttttaca accctagctc aaacaaattt attatttgcg    7320
ataaaaaatc atatcgaaca aactcgatga tttttttttt cttacgttat taatgaaact    7380
aaaatataga aaaaaacaag atgaaccaaa ttttcaccta tctaactact taaatataat    7440
atgattaaat ttggtaaagt ttgaaaagtt tctttagaaa tgtgaaatat tgatcacagt    7500
ttctattgct aaaatcacca acaaaacgca tgtcgccatt cataattatg gtttcacacc    7560
tacaactagg ctaataagta aataagtaga caactagact caggtttgaa aaaaccataa    7620
aagccatata gcgttttctc attgaaactg cgaacacgat cgtgtgaatg ttgcagtttc    7680
tagttttgat acaaacaaac aaaaacacaa tttaatctta gattaaaaag aaaaaagaga    7740
acggagccca ctagccactc cttcaaacgt gtcttaccaa ctctcttcta gaaacaaatt    7800
aggcttcacc ttcctcttcc aacctctctc tctctctctc tctcttttc tcaaaccatc    7860 tctccataaa gccctaattt cttcatcaca agaatcagaa gaagaaacaa gtttgtacaa    7920
aaaagcaggc ttactgcaaa aaacttatgg acctgcatct aattttcggt ccaacttgca    7980
caggaaagac gacgaccgcg atagctcttg cccagcagac agggcttcca gtcctttcgc    8040
ttgatcgggt ccaatgctgt cctcaactat caaccggaag cggacgacca acagtggaag    8100
aactgaaagg aacgacgcgt ctctaccttg atgatcggcc tctggtggag ggtatcatcg    8160
cagccaagca agctcatcat aggctgatcg aggaggtgta taatcatgag gccaacggcg    8220
ggcttattct tgagggagga tccacctcgt tgctcaactg catggcgcga aacagctatt    8280
ggagtgcaga ttttcgttgg catattattc gccacaagtt acccgaccaa gagaccttca    8340
tgaaagcggc caaggccaga gttaagcaga tgttgcaccc cgctgcaggc cattctatta    8400
ttcaagagtt ggtttatctt tggaatgaac ctcggctgag gcccattctg aaagagatcg    8460
atggatatcg atatgccatg ttgtttgcta gccagaacca gatcacggca gatatgctat    8520
tgcagcttga cgcaaatatg gaaggtaagt tgattaatgg gatcgctcag gagtatttca    8580
tccatgcgcg ccaacaggaa cagaaattcc cccaagttaa cgcagccgct ttcgacggat    8640
tcgaaggtca tccgttcgga atgtattagg tacccagctt tcttgtacaa agtgggatcg    8700
ttcaaacatt tggcaataaa gtttcttaag attgaatcct gttgccggtc ttgcgatgat    8760
tatcatataa tttctgttga attacgttaa gcatgtaata attaacatgt aatgcatgac    8820
gttatttatg agatgggttt ttatgattag agtcccgcaa ttatacattt aatacgcgat    8880
agaaaacaaa atatagcgcg caaactagga taaattatcg cgcgcggtgt catctatgtt    8940
actagatcca actttattat acatagttga ttcgtcgacc tgcagtcgct accttaggac    9000
```

```
cgttatagtt atggcaaaca gctattatgg gtattatggg tggttcttta tgcggacact   9060
gacggcttta tgcctgcagg tcgcgagcga tcgcggtacc gcccgggcgt cgacaggcct   9120
aagcttagct tgagcttgga tcagattgtc gtttcccgcc ttcagtttaa actatcagtg   9180
tttgacagga tatattggcg ggtaaaccta agagaaaaga gcgttattta gaataacgga   9240
tatttaaaag ggcgtgaaaa ggtttatccg ttcgtccatt tgtatgtgca tgccaaccac   9300
agggttcccc tcgggatcaa agtactttga tccaaccctt ccgctgctat agtgcagtcg   9360
gcttctgacg ttcagtgcag ccgtcttctg aaaacgacat gtcgcacaag tcctaagtta   9420
cgcgacaggc tgccgccctg ccttttcct ggcgttttct tgtcgcgtgt tttagtcgca   9480
taaagtagaa tacttgcgac tagaaccgga gacattacgc catgaacaag agcgccgccg   9540
ctggcctgct gggctatgcc cgcgtcagca ccgacgacca ggacttgacc aaccaacggg   9600
ccgaactgca cgcggccggc tgcaccaagc tgttttccga agatcacc ggcaccaggc    9660
gcgaccgccc ggagctggcc aggatgcttg accacctacg ccctggcgac gttgtgacag   9720
tgaccaggct agaccgcctg gcccgcagca cccgcgacct actggacatt gccgagcgca   9780
tccaggaggc cggcgcgggc ctgcgtagcc tggcagagcc gtgggccgac accaccacgc   9840
cggccggccg catggtgttg accgtgttcg ccggcattgc cgagttcgag cgttccctaa   9900
tcatcgaccg cacccggagc gggcgcgagg ccgccaaggc ccgaggcgtg aagtttggcc   9960
cccgccctac cctcacccg gcacagatcg cgcacgcccg cgagctgatc gaccaggaag  10020
gccgcaccgt gaaagaggcg gctgcactgc ttggcgtgca tcgctcgacc ctgtaccgcg  10080
cacttgagcg cagcgaggaa gtgacgccca ccgaggccag gcggcgcggt gccttccgtg  10140
aggacgcatt gaccgaggcc gacgccctgg cggccgccga gaatgaacgc caagaggaac  10200
aagcatgaaa ccgcaccagg acggccagga cgaaccgttt tcattaccg aagagatcga  10260
ggcggagatg atcgcggccg ggtacgtgtt cgagccgccc gcgcacgtct caaccgtgcg  10320
gctgcatgaa atcctggccg gtttgtctga tgccaagctg gcggcctggc cggccagctt  10380
ggccgctgaa gaaaccgagc gccgccgtct aaaaaggtga tgtgtatttg agtaaaacag  10440
cttgcgtcat gcggtcgctg cgtatatgat gcgatgagta aataaacaaa tacgcaaggg  10500
gaacgcatga aggttatcgc tgtacttaac cagaaaggcg ggtcaggcaa gacgaccatc  10560
gcaacccatc tagcccgcgc cctgcaactc gccggggccg atgttctgtt agtcgattcc  10620
gatccccagg gcagtgcccg cgattgggcg ccgtgcggg aagatcaacc gctaaccgtt  10680
gtcggcatcg accgcccgac gattgaccgc gacgtgaagg ccatcggccg gcgcgacttc  10740
gtagtgatcg acggagcgcc ccaggcggcg gacttggctg tgtccgcgat caaggcagcc  10800
gacttcgtgc tgattccggt gcagccaagc ccttacgaca tatgggccac cgccgacctg  10860
gtggagctgg ttaagcagcg cattgaggtc acggatggaa ggctacaagc ggcctttgtc  10920
gtgtcgcggg cgatcaaagg cacgcgcatc ggcggtgagg ttgccgaggc gctggccggg  10980
tacgagctgc ccattcttga                                              11000
```

<210> SEQ ID NO 14
<211> LENGTH: 10682
<212> TYPE: DNA
<213> ORGANISM: Artificial
<220> FEATURE:
<223> OTHER INFORMATION: Synthetic construct

<400> SEQUENCE: 14

```
gtcccgtatc acgcagcgcg tgagctaccc aggcactgcc gccgccggca caaccgttct      60
tgaatcagaa cccggggcg acgctgcccg cgaggtccag cgctggccg ctgaaattaa       120 atcaaaactc atttgagtta atgaggtaaa agagaaaatga gcaaaagcac aaacacgcta   180
agtgccggcc gtccgagcgc acgcagcagc aaggctgcaa cgttggccag cctggcagac   240
acgccagcca tgaagcgggt caactttcag ttgccggcgg aggatcacac caagctgaag   300
atgtacgcgg tacgccaagg caagaccatt accgagctgc tatctgaata catcgcgcag   360
ctaccagagt aaatgagcaa atgaataaat gagtagatga atttagcgg ctaaaggagg     420 cggcatggaa atcaagaac aaccaggcac cgacgccgtg gaatgcccca tgtgtggagg    480
aacgggcggt tggccaggcg taagcggctg ggttgtctgc cggccctgca atggcactgg   540 aaccccaag cccgaggaat cggcgtgacg gtcgcaaacc atccggcccg gtacaaatcg    600
gcgcggcgct gggtgatgac ctggtggaga agttgaaggc cgcgcaggcc gcccagcggc   660
aacgcatcga ggcagaagca cgccccggtg aatcgtggca agcggccgct gatcgaatcc   720
gcaaagaatc ccggcaaccg ccggcagccg gtgcgccgtc gattaggaag ccgcccaagg   780
gcgacgagca accagatttt ttcgttccga tgctctatga cgtgggcacc cgcgatagtc   840
gcagcatcat ggacgtggcc gttttccgtc tgtcgaagcg tgaccgacga gctggcgagg   900
tgatccgcta cgagcttcca gacgggcacg tagaggtttc cgcagggccg gccggcatgg   960
ccagtgtgtg ggattacgac ctggtactga tggcggtttc ccatctaacc gaatccatga  1020
accgataccg ggaagggaag ggagacaagc ccggccgcgt gttccgtcca cacgttgcgg   1080
acgtactcaa gttctgccgg cgagccgatg gcggaaagca gaaagacgac ctggtagaaa   1140
cctgcattcg gttaaacacc acgcacgttg ccatgcagcg tacgaagaag gccaagaacg   1200
gccgcctggt gacggtatcc gagggtgaag ccttgattag ccgctacaag atcgtaaaga   1260
gcgaaaccgg gcggccggag tacatcgaga tcgagctagc tgattggatg taccgcgaga   1320
tcacagaagg caagaacccg gacgtgctga cggttcaccc cgattacttt ttgatcgatc   1380
ccggcatcgg ccgttttctc taccgcctgg cacgccgcgc cgcaggcaag gcagaagcca   1440
gatggttgtt caagacgatc tacgaacgca gtggcagcgc cggagagttc aagaagttct   1500
gtttcaccgt gcgcaagctg atcgggtcaa atgacctgcc ggagtacgat ttgaaggagg   1560
aggcggggca ggctggcccg atcctagtca tgcgctaccg caacctgatc gagggcgaag   1620
catccgccgg ttcctaatgt acggagcaga tgctagggca aattgcccta gcagggaaa    1680 aaggtcgaaa aggtctcttt cctgtggata gcacgtacat tgggaaccca aagccgtaca   1740
ttgggaaccg gaacccgtac attgggaacc caaagccgta cattgggaac cggtcacaca   1800
tgtaagtgac tgatataaaa gagaaaaaag cgattttttc cgcctaaaac tctttaaaac   1860
ttattaaaac tcttaaaacc cgcctggcct gtgcataact gtctggccag cgcacagccg   1920
aagagctgca aaaagcgcct acccttcggt cgctgcgctc cctacgcccc gccgcttcgc   1980
gtcggcctat cgcggccgct ggccgctcaa aaatggctgg cctacggcca ggcaatctac   2040
cagggcgcgg acaagccgcg ccgtcgccac tcgaccgccg cgcccacat caaggcaccc   2100 tgcctcgcgc gtttcggtga tgacggtgaa aacctctgac acatgcagct cccggagacg   2160
gtcacagctt gtctgtaagc ggatgccggg agcagacaag cccgtcaggg cgcgtcagcg   2220
ggtgttggcg ggtgtcgggg cgcagccatg acccagtcac gtagcgatag cggagtgtat   2280
actggcttaa ctatgcggca tcagagcaga ttgtactgag agtgcaccat atgcggtgtg   2340
aaataccgca cagatgcgta aggagaaaat accgcatcag gcgctcttcc gcttcctcgc   2400
```

```
tcactgactc gctgcgctcg gtcgttcggc tgcggcgagc ggtatcagct cactcaaagg   2460
cggtaatacg gttatccaca gaatcagggg ataacgcagg aaagaacatg tgagcaaaag   2520
gccagcaaaa ggccaggaac cgtaaaaagg ccgcgttgct ggcgtttttc cataggctcc   2580
gcccccctga cgagcatcac aaaaatcgac gctcaagtca gaggtggcga acccgacag    2640 gactataaag ataccaggcg tttccccctg gaagctccct cgtgcgctct cctgttccga   2700
ccctgccgct taccggatac ctgtccgcct ttctcccttc gggaagcgtg gcgctttctc   2760
atagctcacg ctgtaggtat ctcagttcgg tgtaggtcgt tcgctccaag ctgggctgtg   2820
tgcacgaacc ccccgttcag cccgaccgct gcgccttatc cggtaactat cgtcttgagt   2880
ccaacccggt aagacacgac ttatcgccac tggcagcagc cactggtaac aggattagca   2940
gagcgaggta tgtaggcggt gctacagagt tcttgaagtg gtggcctaac tacggctaca   3000
ctagaaggac agtatttggt atctgcgctc tgctgaagcc agttaccttc ggaaaaagag   3060
ttggtagctc ttgatccggc aaacaaacca ccgctggtag cggtggtttt tttgtttgca   3120
agcagcagat tacgcgcaga aaaaaggat ctcaagaaga tcctttgatc ttttctacgg    3180
ggtctgacgc tcagtggaac gaaaactcac gttaagggat tttggtcatg catgatatat   3240
ctcccaattt gtgtagggct tattatgcac gcttaaaaat aataaaagca gacttgacct   3300
gatagtttgg ctgtgagcaa ttatgtgctt agtgcatcta atcgcttgag ttaacgccgg   3360
cgaagcggcg tcggcttgaa cgaatttcta gctagacatt atttgccgac taccttggtg   3420
atctcgcctt tcacgtagtg gacaaattct ccaactgat ctgcgcgcga ggccaagcga    3480
tcttcttctt gtccaagata agcctgtcta gcttcaagta tgacgggctg atactgggcc   3540
ggcaggcgct ccattgccca gtcggcagcg acatccttcg gcgcgatttt gccggttact   3600
gcgctgtacc aaatgcggga caacgtaagc actacatttc gctcatcgcc agcccagtcg   3660
ggcggcgagt tccatagcgt taaggtttca tttagcgcct caaatagatc ctgttcagga   3720
accggatcaa agagttcctc cgccgctgga cctaccaagg caacgctatg ttctcttgct   3780
tttgtcagca agatagccag atcaatgtcg atcgtggctg gctcgaagat acctgcaaga   3840
atgtcattgc gctgccattc tccaaattgc agttcgcgct tagctggata cgccacgga    3900 atgatgtcgt cgtgcacaac aatggtgact tctacagcgc ggagaatctc gctctctcca   3960
ggggaagccg aagtttccaa aaggtcgttg atcaaagctc gccgcgttgt ttcatcaagc   4020
cttacggtca ccgtaaccag caaatcaata tcactgtgtg gcttcaggcc gccatccact   4080
gcggagccgt acaaatgtac ggccagcaac gtcggttcga gatggcgctc gatgacgcca   4140
actacctctg atagttgagt cgatacttcg gcgatcaccg cttcccccat gatgtttaac   4200
tttgttttag ggcgactgcc ctgctgcgta acatcgttgc tgctccataa catcaaacat   4260
cgacccacgg cgtaacgcgc ttgctgcttg gatgcccgag gcatagactg taccccaaaa   4320
aaacatgtca taacaagaag ccatgaaaac cgccactgcg ccgttaccac cgctgcgttc   4380
ggtcaaggtt ctgaccagt tgcgtgacgg cagttacgct acttgcatta cagcttacga    4440
accgaacgag gcttatgtcc actgggttcg tgcccgaatt gatcacaggc agcaacgctc   4500
tgtcatcgtt acaatcaaca tgctaccctc cgcgagatca tccgtgtttc aaacccggca   4560
gcttagttgc cgttcttccg aatagcatcg gtaacatgag caaagtctgc cgccttacaa   4620
cggctctccc gctgacgccg tcccggactg atgggctgcc tgtatcgagt ggtgattttg   4680
tgccgagctg ccggtcgggg agctgttggc tggctggtgg caggatatat tgtggtgtaa   4740
```

```
acaaattgac gcttagacaa cttaataaca cattgcggac gttttaatg tactgaatta    4800
acgccgaatt gaattcctcg agtacgtagg atccatttaa attctagagg cgcgccgata    4860
tcctctctta aggtagcgag ctcttaatta atagggataa cagggtaatg cggccgcaag    4920
ctaaaacgac ggccagtgaa ttatcaactt tgtatagaaa agttgctctg ccgacagtgg    4980
tcccaaagat ggacccccac ccacgaggag catcgtggaa aaagaagacg ttccaaccac    5040
gtcttcaaag caagtggatt gatgtgataa catggtggag cacgcactc tcgtctactc     5100
caagaatatc aaagatacag tctcagaaga ccaagggct attgagactt ttcaacaaag     5160
ggtaatatcg ggaaacctcc tcggattcca ttgcccagct atctgtcact tcatcaaaag    5220
gacagtagaa aaggaaggtg gcacctacaa atgccatcat tgcgataaag gaaaggctat    5280
cgttcaagat gcctctgccg acagtggtcc caaagatgga cccccaccca cgaggagcat    5340
cgtggaaaaa gaagacgttc caaccacgtc ttcaaagcaa gtggattgat gtgatatctc    5400
cactgacgta agggatgacg cacaatccca ctatccttcg caagacccctt cctctatata   5460
aggaagttca tttcatttgg agaggacacg ctgcaagttt gtacaaaaaa gcaggctaga    5520
ccggggggca atgagatatg aaaaagcctg aactcaccgc gacgtctgtc gagaagtttc    5580
tgatcgaaaa gttcgacagc gtctccgacc tgatgcagct ctcggagggc gaagaatctc    5640
gtgctttcag cttcgatgta ggagggcgtg gatatgtcct gcgggtaaat agctgcgccg    5700
atggtttcta caaagatcgt tatgtttatc ggcactttgc atcggccgcg ctcccgattc    5760
cggaagtgct tgacattggg gaattcagcg agagcctgac ctattgcatc tcccgccgtg    5820
cacagggtgt cacgttgcaa gacctgcctg aaaccgaact gcccgctgtt ctgcagccgg    5880
tcgcggaggc catggatgcg atcgctgcgg ccgatcttag ccagacgagc gggttcggcc    5940
cattcggacc gcaaggaatc ggtcaataca ctacatggcg tgatttcata tgcgcgattg    6000
ctgatcccca tgtgtatcac tggcaaactg tgatggacga caccgtcagt gcgtccgtcg    6060
cgcaggctct cgatgagctg atgctttggg ccgaggactg ccccgaagtc cggcacctcg    6120
tgcacgcgga tttcggctcc aacaatgtcc tgacggacaa tggccgcata acagcggtca    6180
ttgactggag cgaggcgatg ttcggggatt cccaatacga ggtcgccaac atcttcttct    6240
ggaggccgtg gttggcttgt atggagcagc agacgcgcta cttcgagcgg aggcatccgg    6300
agcttgcagg atcgccgcgg ctccgggcgt atatgctccg cattggtctt gaccaactct    6360
atcagagctt ggttgacggc aatttcgatg atgcagcttg ggcgcagggt cgatgcgacg    6420
caatcgtccg atccggagcc gggactgtcg ggcgtacaca atcgcccgc agaagcgcgg     6480
ccggccgtct ggaccgatgg ctgtgtagaa gtactcgccg atagtggaaa ccgacgcccc    6540
agcactcgtc cggacccagc tttcttgtac aaagtggagt ccgcaaaaat caccagtctc    6600
tctctacaaa tctatctctc tctatttttc tccagaataa tgtgtgagta gttcccagat    6660
aagggaatta gggttcttat agggtttcgc tcatgtgttg agcatataag aaacccttag    6720
tatgtatttg tatttgtaaa atacttctat caataaaatt tctaattcct aaaaccaaaa    6780
tccagtgacc tcaactttat tatacatagt tgataattca ctggccgtgc ttattccatg    6840
gctgcaggtc gacgaattca ccggttaggg ataacagggt aataactata acggtcctaa    6900
ggtagcgagc ggccgcaagc taaaacgacg gccagtgaat tatcaacttt gtatagaaaa    6960
gttggtttgt gtcttctaga ttaatcctcc aaacttttga ttaaccaaaa aaattatcaa    7020
actaacatgt tctcctttt tctttagaaa ttctaacgaa tttatcttta tactgatttg     7080
aatatactta atttggtcat ttggatgccc tttacaacct ccttaccaaa atattgatca    7140
```

```
cagtttctat tgctaaaatc accaacaaaa cgcatgtcgc cattcataat tatggtttca    7200
cacctacaac taggctaata agtaaataag tagacaacta gactcaggtt tgaaaaaacc    7260
ataaaagcca tatagcgttt tctcattgaa actgcgaaca cgatcgtgtg aatgttgcag    7320
tttctagttt tgatacaaac aaacaaaaac acaatttaat cttagattaa aaagaaaaaa    7380
gagaacggag cccactagcc actccttcaa acgtgtctta ccaactctct tctagaaaca    7440
aattaggctt caccttcctc ttccaacctc tctctctctc tctctctctt tttctcaaac    7500
catctctcca taaagcccta atttcttcat cacaagaatc agaagaagaa acaagtttgt    7560 acaaaaagc aggcttactg caaaaaactt atggacctgc atctaatttt cggtccaact     7620
tgcacaggaa agacgacgac cgcgatagct cttgcccagc agacagggct tccagtcctt    7680
tcgcttgatc gggtccaatg ctgtcctcaa ctatcaaccg gaagcggacg accaacagtg    7740
gaagaactga aggaacgac gcgtctctac cttgatgatc ggcctctggt ggagggtatc     7800
atcgcagcca agcaagctca tcataggctg atcgaggagg tgtataatca tgaggccaac    7860
ggcgggctta ttcttgaggg aggatccacc tcgttgctca actgcatggc gcgaaacagc    7920
tattggagtg cagattttcg ttggcatatt attcgccaca agttaccga ccaagagacc     7980 ttcatgaaag cggccaaggc cagagttaag cagatgttgc accccgctgc aggccattct    8040
attattcaag agttggttta tctttggaat gaacctcggc tgaggcccat tctgaaagag    8100
atcgatggat atcgatatgc catgttgttt gctagccaga accagatcac ggcagatatg    8160
ctattgcagc ttgacgcaaa tatggaaggt aagttgatta atgggatcgc tcaggagtat    8220
ttcatccatg cgcgccaaca ggaacagaaa ttcccccaag ttaacgcagc cgctttcgac    8280
ggattcgaag gtcatccgtt cggaatgtat taggtaccca gctttcttgt acaaagtggg    8340
atcgttcaaa catttggcaa taaagtttct taagattgaa tcctgttgcc ggtcttgcga    8400
tgattatcat ataatttctg ttgaattacg ttaagcatgt aataattaac atgtaatgca    8460
tgacgttatt tatgagatgg gttttatga ttagagtccc gcaattatac atttaatacg     8520
cgatagaaaa caaatatag cgcgcaaact aggataaatt atcgcgcgcg gtgtcatcta     8580
tgttactaga tccaacttta ttatacatag ttgataattc actggccgtc gcttattcca    8640
tggctgcagg tcgacgaatt caccggttaa ctataacggt cctaaggtag cgatggcaaa    8700
cagctattat gggtattatg ggtggttctt tatgcggaca ctgacggctt tatgcctgca    8760
ggtcgcgagc gatcgcggta ccgcccgggc gtcgacaggc ctaagcttag cttgagcttg    8820
gatcagattg tcgtttcccg ccttcagttt aaactatcag tgtttgacag gatatattgg    8880
cgggtaaacc taagagaaaa gagcgtttat tagaataacg gatatttaaa agggcgtgaa    8940
aaggtttatc cgttcgtcca tttgtatgtg catgccaacc acagggttcc cctcgggatc    9000
aaagtacttt gatccaaccc ctccgctgct atagtgcagt cggcttctga cgttcagtgc    9060
agccgtcttc tgaaaacgac atgtcgcaca agtcctaagt tacgcgacag gctgccgccc    9120 tgccctttc ctggcgtttt cttgtcgcgt gttttagtcg cataaagtag aatacttgcg     9180
actagaaccg gagacattac gccatgaaca agagcgccgc cgctggcctg ctgggctatg    9240
cccgcgtcag caccgacgac caggacttga ccaaccaacg gccgaactg cacgcggcc      9300 gctgcaccaa gctgtttcc gagaagatca ccggcaccag gcgcgaccgc ccggagctgg     9360
ccaggatgct tgaccaccta cgccctggcg acgttgtgac agtgaccagg ctagaccgcc    9420
tggcccgcag cacccgcgac ctactggaca ttgccgagcg catccaggag gccggcgcgg    9480
```

```
gcctgcgtag cctggcagag ccgtgggccg acaccaccac gccggccggc cgcatggtgt      9540
tgaccgtgtt cgccggcatt gccgagttcg agcgttccct aatcatcgac cgcacccgga      9600
gcgggcgcga ggccgccaag gcccgaggcg tgaagtttgg ccccccgccct accctcaccc     9660 cggcacagat cgcgcacgcc cgcgagctga tcgaccagga aggccgcacc gtgaaagagg      9720
cggctgcact gcttggcgtg catcgctcga ccctgtaccg cgcacttgag cgcagcgagg      9780
aagtgacgcc caccgaggcc aggcggcgcg gtgccttccg tgaggacgca ttgaccgagg      9840
ccgacgccct ggcggccgcc gagaatgaac gccaagagga acaagcatga aaccgcacca      9900
ggacggccag gacgaaccgt ttttcattac cgaagagatc gaggcggaga tgatcgcggc      9960
cgggtacgtg ttcgagccgc ccgcgcacgt ctcaaccgtg cggctgcatg aaatcctggc     10020
cggtttgtct gatgccaagc tggcggcctg gccggccagc ttggccgctg aagaaaccga     10080
gcgccgccgt ctaaaaaggt gatgtgtatt tgagtaaaac agcttgcgtc atgcggtcgc     10140
tgcgtatatg atgcgatgag taaataaaca aatacgcaag gggaacgcat gaaggttatc     10200
gctgtactta accagaaagg cgggtcaggc aagacgacca tcgcaaccca tctagcccgc     10260
gccctgcaac tcgccggggc cgatgttctg ttagtcgatt ccgatcccca gggcagtgcc     10320
cgcgattggg cggccgtgcg gaagatcaa ccgctaaccg ttgtcggcat cgaccgcccg      10380
acgattgacc gcgacgtgaa ggccatcggc cggcgcgact tcgtagtgat cgacggagcg     10440
ccccaggcgg cggacttggc tgtgtccgcg atcaaggcag ccgacttcgt gctgattccg     10500
gtgcagccaa gcccttacga catatgggcc accgccgacc tggtggagct ggttaagcag     10560
cgcattgagg tcacggatgg aaggctacaa gcggcctttg tcgtgtcgcg ggcgatcaaa     10620
ggcacgcgca tcggcggtga ggttgccgag gcgctggccg ggtacgagct gcccattctt     10680
ga                                                                    10682

<210> SEQ ID NO 15
<211> LENGTH: 7862
<212> TYPE: DNA
<213> ORGANISM: Artificial
<220> FEATURE:
<223> OTHER INFORMATION: Synthetic construct

<400> SEQUENCE: 15
ttatacatag ttgataattc actggccgtc gtgggggatc cactagttct agagcggccg       60
ccaccgcggt ggagctccag cttttgttcc ctttagtgag ggttaatttc gagcttggcg      120
taatcatggt catagctgtt tcctgtgtga aattgttatc cgctcacaat tccacacaac      180
atacgagccg gaagcataaa gtgtaaagcc tggggtgcct aatgagtgag ctaactcaca      240
ttaattgcgt tgcgctcact gcccgctttc cagtcgggaa acctgtcgtg ccagctgcat      300
taatgaatcg gccaacgcgc ggggagaggc ggtttgcgta ttgggcgctc ttccgcttcc      360
tcgctcactg actcgctgcg ctcggtcgtt cggctgcggc gagcggtatc agctcactca      420
aaggcggtaa tacggttatc cacagaatca ggggataacg caggaaagaa catgtgagca      480
aaaggccagc aaaaggccag gaaccgtaaa aaggccgcgt tgctggcgtt tttccatagg      540
ctccgccccc ctgacgagca tcacaaaaat cgacgctcaa gtcagaggtg gcgaaacccg      600
acaggactat aaagatacca ggcgtttccc cctggaagct ccctcgtgcg ctctcctgtt      660
ccgaccctgc cgcttaccgg atacctgtcc gcctttctcc cttcgggaag cgtggcgctt      720
tctcatagct cacgctgtag gtatctcagt tcggtgtagg tcgttcgctc caagctgggc      780
tgtgtgcacg aaccccccgt tcagcccgac cgctgcgcct tatccggtaa ctatcgtctt      840
```

-continued

```
gagtccaacc cggtaagaca cgacttatcg ccactggcag cagccactgg taacaggatt      900
agcagagcga ggtatgtagg cggtgctaca gagttcttga agtggtggcc taactacggc      960
tacactagaa ggacagtatt tggtatctgc gctctgctga agccagttac cttcggaaaa     1020
agagttggta gctcttgatc cggcaaacaa accaccgctg gtagcggtgg ttttttttgtt    1080
tgcaagcagc agattacgcg cagaaaaaaa ggatctcaag aagatccttt gatcttttct     1140
acggggtctg acgctcagtg gaacgaaaac tcacgttaag gattttggt catgagatta      1200
tcaaaaagga tcttcaccta gatccttttta aattaaaaat gaagttttaa atcaatctaa    1260
agtatatatg agtaaacttg gtctgacagt taccaatgct taatcagtga ggcacctatc    1320
tcagcgatct gtctatttcg ttcatccata gttgcctgac tccccgtcgt gtagataact    1380
acgatacggg agggcttacc atctggcccc agtgctgcaa tgataccgcg agacccacgc    1440
tcaccggctc cagatttatc agcaataaac cagccagccg aagggccga gcgcagaagt     1500
ggtcctgcaa ctttatccgc ctccatccag tctattaatt gttgccggga agctagagta    1560
agtagttcgc cagttaatag tttgcgcaac gttgttgcca ttgctacagg catcgtggtg    1620
tcacgctcgt cgtttggtat ggcttcattc agctccggtt cccaacgatc aaggcgagtt    1680
acatgatccc ccatgttgtg caaaaaagcg gttagctcct tcggtcctcc gatcgttgtc    1740
agaagtaagt tggccgcagt gttatcactc atggttatgg cagcactgca taattctctt    1800
actgtcatgc catccgtaag atgcttttct gtgactggtg agtactcaac caagtcattc    1860
tgagaatagt gtatgcggcg accgagttgc tcttgcccgg cgtcaatacg ggataatacc    1920
gcgccacata gcagaacttt aaaagtgctc atcattggaa aacgttcttc ggggcgaaaa    1980
ctctcaagga tcttaccgct gttgagatcc agttcgatgt aacccactcg tgcacccaac    2040
tgatcttcag catcttttac tttcaccagc gtttctgggt gagcaaaaac aggaaggcaa    2100
aatgccgcaa aaaagggaat aagggcgaca cggaaatgtt gaatactcat actcttcctt    2160
tttcaatatt attgaagcat ttatcagggt tattgtctca tgagcggata catatttgaa    2220
tgtatttaga aaaataaaca aatagggggt ccgcgcacat ttccccgaaa agtgccacct    2280
gacgcgccct gtagcggcgc attaagcgcg gcgggtgtgg tggttacgcg cagcgtgacc    2340
gctacacttg ccagcgccct agcgcccgct cctttcgctt tcttcccttc ctttctcgcc    2400
acgttcgccg gctttccccg tcaagctcta aatcgggggc tccctttagg gttccgattt    2460
agtgctttac ggcacctcga ccccaaaaaa cttgattagg gtgatggttc acgtagtggg    2520
ccatcgccct gatagacggt ttttcgccct ttgacgttgg agtccacgtt ctttaatagt    2580
ggactcttgt tccaaactgg aacaacactc aaccctatct cggtctattc ttttgattta    2640
taagggattt tgccgatttc ggcctattgg ttaaaaaatg agctgattta caaaaatttt    2700
aacgcgaatt ttaacaaaat attaacgctt acaatttcca ttcgccattc aggctgcgca    2760
actgttggga agggcgatcg gtgcgggcct cttcgctatt acgccagctg gcgaaagggg    2820
gatgtgctgc aaggcgatta agttgggtaa cgccagggtt ttcccagtca cgacgttgta    2880
aaacgacggc cagtgaattg taatacgact cactataggg cgaattgggt accgggcccc    2940
ccctcgaggt cgacggtatc gataagcttg atatcgaatt ctcatgtttg acagcttatc    3000
atcggatcta gtaacataga tgacaccgcg cgcgataatt tatcctagtt tgcgcgctat    3060
attttgtttt ctatcgcgta ttaaatgtat aattgcggga ctctaatcat aaaaacccat    3120
ctcataaata acgtcatgca ttacatgtta attattacat gcttaacgta attcaacaga    3180
```

```
aattatatga taatcatcgc aagaccggca acaggattca atcttaagaa actttattgc    3240
caaatgtttg aacgatctgc aggtcgacgg atcagatctc ggtgacgggc aggaccggac    3300
ggggcggtac cggcaggctg aagtccagct gccagaaacc cacgtcatgc cagttcccgt    3360
gcttgaagcc ggccgcccgc agcatgccgc gggggcata tccgagcgcc tcgtgcatgc     3420
gcacgctcgg gtcgttgggc agcccgatga cagcgaccac gctcttgaag ccctgtgcct    3480
ccagggactt cagcaggtgg gtgtagagcg tggagcccag tcccgtccgc tggtggcggg    3540
gggagacgta cacggtcgac tcggccgtcc agtcgtaggc gttgcgtgcc ttccagggc     3600
ccgcgtaggc gatgccggcg acctcgccgt ccacctcggc gacgagccag ggatagcgct    3660
cccgcagacg gacgaggtcg tccgtccact cctgcggttc ctgcggctcg gtacggaagt    3720
tgaccgtgct tgtctcgatg tagtggttga cgatggtgca gaccgccggc atgtccgcct    3780
cggtggcacg gcggatgtcg gccgggcgtc gttctgggct catggttact tcctaatcga    3840
tggatcctct agagtcgacc tgcagaagta acaccaaaca acaggtgag catcgacaaa     3900
agaaacagta ccaagcaaat aaatagcgta tgaaggcagg gctaaaaaaa tccacatata    3960
gctgctgcat atgccatcat ccaagtatat caagatcaaa ataattataa aacatacttg    4020
tttattataa tagataggta ctcaaggtta gagcatatga atagatgctg catatgccat    4080
catgtatatg catcagtaaa acccacatca acatgtatac ctatcctaga tcgatatttc    4140
catccatctt aaactcgtaa ctatgaagat gtatgacaca cacatacagt tccaaaatta    4200
ataaatacac caggtagttt gaaacagtat tctactccga tctagaacga atgaacgacc    4260
gcccaaccac accacatcat cacaaccaag cgaacaaaaa gcatctctgt atatgcatca    4320
gtaaaacccg catcaacatg tatacctatc ctagatcgat atttccatcc atcattttca    4380
attcgtaact atgaatatgt atggcacaca catacagatc caaaattaat aaatccacca    4440
ggtagtttga aacagaattc tactccgatc tagaacgacc gcccaaccag accacatcat    4500
cacaaccaag acaaaaaaaa gcatgaaaag atgacccgac aaacaagtgc acggcatata    4560
ttgaaataaa ggaaaagggc aaaccaaacc ctatgcaacg aaacaaaaaa aatcatgaaa    4620
tcgatcccgt ctgcggaacg gctagagcca tcccaggatt cccaaagag aaacactggc     4680
aagttagcaa tcagaacgtg tctgacgtac aggtcgcatc cgtgtacgaa cgctagcagc    4740
acggatctaa cacaaacacg gatctaacac aaacatgaac agaagtagaa ctaccgggcc    4800
ctaaccatgg accggaacgc cgatctagag aaggtagaga gggggggggg gggaggacga    4860
gcggcgtacc ttgaagcgga ggtgccgacg ggtggatttg ggggagatct ggttgtgtgt    4920
gtgtgcgctc cgaacaacac gaggttgggg aaagagggtg tggaggggt gtctatttat     4980
tacggcgggc gaggaaggga aagcgaagga gcggtgggaa aggaatcccc cgtagctgcc    5040
ggtgccgtga gaggaggagg aggccgcctg ccgtgccggc tcacgtctgc cgctccgcca    5100
cgcaatttct ggatgccgac agcggagcaa gtccaacggt ggagcggaac tctcgagagg    5160
ggtccagagg cagcgacaga gatgccgtgc cgtctgcttc gcttggcccg acgcgacgct    5220
gctggttcgc tggttggtgt ccgttagact cgtcgacggc gtttaacagg ctggcattat    5280
ctactcgaaa caagaaaaat gtttccttag ttttttttaat ttcttaaagg gtatttgttt    5340
aattttttagt cactttattt tattctattt tatatctaaa ttattaaata aaaaaactaa    5400
aatagagttt tagttttctt aatttagagg ctaaaataga ataaaataga tgtactaaaa    5460
aaattagtct ataaaaacca ttaacccaa ccctaaatg gatgtactaa taaaatggat      5520
gaagtattat ataggtgaag ctatttgcaa aaaaaaagga gaacacatgc acactaaaaa    5580
```

```
gataaaactg tagagtcctg ttgtcaaaat actcaattgt cctttagacc atgtctaact    5640
gttcatttat atgattctct aaaacactga tattattgta gtactataga ttatattatt    5700
cgtagagtaa agtttaaata tatgtataaa gatagataaa ctgcacttca aacaagtgtg    5760
acaaaaaaaa tatgtggtaa ttttttataa cttagacatg caatgctcat tatctctaga    5820
gaggggcacg accgggtcac gctgcactgc aggcatgcaa gcttgaattc ctgcagcccc    5880
gccaagctat caactttgta tagaaaagtt ggtttgtgtc ttctagatta atcctccaaa    5940
cttttgatta accaaaaaaa ttatcaaact aacatgttct cctttttct ttagaaattc     6000
taacgaattt atctttatac tgatttgaat atacttaatt tggtcatttg gatgcccttt    6060
acaacctcct taccaaactc actatggcaa atatatacta ttttccattg taacataaat    6120
gtccataatt tgaattaaat tcgttgcagt acgaaaccat ccaactttgt ccaaaaacaa    6180
aatccttata actatttact ttaatgtaaa tatatcctct acttttgttt ttacaaccct    6240
agctcaaaca aatttattat ttgcgataaa aaatcatatc gaacaaactc gatgattttt    6300
tttttcttac gttattaatg aaactaaaat atagaaaaaa acaagatgaa ccaaattttc    6360
acctatctaa ctacttaaat ataatatgat taaatttggt aaagtttgaa aagtttcttt    6420
agaaatgtga atattgatc acagtttcta ttgctaaaat caccaacaaa acgcatgtcg     6480
ccattcataa ttatggtttc acacctacaa ctaggctaat aagtaaataa gtagacaact    6540
agactcaggt ttgaaaaaac cataaaagcc atatagcgtt ttctcattga aactgcgaac    6600
acgatcgtgt gaatgttgca gtttctagtt ttgatacaaa caaacaaaaa cacaatttaa    6660
tcttagatta aaagaaaaa agagaacgga gcccactagc cactccttca aacgtgtctt     6720
accaactctc ttctagaaac aaattaggct tcaccttcct cttccaacct ctctctctct    6780
ctctctctct ttttctcaaa ccatctctcc ataaagccct aatttcttca tcacaagaat    6840
cagaagaaga aacaagtttg tacaaaaaag caggcttact gcaaaaaact tatggacctg    6900
catctaattt tcggtccaac ttgcacagga agacgacga ccgcgatagc tcttgcccag     6960
cagacagggc ttccagtcct ttcgcttgat cgggtccaat gctgtcctca actatcaacc    7020
ggaagcggac gaccaacagt ggaagaactg aaaggaacga cgcgtctcta ccttgatgat    7080
cggcctctgg tggagggtat catcgcagcc aagcaagctc atcataggct gatcgaggag    7140
gtgtataatc atgaggccaa cggcgggctt attcttgagg gaggatccac ctcgttgctc    7200
aactgcatgg cgcgaaacag ctattggagt gcagattttc gttggcatat tattcgccac    7260
aagttacccg accaagagac cttcatgaaa gcggccaagg ccagagttaa gcagatgttg    7320
cacccgctg caggccattc tattattcaa gagttggttt atctttggaa tgaacctcgg     7380
ctgaggccca ttctgaaaga gatcgatgga tatcgatatg ccatgttgtt tgctagccag    7440
aaccagatca cggcagatat gctattgcag cttgacgcaa atatggaagg taagttgatt    7500
aatgggatcg ctcaggagta tttcatccat gcgcgccaac aggaacagaa attcccccaa    7560
gttaacgcag ccgctttcga cggattcgaa ggtcatccgt tcggaatgta ttaggtaccc    7620
agctttcttg tacaaagtgg agtccgcaaa aatcaccagt ctctctctac aaatctatct    7680
ctctctattt ttctccagaa taatgtgtga gtagttccca gataagggaa ttagggttct    7740
tatagggttt cgctcatgtg ttgagcatat aagaaaccct tagtatgtat ttgtatttgt    7800
aaaatacttc tatcaataaa atttctaatt cctaaaacca aaatccagtg acctcaactt    7860
ta                                                                    7862
```